US008557248B2

(12) United States Patent
Markham

(10) Patent No.: US 8,557,248 B2
(45) Date of Patent: Oct. 15, 2013

(54) METHODS AND COMPOSITIONS FOR TREATING MALARIA

(75) Inventor: Richard Markham, Columbia, MD (US)

(73) Assignee: Cyvax, Inc., Delaware, MD (US)

( * ) Notice: Subject to any disclaimer, the term of this patent is extended or adjusted under 35 U.S.C. 154(b) by 0 days.

(21) Appl. No.: 13/206,471

(22) Filed: Aug. 9, 2011

(65) Prior Publication Data

US 2012/0219614 A1 Aug. 30, 2012

Related U.S. Application Data

(60) Provisional application No. 61/371,923, filed on Aug. 9, 2010, provisional application No. 61/466,175, filed on Mar. 22, 2011.

(51) Int. Cl.
*A61K 39/015* (2006.01)
*A61K 47/00* (2006.01)
*A61K 9/127* (2006.01)
*C07H 21/04* (2006.01)

(52) U.S. Cl.
USPC ............. 424/192.1; 424/278.1; 424/450; 536/23.4

(58) Field of Classification Search
USPC ............. 424/192.1, 450, 278.1; 436/23.4
See application file for complete search history.

(56) References Cited

U.S. PATENT DOCUMENTS

| | | | |
|---|---|---|---|
| 6,898,195 B1 | 5/2005 | Molnoet et al. | |
| 6,991,809 B2 | 1/2006 | Anderson | |
| 7,105,229 B2 | 9/2006 | Anderson | |
| 7,105,574 B1 | 9/2006 | Wheeler | |
| 7,537,768 B2 | 5/2009 | Luke et al. | |
| 7,582,613 B2 | 9/2009 | Wheeler | |
| 7,628,993 B2 | 12/2009 | Vilalta et al. | |
| 7,655,235 B2 | 2/2010 | Ertl | |
| 2005/0053579 A1 | 3/2005 | Galipeau et al. | |
| 2008/0112976 A1 | 5/2008 | Garzino-demo et al. | |
| 2009/0068234 A1* | 3/2009 | Biragyn et al. | 424/277.1 |
| 2011/0110947 A1 | 5/2011 | Kwak et al. | |

FOREIGN PATENT DOCUMENTS

| | | | |
|---|---|---|---|
| EP | 1983047 A1 | 10/2008 | |
| WO | WO/00/78334 | * | 12/2000 |
| WO | WO 00/78334 A1 | 12/2000 | |
| WO | WO 02/92780 A2 | 11/2002 | |
| WO | WO 03/025002 A2 | 3/2003 | |
| WO | WO 03/025002 A3 | 12/2003 | |
| WO | WO 02/92780 A3 | 3/2004 | |
| WO | WO 2004/055187 A1 | 7/2004 | |
| WO | WO 2004/096849 A2 | 11/2004 | |
| WO | WO 2004/096849 A3 | 7/2005 | |
| WO | WO 2008/073160 A2 | 6/2008 | |
| WO | WO 2008/073160 A3 | 1/2009 | |

OTHER PUBLICATIONS

Guo et al(Int Immuno-pharmacol. Jul. 2009;9(7-8):925-30.*
Sedagah et al (Vaccine 24, 2006, 1921-1927.*
Sedagah et al Gene Therapy, 2004, 11, 448-456.*
Biragyn, et al. DNA vaccines encoding human immunodeficiency virus-1 glycoprotein 120 fusions with proinflammatory chemoattractants induce systemic and mucosal immune responses. Blood. Aug. 15, 2002;100(4):1153-9.
Biragyn, et al. Genetic fusion of chemokines to a self tumor antigen induces protective, T-cell dependent antitumor immunity. Nat Biotechnol. Mar. 1999;17(3):253-8.
Biragyn, et al. Mediators of innate immunity that target immature, but not mature, dendritic cells induce antitumor immunity when genetically fused with nonimmunogenic tumor antigens. J Immunol. Dec. 1, 2001;167(11):6644-53.
Biragyn, et al. Models for lymphoma. Curr Protoc Immunol. 2002; Ch.20 Unit 20.6.
Biragyn, et al. Tumor-associated embryonic antigen-expressing vaccines that target CCR6 elicit potent CD8+ T cell-mediated protective and therapeutic antitumor immunity. J Immunol. Jul. 15, 2007;179(2):1381-8.
D'Souza, et al. Improved tuberculosis DNA vaccines by formulation in cationic lipids. Infect Immun. Jul. 2002;70(7):3681-8.
Gao, et al. Abeta40 oligomers identified as a potential biomarker for the diagnosis of Alzheimer's disease. PLoS One. 2010; 5(12):e15725.
Guo, et al. Fusion of antigen to chemokine CCL20 or CXCL13 strategy to enhance DNA vaccine potency. Int Immunopharmacol. 2009; 9:925-930.
Hahn, et al. Comparison of the immunological memory after DNA vaccination and protein vaccination against anthrax in sheep. Vaccine. May 22, 2006;24(21):4595-7. Epub Aug. 22, 2005.
Hartikka, et al. Vaxfectin enhances the humoral immune response to plasmid DNA-encoded antigens. Vaccine. Feb. 28, 2001;19(15-16):1911-23.
Hartikka, et al. Vaxfectin, a cationic lipid-based adjuvant for protein-based influenza vaccines. Vaccine. Oct. 30, 2009;27(46):6399-403. Epub Jun. 21, 2009.
Jimenez, et al. Vaxfectin-formulated influenza DNA vaccines encoding NP and M2 viral proteins protect mice against lethal viral challenge. Hum Vaccin. Sep.-Oct. 2007;3(5):157-64. Epub Mar. 20, 2007.
Lalor, et al. Plasmid DNA-based vaccines protect mice and ferrets against lethal challenge with A/Vietnam/1203/04 (H5N1) influenza virus. J Infect Dis. Jun. 15, 2008;197(12):1643-52.
Locher, et al. Evaluation of genetic immunization adjuvants to improve the effectiveness of a human immunodeficiency virus type 2 (HIV-2) envelope DNA vaccine. DNA Cell Biol. Feb. 2004;23(2):107-10.
Margalith, et al. Sustained protective rabies neutralizing antibody titers after administration of cationic lipid-formulated pDNA vaccine. Genet Vaccines Ther. Feb. 15, 2006;4:2.

(Continued)

*Primary Examiner* — Anoop Singh
(74) *Attorney, Agent, or Firm* — C. Rachal Winger

(57) ABSTRACT

Provided herein are methods, compositions, and kits for preventing, inhibiting, reducing the severity of, or treating a disease or condition. A pharmaceutical composition provided herein can comprise a nucleic acid sequence encoding an antigen fused to an immune cell product, e.g., MIP-3α, and an adjuvant. The antigen can be from a bacteria, virus, fungus, parasite, or cancer. The antigen can be an Alzheimer's disease antigen.

2 Claims, 22 Drawing Sheets

(56) References Cited

OTHER PUBLICATIONS

Movsesyan, et al. Reducing AD-like pathology in 3xTg-AD mouse model by DNA epitope vaccine—a novel immunotherapeutic strategy. PLoS One. May 7, 2008;3(5):e2124.

Nukuzuma, et al. Enhancing effect of vaxfectin on the ability of a Japanese encephalitis DNA vaccine to induce neutralizing antibody in mice. Viral Immunol. 2003;16(2):183-9.

Pan, et al. Use of Vaxfectin adjuvant with DNA vaccine encoding the measles virus hemagglutinin and fusion proteins protects juvenile and infant *Rhesus macaques* against measles virus. Clin Vaccine Immunol. Aug. 2008;15(8):1214-21. Epub Jun. 4, 2008.

Reyes, et al. Vaxfectin enhances antigen specific antibody titers and maintains Th1 type immune responses to plasmid DNA immunization. Vaccine. Jun. 14, 2001;19(27):3778-86.

Romano, et al. Priming but not boosting with plasmid DNA encoding mycolyltransferase Ag85A from *Mycobacterium tuberculosis* increases the survival time of *Mycobacterium bovis* BCG vaccinated mice against low dose intravenous challenge with *M. tuberculosis* H37Rv. Vaccine. Apr. 12, 2006;24(16):3353-64. Epub Feb. 6, 2006.

Ruffini

Construct of malaria DNA vaccine candidate pMCSP

Leader sequence — MIP-3α — Spacer — CSP — myc tag

*P. yoelii* CSP

MKKCTILVVASLLLVDSLLPGYGQQKSVQA

Figure 20

Sequence of synthesized Plasmodium falciparum vaccine construct
(DNA segments followed by corresponding amino acid segment sequence)

```
ctgcagtcaccgtcgtcgacagagctgagatcctacaggagtccagggctggagagaaaac
 C  S  H  R  R  R  Q  S  -  D  P  T  G  V  Q  G  W  R  E  N
ctctgcgaggaaaaggaaggagcaagccgtgaatttaagggacgctgtgaagcaatcatg
L  C  E  E  K  E  G  A  S  R  E  F  K  G  R  C  E  A  I  M
gatgcaatgaagagagggctctgctgtgtgctgctgctgtgtggagcagtcttcgtttcg
D  A  M  K  R  G  L  C  C  V  L  L  L  C  G  A  V  F  V  S
cccagcggtaccggatccgcagcaagcaactttgactgctgtcttggatacacagaccgt
P  S  G  T  G  S  A  A  S  N  F  D  C  C  L  G  Y  T  D  R
attcttcatcctaaatttattgtgggcttcacacggcagctggccaatgaaggctgtgac
I  L  H  P  K  F  I  V  G  F  T  R  Q  L  A  N  E  G  C  D
atcaatgctatcatctttcacacaaagaaaaagttgtctgtgtgcgcaaatccaaaacag
I  N  A  I  I  F  H  T  K  K  K  L  S  V  C  A  N  P  K  Q
acttgggtgaaatatattgtgcgtctcctcagtaaaaaagtcaagaacatggaattcaac
T  W  V  K  Y  I  V  R  L  L  S  K  K  V  K  N  M  E  F  N
gacgctcaggcgccgaagagtggatccatgatgcgcaagctggccatcctgtccgtgtcc
D  A  Q  A  P  K  S  G  S  M  M  R  K  L  A  I  L  S  V  S
tccttcctgttcgtggaggccctgttccaggagtaccagtgctacggctcctcctccaac
S  F  L  F  V  E  A  L  F  Q  E  Y  Q  C  Y  G  S  S  S  N
acccgcgtgctgaacgagctgaactacgacaacgccggcaccaacctgtacaacgagctg
T  R  V  L  N  E  L  N  Y  D  N  A  G  T  N  L  Y  N  E  L  (cont. next page)
```

Figure 20 (cont.)

Figure 21 hTPA-hMIP3a-pfCSP-myc DNA only

```
CTTCAGTTCAGTCCGTCCACAGACTTCAGTACTATCCTACAGGAGTCCAAGCTTGGAGAGAAAACCTCTTGTGACGAAAA
GGAAGGAAGCAAGCGTGAATTTAAGAAGCCTGTGAAGGCAATCATTGAATCGAATGAAGAGTCTAATGAAGAGTCTTGTGTGT
GCTTCTGTGTGTGGACAAGTGTTGTTGCCCAGCGTTCCCCAGCGTACTCCGAATCGCGAACAACTTCTATTCTGTCT
TGCATACACAGACCGTATTCTTCCTAAATTTATTGTGGCCTTCACAGGGCAGTTGCCCAATGAAGCTGTGA
CATCAATTCTATCATCTTCTCGACAAGAAAATGTGTCTGTGTGTCAAATCCAAAACGGACTTTGGTGAAATA
TATTGTCGGTCTCCTCAGTAAAAGTCAAGAACATG

# METHODS AND COMPOSITIONS FOR TREATING MALARIA

CROSS-REFERENCE

This application claims the benefit of U.S. Provisional Applications Nos. 61/371,923, filed Aug. 9, 2010, and 61/466,175, filed Mar. 22, 2011, which applications are incorporated herein by reference in their entireties.

STATEMENT AS TO FEDERALLY SPONSORED RESEARCH

This invention was made with the support of the United States government under Grant number R21A1073619 by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 6, 2011, is named 41707121.txt and is 71,250 bytes in size.

BACKGROUND OF THE INVENTION

Vaccines play a role in the prevention and treatment of diseases, including cancer and infections. For some conditions, e.g., malaria, few effective vaccines are available. Vaccine studies using irradiated sporozoites have demonstrated the theoretical feasibility of an effective vaccine to protect against the pre-erythrocytic stages of malaria infection. Subsequent studies have shown that the protection observed in murine model systems of malaria can involve both humoral and cell-mediated immunity, but can depend on the activity of T lymphocytes, presumably due to the need to destroy infected cells within the liver. Although interest persists in the use of irradiated sporozoites as a malaria vaccine, the feasibility of this approach remains to be established.

DNA vaccines can be used to treat a variety of conditions. DNA vaccines can target dendritic cells (DC). DCs play a role in regulating immune responses, including determining whether immunity or tolerance is generated and whether, if immunity is generated, Th1 or Th2 T cells or both are recruited to the response. The different outcomes of presentation of antigens by DC can be influenced by the progenitor cells that gave rise to a particular class of DC, by tissue localization of the DC involved in a given response, by differences in the activating stimulus, which can be reflected by what cytokines a DC produces and, of particular relevance for this proposal, by the state of maturation of the DC, as indicated by surface protein expression profile.

There is a need for the development of, and improvement of, vaccines, e.g., DNA vaccines, to treat conditions such as malaria, cancer, and Alzheimer's disease.

SUMMARY OF THE INVENTION

In general, in one aspect, a pharmaceutical composition is provided comprising a nucleic acid sequence encoding an antigen or a fragment thereof fused to macrophage inflammatory protein 3 alpha or a fragment thereof and an adjuvant. In one embodiment, the antigen or a fragment thereof is a cancer antigen. In another embodiment, the antigen or a fragment thereof is an Alzheimer's disease antigen. In another embodiment, the antigen or a fragment thereof is from a virus, bacterium, fungi, or parasite. In another embodiment, the antigen or a fragment thereof is from a parasite. In another embodiment, the parasite is *Plasmodium falciparum, Plasmodium vivax, Plasmodium ovale, Plasmodium malaria,* or *Plasmodium yoelii*. In another embodiment, the antigen or a fragment thereof is a circumsporozoite protein or fragment thereof. In another embodiment, the circumsporozoite protein or fragment thereof is from *Plasmodium falciparum*. In another embodiment, the adjuvant is a liposome. In another embodiment, the liposome comprises a commixture of (±)—N-(3-aminopropyl)-N,N-dimethyl-2,3-bis(cis-9-tetradecenyloxy)-1-propanaminium bromide (GAP-DMORIE) and 1,2-diphytanoyl-sn-glycero-3-phosphoethanolamine (DPyPE). In another embodiment, the pharmaceutical composition further comprises a regulatory T-cell inhibitor. In another embodiment, the regulatory T-cell inhibitor is an siRNA. In one embodiment, the nucleic acid sequence comprises nucleic acid sequence from FIG. 20, or a portion thereof. In another embodiment, the nucleic acid sequence comprises the nucleic acid sequence from FIG. 21, or a portion thereof. In another embodiment, the nucleic acid sequence comprises nucleic acid sequence, from FIG. 18, or a portion thereof. In another embodiment, the nucleic acid sequence comprises nucleic acid sequence from Example 14, or a portion thereof. In another embodiment, the nucleic acid sequence comprises nucleic acid sequence in Example 15, or a portion thereof. In another embodiment, the nucleic acid sequence comprises nucleic acid sequence from Example 16, or a portion thereof. In another embodiment, the nucleic acid sequence comprises nucleic acid sequence from Example 17, or a portion thereof. In another embodiment, the nucleic acid sequence comprises nucleic acid sequence from Example 18, or a portion thereof. In another embodiment, the nucleic acid sequence comprises nucleic acid sequence from Example 19, or a portion thereof. In another embodiment, the nucleic acid sequence comprises a nucleic acid sequence from Table 2, or a portion thereof.

In another embodiment, the nucleic acid sequence is a plasmid. In another embodiment, the nucleic acid sequence encodes human macrophage inflammatory protein 3 alpha or a fragment thereof.

In another aspect, a nucleic acid sequence is provided encoding a parasite antigen fused to macrophage inflammatory protein 3 alpha. In one embodiment, the parasite is *Plasmodium falciparum, Plasmodium vivax, Plasmodium ovale, Plasmodium malaria,* or *Plasmodium yoelii*. In another embodiment, the antigen is a circumsporozoite protein or fragment thereof. In another embodiment, the circumsporozoite protein or fragment thereof is from *Plasmodium falciparum*. In another embodiment, the nucleic acid sequence encodes human macrophage inflammatory protein 3 alpha or a fragment thereof.

In another aspect, a nucleic acid sequence is provided encoding a malaria antigen fused to an immune cell product. In one embodiment, the immune cell product enhances the immunological reactivity of the antigen. In another embodiment, the immune cell product targets immature dendritic cells. In another embodiment, the immune cell product is a chemokine. In another embodiment, the chemokine is macrophage inflammatory protein 3 alpha or a fragment or derivative of macrophage inflammatory protein 3 alpha. In another embodiment, the malaria antigen is from *Plasmodium falciparum, Plasmodium vivax, Plasmodium ovale, Plasmodium malaria,* or *Plasmodium yoelii*. In another embodiment, the malaria antigen is a circumsporozoite protein or fragment thereof. In another embodiment, the malaria antigen is a circumsporozoite protein or fragment thereof and the immune cell product is macrophage inflammatory protein 3 alpha protein or a fragment thereof. In another embodiment, the circumsporozoite protein or fragment thereof from *Plasmodium falciparum* and the immune cell product is macrophage inflammatory protein 3 alpha protein or a fragment thereof. In another embodiment, the nucleic acid sequence encodes a human immune cell product or a fragment thereof.

In another aspect, a pharmaceutical composition is provided comprising a nucleic acid sequence encoding a parasite antigen fused to an immune cell product and an adjuvant. In another embodiment, the immune cell product enhances the immunological reactivity of the antigen. In another embodiment, the adjuvant is a liposome. In another embodiment, the liposome comprises a commixture of GAP-DMORIE and DPyPE. In another embodiment, the immune cell product is macrophage inflammatory protein 3 alpha. In another embodiment, the parasite antigen is from *Plasmodium falciparum, Plasmodium vivax, Plasmodium ovale, Plasmodium malaria*, or *Plasmodium yoelii*. In another embodiment, the parasite antigen is circumsporozoite protein or fragment thereof. In another embodiment, the pharmaceutical composition further comprises a regulatory T-cell inhibitor. In another embodiment, the regulatory T-cell inhibitor is an siRNA. In another embodiment, the nucleic acid sequence encodes a human immune cell product or a fragment thereof.

In another aspect, a method for eliciting an immune response in a subject is provided comprising administering to the subject a pharmaceutical composition comprising a nucleic acid sequence encoding a parasite antigen or fragment thereof fused to an immune cell product. In one embodiment, the pharmaceutical composition further comprises an adjuvant. In another embodiment, the adjuvant comprises a commixture of GAP-DMORIE and DPyPE. In another embodiment, the immune cell product is macrophage inflammatory protein 3 alpha. In another embodiment, the parasite antigen is from *Plasmodium falciparum, Plasmodium vivax, Plasmodium ovale, Plasmodium malaria*, or *Plasmodium yoelii*. In another embodiment, the parasite antigen is a circumsporozoite protein or fragment thereof. In another embodiment, the method further comprises administering a regulatory T-cell inhibitor to the subject. In another embodiment, the regulatory T-cell inhibitor is an siRNA. In another embodiment, the pharmaceutical composition comprises the regulatory T-cell inhibitor. In another embodiment, the immune response prevents or reduces the likelihood of the subject developing malaria. In another embodiment, the subject is a human. In another embodiment, the subject is a non-human mammal.

In one aspect, a kit comprising a nucleic acid sequence encoding a parasite antigen fused to an immune cell product and an adjuvant. In one embodiment, the immune cell product enhances the immunological reactivity of the antigen. In another embodiment, the immune cell product is macrophage inflammatory protein 3 alpha. In another embodiment, the parasite antigen is from *Plasmodium falciparum, Plasmodium vivax, Plasmodium ovale, Plasmodium malaria*, or *Plasmodium yoelii*. In another embodiment, the parasite antigen is a circumsporozoite protein or fragment thereof. In another embodiment, the circumsporozoite protein or fragment thereof is from *Plasmodium falciparum*. In another embodiment, the kit further comprises a regulatory T-cell inhibitor. In another embodiment, the regulatory T-cell inhibitor is an siRNA.

In another aspect, a method for eliciting an immune response in a subject is provided comprising administering to the subject a pharmaceutical composition comprising a nucleic acid sequence encoding a cancer antigen or fragment thereof fused to an immune cell product. In one embodiment, the pharmaceutical composition further comprises an adjuvant. In another embodiment, the adjuvant comprises a commixture of GAP-DMORIE and DPyPE. In another embodiment, the immune cell product is a chemokine. In another embodiment, the immune cell product is macrophage inflammatory protein 3 alpha. In another embodiment, the antigen is from lung, brain, breast, prostate or colon cancer. In another embodiment, the antigen is HER2, BRCA1, prostate-specific membrane antigen (PSMA), MART-1/MelanA, prostatic serum antigen (PSA), squamous cell carcinoma antigen (SCCA), ovarian cancer antigen (OCA), pancreas cancer associated antigen (PaA), MUC-1, MUC-2, MUC-3, MUC-18, carcino-embryonic antigen (CEA), polymorphic epithelial mucin (PEM), Thomsen-Friedenreich (T) antigen, gp100, tyrosinase, TRP-1, TRP-2, NY-ESO-1, CDK-4, b-catenin, MUM-1, Caspase-8, KIAA0205, HPVE7, SART-1, SART-2, PRAME, BAGE-1, DAGE-1, RAGE-1, NAG, TAG-72, CA125, mutated p21ras, mutated p53, HPV16 E7, RCC-3.1.3, MAGE-1, MAGE-2, MAGE-3, MAGE-4, MAGE-11, GAGE-I, GAGE-6, GD2, GD3, GM2, TF, sTn, gp75, EBV-LMP 1, EBV-LMP 2, HPV-F4, HPV-F6, HPV-F7, alpha-fetoprotein (AFP), CO17-1A, GA733, gp72, p-HCG, gp43, HSP-70, p17 mel, HSP-70, gp43, HMW, HOJ-1, HOM-MEL-55, NY-COL-2, HOM-HD-397, HOM-RCC-1.14, HOM-HD-21, HOM-NSCLC-11, HOM-MEL-2.4, HOM-TES-11, melanoma gangliosides, TAG-72, prostatic acid phosphatase, protein MZ2-E, folate-binding-protein LK26, truncated epidermal growth factor receptor (EGFR), GM-2 and GD-2 gangliosides, polymorphic epithelial mucin, folate-binding protein LK26, pancreatic oncofetal antigen, cancer antigen 15-3, cancer antigen 19-9, cancer antigen 549, cancer antigen 195 or a fragment thereof. In another embodiment, the method further comprises administering a regulatory T-cell inhibitor to the subject. In another embodiment, the regulatory T-cell inhibitor is an siRNA. In another embodiment, the pharmaceutical composition comprises the regulatory T-cell inhibitor. In another embodiment, the immune response prevents or reduces the likelihood of the subject developing cancer. In another embodiment, the immune response inhibits a cancerous cell expressing the cancer antigen in said subject. In another embodiment, the immune response inhibits a pre-cancerous cell expressing the cancer antigen in said subject. In another embodiment, the subject is a human. In another embodiment, the subject is a non-human mammal.

In another aspect, a method for eliciting an immune response in a subject is provided comprising administering to the subject a pharmaceutical composition comprising a nucleic acid sequence encoding an Alzheimer's disease antigen or fragment thereof fused to an immune cell product. In one embodiment, the pharmaceutical composition further comprises an adjuvant. In another embodiment, the adjuvant comprises a commixture of GAP-DMORIE and DPyPE. In another embodiment, the immune cell product is macrophage inflammatory protein 3 alpha. In another embodiment, the antigen is A68, Aβ40, Aβ42 protein or a fragment thereof. In another embodiment, the method further comprises administering a regulatory T-cell inhibitor to the subject. In another embodiment, the regulatory T-cell inhibitor is an siRNA. In another embodiment, the pharmaceutical composition comprises the regulatory T-cell inhibitor. In another embodiment, the immune response prevents or reduces the likelihood of the subject developing an Alzheimer's disease. In another embodiment, the immune response reduces one or more symptoms associated with Alzheimer's disease in the subject.

In another embodiment, the subject is a human. In another embodiment, the subject is a non-human mammal.

In another aspect, a method for eliciting an immune response in a subject is provided comprising administering to the subject a pharmaceutical composition comprising a nucleic acid sequence encoding an antigen or fragment thereof from a virus, bacterium, fungi, or parasite fused to an immune cell product. In one embodiment, the pharmaceutical composition further comprises an adjuvant. In another embodiment, the adjuvant comprises a commixture of GAP-DMORIE and DPyPE. In another embodiment, the immune cell product is macrophage inflammatory protein 3 alpha. In another embodiment, the parasite antigen is a circumsporozoite protein or fragment thereof. In another embodiment, the method further comprises administering a regulatory T-cell inhibitor to the subject. In another embodiment, the regulatory T-cell inhibitor is an siRNA. In another embodiment, the pharmaceutical composition comprises the regulatory T-cell inhibitor. In another embodiment, the immune response prevents or reduces the likelihood of the subject developing an infection from a virus, bacterium, fungi, or parasite. In another embodiment, the immune response treats an infection from a virus, bacterium, fungi, or parasite in the subject. In another embodiment, the subject is a human. In another embodiment, the subject is a non-human mammal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 discloses SEQ ID NO: 52.

FIG. 15 discloses SEQ ID NO: 52.

FIG. 18 discloses SEQ ID NO: 53.

FIG. 20 illustrates sequence of synthesized *Plasmodium falciparum* vaccine construct. FIG. 20 discloses the DNA sequence as SEQ ID NO: 31 and the peptide sequences as SEQ ID NOS 54-56, respectively, in order of appearance.

FIG. 21 illustrates hTPA-hMIP3a-pfCSP-myc DNA sequence. FIG. 21 discloses SEQ ID NO: 31.

DETAILED DESCRIPTION OF THE INVENTION

I. Overview

Compositions

Figure 1:
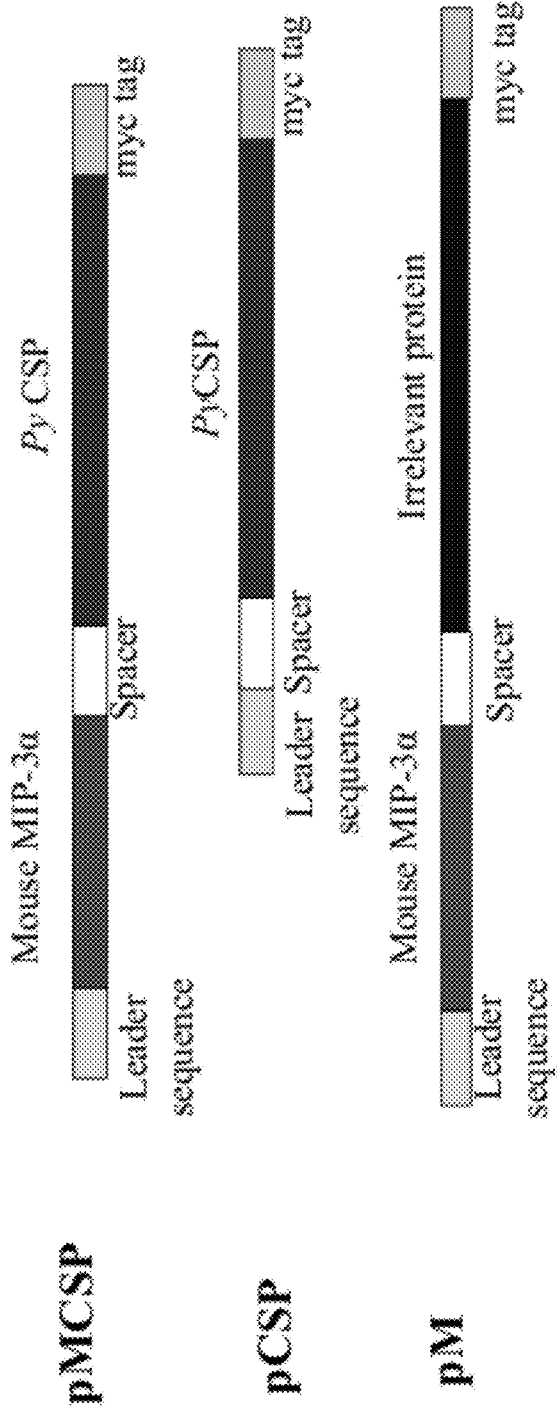
FIG. 1 illustrates constructs of a *P. yoelli* malaria DNA vaccine candidate and controls for mouse studies.

In general, in one aspect, a nucleic acid sequence is provided encoding an antigen fused to an immune cell product. In another aspect, a pharmaceutical composition is provided comprising a nucleic acid sequence encoding an antigen fused to an immune cell product. In another embodiment, the pharmaceutical composition further comprises an adjuvant. In another embodiment, the adjuvant is a liposome. In another embodiment, the liposome comprises a cationic lipid and a neutral phospholipid. In another embodiment, the cationic lipid is GAP-DMORIE. In another embodiment, the neutral phospholipid is DPyPE. In another embodiment, the adjuvant is Vaxfectin.

In one embodiment a pharmaceutical composition comprising a nucleic acid expressing an antigen (e.g., a malaria or cancer antigen) fused to an immune cell product (e.g., MIP-3α) and an adjuvant (e.g., a liposome, such as a liposome comprising GAP-DMORIE and DPyPE) produces a synergistic immunological response when administered to a subject in need thereof. In one embodiment the synergistic immunological response is directed to the antigen or a cell expressing the antigen. In another embodiment a subject is administered a pharmaceutical composition comprising a nucleic acid expressing an antigen (e.g., a malaria or cancer antigen) fused to an immune cell product (e.g., MIP-3α) and an adjuvant (e.g., a liposome, such as a liposome comprising GAP-DMORIE and DPyPE) produces a synergistic immunological response in the subject that results in a greater immunological response to the antigen. In one embodiment the synergy prevents infection of the subject by a parasite, bacteria, virus or cancer comprising the antigen. In another embodiment, administration of a pharmaceutical composition comprising a nucleic acid expressing an antigen (e.g., a malaria or cancer antigen) fused to an immune cell product (e.g., MIP-3α) and an adjuvant (e.g., a liposome, such as a liposome comprising GAP-DMORIE and DPyPE) to a subject produces an immunological response that is greater than the addition of immunological responses observed from the administration to a subject of the adjuvant with nucleic acid sequence (e.g., DNA) encoding the antigen alone, or a fusion nucleic acid sequence (e.g., DNA) vaccine expressing a chemokine, but without the adjuvant.

In one embodiment, the immune cell product is a cytokine. In another embodiment, the cytokine is a chemokine. In another embodiment, the chemokine is a CC chemokine family member. In another embodiment, the chemokine is macrophage inflammatory protein 3 alpha (MIP-3 α).

In another embodiment, the antigen is a cancer antigen, an Alzheimer's disease antigen, or an antigen from a bacterium, virus, fungus, or a parasite. In one embodiment, the antigen is from a species of *Plasmodium*. In another embodiment, the antigen is a malaria antigen. In another embodiment, the antigen from a species of *Plasmodium* is a malaria antigen. In another embodiment, the antigen is circumsporozoite protein or fragment thereof. In another embodiment, the circumsporozoite protein or protein fragment is from *Plasmodium falciparum*.

The term "fragment" or "protein fragment" can be a polypeptide that contains, for example between about 1 and 2000, 1 and 1950, 1 and 1900, 1 and 1850, 1 and 1800, 1 and 1750, 1 and 1700, 1 and 1650, 1 and 1600, 1 and 1550, 1 and 1500, 1 and 1450, 1 and 1400, 1 and 1350, 1 and 1300, 1 and 1250, 1 and 1200, 1 and 1150, 1 and 1100, 1 and 1050, 1 and 1000, 1 and 950, 1 and 900, 1 and 850, 1 and 800, 1 and 750, 1 and 700, 1 and 650, 1 and 600, 1 and 550, 1 and 500, 1 and 450, 1 and 400, 1 and 350, 1 and 300, 1 and 250, 1 and 200, 1 and 150, 1 and 100, or 1 and 50 contiguous amino acids, including all integers in between, of a reference polypeptide sequence. A fragment can be a polypeptide that contains, for example: about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, or more contiguous amino acids, including all integers in between, of a reference polypeptide sequence.

In one embodiment, provided herein is a nucleic acid sequence encoding protein or protein fragment from *Plasmodium* malaria antigen fused to a chemokine. In one embodiment the chemokine is a CC chemokine family member. In one embodiment the CC chemokine family member is MIP-3α. In another embodiment the nucleic acid sequence is provided with an adjuvant. In another embodiment, the adjuvant is a liposome. In another embodiment, the liposome comprises a cationic lipid and a neutral phospholipid. In another embodiment, the cationic lipid is GAP-DMORIE. In another embodiment, the neutral phospholipid is DPyPE. In another embodiment, the adjuvant is Vaxfectin.

In another embodiment, provided herein is a nucleic acid sequence encoding circumsporozoite protein or protein fragment from *Plasmodium falciparum* fused to MIP-3α. In one embodiment, provided herein is a pharmaceutical composition comprising a nucleic acid sequence encoding circumsporozoite protein or protein fragment from *Plasmodium falciparum* fused to MIP-3α, and Vaxfectin. The nucleic acid sequence encoding CSP and encoding MIP-3α can be separated by spacer nucleic acid sequence. The protection against malaria provided by administration of this combination can be synergistic and exceed the sum of protection attained by using either the adjuvant with nucleic acid sequence (e.g., DNA) encoding the parasite antigen alone or a fusion nucleic acid sequence (e.g., DNA) vaccine with the chemokine, but without the adjuvant.

In one embodiment, a malaria DNA vaccine is provided comprising DNA encoding a malaria antigen fused to DNA encoding an immune cell product that enhances immunological reactivity of the antigen. The DNA fusion product can be administered with an adjuvant, e.g., a commercially available DNA vaccine adjuvant. In one embodiment, the combination of the antigen construct and the adjuvant can elicit a protective immune response in a mammal that is equivalent to, substantially similar to, or greater than the response elicited by irradiated sporozoites. In one embodiment the mammal is a human. In another embodiment the mammal is a non-human animal (e.g., a mouse, monkey, ape, dog, horse, cow, or deer). In another embodiment the combination of the antigen construct and the adjuvant can elicit a protective immune response in mice that is equivalent to, substantially similar to, or greater than the response elicited by an antigen alone, e.g., irradiated sporozoites. In one embodiment this protective response can be elicited in a mouse strain that is known to be poorly responsive to malaria vaccines.

Methods

In another aspect, provided herein is a method for eliciting an immune response in a subject comprising administering to the subject a pharmaceutical composition comprising a nucleic acid sequence encoding an antigen fused to an immune cell product. In one embodiment the subject is a mammal. In one embodiment the mammal is a human. In another embodiment the mammal is a non-human mammal. In one embodiment, the pharmaceutical composition further comprises an adjuvant. In another embodiment, administering to a subject a pharmaceutical composition comprising a nucleic acid sequence expressing an antigen, e.g., a malaria antigen or cancer antigen, fused to an immune cell product, e.g., MIP-3α, and an adjuvant, e.g., a liposome comprising GAP-DMORIE and DPyPE, elicits a protective immune response that is equivalent to, substantially similar to, or greater than the response elicited by irradiated sporozoites.

In another aspect, provided herein is a method for preventing a disease comprising administering to the subject a pharmaceutical composition comprising a nucleic acid sequence encoding an antigen fused to an immune cell product. In one embodiment, the pharmaceutical composition further comprises an adjuvant. In another embodiment, the disease is cancer, Alzheimer's disease, a bacterial infection, a fungal infection, a viral infection, or a parasitic infection. In another embodiment, the disease is malaria.

Additional aspects and embodiments are described below.

II. Nucleic Acid Sequence

A. Immune Cell Product and Molecules that Target Dendritic Cells

In one embodiment, a nucleic acid sequence is provided comprising a sequence that encodes an antigen fused to an immune cell product. In one embodiment, the immune cell product enhances the immunological reactivity of the antigen. In one embodiment, the immune cell product is a human immune cell product. In another embodiment, the immune cell product is a cytokine, or a fragment thereof. In another embodiment, the immune cell product is a chemokine, or a fragment thereof. In another embodiment, the immune cell product can target (e.g., bind) a dendritic cell. In another embodiment, the immune cell product can bind a receptor on a dendritic cell. In another embodiment, the immune cell product can bind a chemokine receptor on a dendritic cell. In one embodiment, the chemokine receptor is CCR1, CCR2, CCR5, CCR6, or CXCR1. In one embodiment, the dendritic cell is an immature dendritic cell. In one embodiment, the chemokine is CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXC12, CXCL13, CXCL14, CXCL15, CXCL16, CXCL17, XCL1, XCL2, or CX3CL1, or a fragment or mimic thereof of any of these chemokines. In one embodiment, the chemokine is a human chemokine. In one embodiment, the chemokine fragment or mimic thereof retains the ability to bind to a chemokine receptor.

In another embodiment, a nucleic acid sequence is provided comprising a sequence that encodes an antigen fused to molecule that targets (e.g., binds) a dendritic cell. In one embodiment, the molecule that targets a dendritic cell can bind a Toll-like receptor (TLR). In another embodiment, the molecule that targets a dendritic cell binds a chemokine receptor. In another embodiment, the molecule that targets a dendritic cell is a chemokine. In another embodiment, the molecule that targets a dendritic cell is a human beta-defensin-2.

1. Cytokines

In one embodiment, the immune cell product is a cytokine, or a fragment thereof. A cytokine can be a small cell-signaling molecule (e.g., a protein or peptide) secreted by a cell of the immune system that can be used in intercellular communication. Cytokines can act at nano-picomolar concentrations to modulate the activities of cells and tissues. They can mediate interactions between cells and regulate extracellular processes. A cytokine can be, e.g., a lymphokine, interleukin, or a chemokine. A cytokine can be, e.g., a monokine, interferon (IFN), or a colony stimulating factor (CSF). The cytokine can be a cytokine from a mammal, e.g., a human, mouse, cow, horse, camel, gorilla, chimpanzee, rabbit, pig, dog, cat, camel, rat, elephant, deer, rhinoceros, bear, weasel, seal, whale, dolphin, porpoise, bat, shrew, mole, hedgehog, squirrel, chipmunk, gopher, monkey, lemur, anteater, sloth, armadillo, manatee, sea cow, or aardvark.

In one embodiment, the cytokine is a lymphokine. A lymphokine can be a protein produced by a lymphocyte, a type of white blood cell, e.g., a T cell. Lymphokines can function to attract immune cells, such as macrophages or other lymphocytes, to a site of infection. Examples of lymphokines include, e.g., interleukins (e.g., IL-1 alpha, IL-1 beta, IL-2, IL-3, IL-4, IL-5, IL-6 (BSF-2), IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 or IL-35). Interleukins can be synthesized by helper CD4+ T lymphocytes, monocytes, macrophages, and endothelial cells. A lymphokine can be a colony-stimulating factor (CSF). A CSF can be a secreted glycoprotein that can bind to a receptor on the surface of a hemopoietic stem cell. CSFs include CSF1, CSF2, and CSF3.

In one embodiment, the immune cell product is a chemokine. In one embodiment, the immune cell product is a fragment of a chemokine. Examples of chemokines are provided, e.g., in Amanda Proudfoot. The chemokine family. Potential targets from allergy to HIV infection. *European Journal of Dermatology* vol. 8, pp 147-157 (1998). A chemokine can induce chemotaxis in a nearby responsive cell. Chemokines can direct lymphocytes to lymph nodes. In one embodiment, the chemokine is CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXC12, CXCL13, CXCL14, CXCL15, CXCL16, CXCL17, XCL1, XCL2, or CX3CL1, or fragment of any of these chemokines.

Chemokines can be characterized as inflammatory (inducible) or homeostatic (constitutive), based on their pathophysiological activities. Inflammatory chemokines can be expressed during infection or tissue damage by resident and infiltrating leukocytes. In contrast, homeostatic chemokines can be produced constitutively in discrete microenvironments, and they can be involved in maintaining the physiological trafficking of immune cells.

Chemokines can be small proteins with a molecular mass of between about 8 to 10 kDa. One feature of many chemokines is four cysteines that form intramolecular disulphide bonds and affect the three dimensional shape of the chemokine. Chemokines can be classified into one of four different chemokine families based on the number and positioning of cysteines in the chemokine. A first family is the CC chemokine family. Members of the CC chemokine family have two adjacent cysteines near their amino terminus. CC chemokine family members include, e.g., CC chemokine ligands (CCL) 1 to 28. A second family is CXC chemokine family. Members of the CXC chemokine family have two N-terminal cysteines separated by one amino acid. CXC chemokines include CXCL1-17. A third family is the C chemokines. C chemokines have only two cysteines. Examples of C chemokines include XCL1 and XCL2. A fourth family is the CXXXC, or $CX_3C$, family. CX3CL1 is an example of a member of the $CX_3C$ family.

2. Dendritic Cell Targeting

In another embodiment, the immune cell product targets, e.g., binds, a dendritic cell (DC), e.g., an immature DC. A DC is an immune cell that can process antigen material and present the material on the surface of the dendritic cell to T and B lymphocytes. Thus, a DC can be an antigen presenting cell. DCs can be found in peripheral tissues, e.g., on the skin and in the inner linking of the stomach, intestines, nose, and lungs. For example, Langerhans cells are dendritic cells found in the epidermis.

Dendritic cells can include myeloid dendritic cells (mDC) and plasmacytoid dendritic cells (pDC). Myeloid dendritic cells can include mDC-1, which can stimulate T cells, and mDC-2, which can function in fighting wound infection. mDCs can secrete IL-12 and can express Toll-like receptors TLR-1, TLR-2, TLR-3, TLR-4, TLR-5, TLR-6, TLR-8, and/or TLR-11. Plasmacytoid dendritic cells can produce interferon-alpha and have Toll-like receptors TLR 7 and TLR 9. TLRs and dendritic cells are reviewed, e.g., in Liu, Ko-Jiunn. Dendritic Cell, Toll-Like Receptor, and The Immune System http://www.mupnet.com/JOCM %202(6)%20213-215.pdf.

Immature dendritic cells (iDCs) can be generated from hemopoietic bone marrow progenitor cells. Immature DCs can exist in the peripheral tissues and in secondary lymph nodes. An iDC can have well-developed endocytic function and low levels of expression of MHC Class I and II molecules. An iDC can have low T cell activation potential.

An iDC can survey the environment for pathogens such as viruses and bacteria using pattern recognition receptors (PRRs), e.g., Toll-like receptors (TLRs). A Toll-like receptor is a single membrane spanning receptor that can recognize structurally conserved regions on microbes.

An iDC can take up antigen through fluid-phase endocytosis. An iDC can phagocytose a pathogen, degrade proteins from the pathogen, and present the fragments on the DC surface using MHC molecules. A DC can then migrate to a lymph node. An activated DC can upregulate cell-surface receptors CD80, CD86, and CD40, that can act as coreceptors in T cell activation. A mature DC can upregulate the CCR7 receptor that can induce a DC to move through the blood stream to the spleen or through the lymphatic system to a lymph node. Mature DC have decreased endocytic activity and increased surface expression of class II MHC costimulatory molecules. A migrated mature DC can present foreign antigens to naïve T cells. A T cell can be clonally expanded to effector T cells for a primary immune response. Some T cells differentiate to memory T cells for a second immune response.

Both induction and expression of T cell-mediated responses can involve close approximation of T cells and the cells that activate them or are their targets. While soluble cytokines and lymphokines play roles in these processes, they can be active at concentrations that can be achieved in close proximity to their cell of origin. Cells involved in the development of T cell immunity have evolved to establish proximity to the appropriate cell to execute effector or inductive functions. Bringing an antigen of interest into contact with the most efficient antigen-presenting cells can depend on the ability of the stimulating antigen to mobilize an inflammatory response that will attract immune cells to the site. Molecular components of viruses, bacteria, and parasites can elicit such a response.

Chemokine responsiveness and chemokine receptor expression play a role in DC recruitment to sites of inflammation and migration to lymphoid organs. Cell trafficking can be regulated by differential expression of heterotrimeric Gi protein-coupled seven-transmembrane domain chemokine receptors on DCs. For example, the receptors CCR1, CCR2, CCR5, CCR6, and CXCR1 can be expressed on iDCs. The CCR6 receptor can bind the chemokine MIP-3 α. The chemokine CCL5/RANTES can interact with the receptors CCR5 and CCR1. The chemokine CCL3/MIP-1α can interact with the CCR1, CCR4, and CCR5 receptors. Upon maturation of DC, the expression of these receptors can be down-regulated, while that of other receptors, such as CCR7, can be up-regulated.

3. CCR1 Receptor Binding

In another embodiment, the immune cell product can bind the CCR1 receptor, e.g., a CCR1 receptor of an iDC. CCR1 (also known as CKR1; CD191; CKR-1; HM145; CMKBR1; MIP1aR; SCYAR1) is a member of the beta chemokine receptor family, which can be a seven transmembrane protein similar to G protein-coupled receptors. The ligands of this receptor include macrophage inflammatory protein 1 alpha (MIP-1 alpha), regulated on activation normal T expressed and secreted protein (RANTES), monocyte chemoattractant protein 3 (MCP-3), and myeloid progenitor inhibitory factor-1 (MPIF-1). Chemokines and their receptors mediated signal transduction are critical for the recruitment of effector immune cells to the site of inflammation. Knockout studies of the mouse homolog suggested roles for CCR1 receptor in host protection from inflammatory response, and susceptibility to virus and parasite.

4. CCR2 Receptor Binding

In another embodiment, the immune cell product can bind the CCR2 receptor, e.g., a CCR2 receptor of an iDC. The CCR2 gene (also known as CKR2; CCR2A; CCR2B; CD192; CKR2A; CKR2B; CMKBR2; MCP-1-R; CC-CKR-2; FLJ78302; MGC103828; MGC111760; MGC168006) encodes two isoforms of a receptor for monocyte chemoattractant protein-1, a chemokine which specifically mediates monocyte chemotaxis. Monocyte chemoattractant protein-1 is involved in monocyte infiltration in inflammatory diseases such as rheumatoid arthritis as well as in the inflammatory response against tumors. The receptors encoded by this gene mediate agonist-dependent calcium mobilization and inhibition of adenylyl cyclase.

5. CCR5 Receptor Binding

In another embodiment, the immune cell product can bind the CCR5 receptor, e.g., a CCR5 receptor of an iDC. CCR5 (also known as CKR5; CD195; CKR-5; CCCKR5; CMKBR5; IDDM22; CC-CKR-5; FLJ78003) is a member of the beta chemokine receptor family, which can be a seven transmembrane protein similar to G protein-coupled receptors. This protein is expressed by T cells and macrophages, and is known to be a co-receptor for macrophage-tropic virus, including HIV, to enter host cells. Defective alleles of the CCR5 gene have been associated with HIV infection resistance. The ligands of this receptor include monocyte chemoattractant protein 2 (MCP-2), macrophage inflammatory protein 1 alpha (MIP-1 alpha), macrophage inflammatory protein 1 beta (MIP-1 beta) and regulated on activation normal T expressed and secreted protein (RANTES). Expression of the CCR5 gene is also detected in a promyeloblastic cell line, suggesting that this protein can play a role in granulocyte lineage proliferation and differentiation.

6. CCR6 Receptor Binding

In another embodiment, the immune cell product can bind the CCR6 receptor, e.g., a CCR6 receptor of an iDC. CCR6 (chemokine (C-C motif) receptor 6) is also known as BN-1; DCR2; DRY6; CCR-6; CD196; CKRL3; GPR29; CKR-L3; CMKBR6; GPRCY4; STRL22; CC-CKR-6; and C-C CKR-6). CCR6 is a member of the beta chemokine receptor family and is predicted to be a seven transmembrane protein, similar to G protein-coupled receptors. The CCR6 gene can be expressed by iDCs and memory T cells. CCR6 receptor can play a role in B-lineage maturation and antigen-driven B-cell differentiation, and it can regulate the migration and recruitment of dendritic and T cells during inflammatory and immunological responses. Human β-defensin 2, an antimicrobial peptide involved in innate immunity against infection, can bind to the chemokine CCR6. The CCR6 receptor can bind the chemokine MIP-3α.

7. CXCR1 Receptor Binding

In another embodiment, the immune cell product can bind the CXCR1 receptor, e.g., a CCR6 receptor of an iDC. CXCR1 (chemokine (C-X-C motif) receptor 1, also known as C-C; CD128; CD181; CKR-1; IL8R1; IL8RA; CMKAR1; IL8RBA; CDw128a; C-C-CKR-1) is a member of the G-protein-coupled receptor family. This protein can be a receptor for interleukin 8 (IL8). CXCR1 can bind to IL8 with high affinity, and can transduce the signal through a G-protein activated second messenger system. Knockout studies in mice suggested that this protein inhibits embryonic oligodendrocyte precursor migration in developing spinal cord.

8. Defensins

In another embodiment, a nucleic acid sequence is provided comprising a sequence that encodes an antigen fused to a defensin. In another embodiment, a nucleic acid sequence is provided comprising a sequence that encodes an antigen fused to human β-defensin 2. In another embodiment, the immune cell product that can bind the CCR6 receptor is human beta-defensin-2 (also known as DEFB4A, BD-2, SAP1, DEFB2, HBD-2, DEFB-2, BEFB102). In another embodiment, the immune cell product is a fragment of human beta-defensin-2. DEFB4A is a cysteine-rich cationic low molecular weight antimicrobial peptide. It can be produced by epithelial cells and can exhibit potent antimicrobial activity against Gram-negative bacteria and *Candida*. DEFB4A can be produced following stimulation of epithelial cells by contacting microorganisms such as *Pseudomonas aeruginosa* or cytokines such as TNF-alpha and IL-1 beta. The DEFB4A gene and protein can be locally expressed in keratinocytes associated with inflammatory skin lesions such as psoriasis as well as in the infected lung epithelia of patients with cystic fibrosis. DEFB4A can interact with the CCR6 receptor. Nucleic acid sequence and protein sequence for DEFB4A are provided in Table 2.

In another embodiment, a nucleic acid sequence is provided comprising a sequence that encodes an antigen fused to murine beta-defensin 2. Murine beta-defensin 2 is also known as BD-2; MGC129140; MGC129141. Nucleic acid sequence and protein sequence for murine beta-defensin 2 are provided in Table 2.

In another embodiment, a nucleic acid sequence is provided comprising a sequence encoding an antigen fused to human beta defensin 3. The nucleic acid sequence and protein sequence for human beta defensin 3 can be found in Table 2.

9. MIP-3α (CCL20)

In another embodiment, the immune cell product is macrophage inflammatory 3-alpha (MIP-3α). In another embodiment, the immune cell product is a fragment of MIP-3α. MIP-3α can be a ligand of CCR6 receptor. MIP-3α (also known as CCL20 (chemokine (C-C motif) ligand 20), Ckb4, LARC (liver activation regulated chemokine), ST38, or SCYA20) is a cytokine that belongs to the CC chemokine family. MIP-3α can be chemotactic for lymphocytes and can attract neutrophils. MIP-3α can be involved in the function of mucosal lymphoid tissues by chemoattraction of lymphocytes and dendritic cells towards epithelial cells surrounding these tissues. MIP-3α can elicit its effects on target cells by binding and activating the chemokine receptor CCR6. In another embodiment, the immune cell product is a fragment MIP-3α. Nucleic sequence and protein sequence for MIP-3α are provided in Table 2.

By fusing the chemokine MIP-3α to the antigens of interest, iDC can be attracted to the site of antigen deposition and also ensure efficient uptake of antigen by the CCR6-bearing iDC that play a role in the initiation of immune responses. MIP-3α can attract immature Langerhans cells to dermal sites. GM-CSF can down-regulate expression of CCR6 on Langerhans cells, potentially interfering with their ability to initiate the optimal immune response. Interruption of CCR6 engagement can preclude the development of CD8+ T cell-mediated cytotoxic activity. By increasing the efficiency of both recruitment of iDC to the inoculation site and the uptake of antigen by those recruited iDC, the number of antigen-presenting cells that mature after antigen-uptake and migrate to sites of T cell activation can be expanded.

10. CCL5/RANTES

In another embodiment, the immune cell product is CCL5 (chemokine (C-C motif) ligand 5). CCL5 is also known as SISd; SCYA5; RANTES; TCP228; D17S136E; MGC17164. CCL5 is a CC cytokine. Cytokines are a family of secreted proteins involved in immunoregulatory and inflammatory processes. The CC cytokines are proteins characterized by two adjacent cysteines. CCL5 functions as a chemoattractant for blood monocytes, memory T helper cells and eosinophils. It causes the release of histamine from basophils and activates eosinophils. This cytokine is one of the major HIV-suppressive factors produced by CD8+ cells. CCL5 can function as one of the natural ligands for the chemokine receptor CCR5 and it can suppress in vitro replication of the R5 strains of HIV-1, which can use CCR5 as a coreceptor. Nucleic sequence and protein sequence for MIP-3α are provided in Table 2.

11. CCL3

In another embodiment, the immune cell product is CCL3 (chemokine (C-C motif) ligand 3). CCL3 is also known as MIP1A; SCYA3; GOS19-1; LD78ALPHA; MIP-1-alpha. CCL3 is an inducible cytokine. CCL3, also known as macrophage inflammatory protein 1 alpha, plays a role in inflammatory responses through binding to the receptors CCR1, CCR4 and CCR5. Polymorphisms at this locus can be associated with both resistance and susceptibility to infection by human immunodeficiency virus type. Nucleic sequence and protein sequence for CCL3 are provided in Table 2.

12. IL8

In another embodiment, the immune cell product is IL8 (interleukin 8). IL8 is also known as NAF; GCP1; LECT; LUCT; NAP1; CXCL8; GCP-1; LYNAP; MDNCF; MONAP; NAP-1. IL8 is a member of the CXC chemokine family. This chemokine is a mediator of the inflammatory response. This chemokine is secreted by several cell types. IL8 can function as a chemoattractant and an angiogenic factor. IL8 is believed to play a role in the pathogenesis of bronchiolitis, a common respiratory tract disease caused by viral infection.

13. CCL7

In another embodiment, the immune cell product is CCL7 (chemokine (C-C motif) ligand 7). CCL7 is also known as FIC; MARC; MCP3; NC28; MCP-3; SCYA6; SCYA7; MGC138463; MGC138465. CCL7, also known as monocyte chemotactic protein 3, is a secreted chemokine that can attract macrophages during inflammation and metastasis. It is a member of the C-C subfamily of chemokines which are characterized by having two adjacent cysteine residues. The protein can be an in vivo substrate of matrix metalloproteinase 2, an enzyme that can degrade components of the extracellular matrix.

14. CCL2

In another embodiment, the immune cell product is CCL2 (chemokine (C-C motif) ligand 2). CCL2 is also known as HC11; MCAF; MCP1; MCP-1; SCYA2; GDCF-2; SMC-CF; HSMCR30; MGC9434. CCL2 is structurally related to the CXC subfamily of cytokines. Members of this subfamily are characterized by two cysteines separated by a single amino acid. This cytokine displays chemotactic activity for monocytes and basophils but not for neutrophils or eosinophils. CCL2 has been implicated in the pathogenesis of diseases characterized by monocytic infiltrates, like psoriasis, rheumatoid arthritis and atherosclerosis. CCL2 can bind to chemokine receptors CCR2 and CCR4.

15. CCL23

In another embodiment, the immune cell product is CCL23 (chemokine (C-C motif) ligand 23). CCL23 is also known as CKb8; MIP3; Ckb-8; MIP-3; MPIF-1; SCYA23; Ckb-8-1; CK-BETA-8. CCL23 displays chemotactic activity on resting T lymphocytes and monocytes, lower activity on neutrophils and no activity on activated T lymphocytes. The protein is also a strong suppressor of colony formation by a multipotential hematopoietic progenitor cell line. CCL23 is an agonist at CC chemokine receptor 1.

16. CCL8

In another embodiment, the immune cell product is CCL8 (chemokine (C-C motif) ligand 8). CCL8 is also known as CKb8; MIP3; Ckb-8; MIP-3; MPIF-1; SCYA23; Ckb-8-1; CK-BETA-8. CCL8 is a member of the CXC subfamily of cytokines. Members of this subfamily are characterized by two cysteines separated by a single amino acid. This cytokine displays chemotactic activity for monocytes, lymphocytes, basophils and eosinophils. By recruiting leukocytes to sites of inflammation this cytokine can contribute to tumor-associated leukocyte infiltration.

17. CCL4

In another embodiment, the immune cell product is CCL4 (chemokine (C-C motif) ligand 4). CCL4 is also known as ACT2; G-26; LAG1; MIP1B; SCYA2; SCYA4; MIP1B1; AT744.1; MGC104418; MGC126025; MGC126026; MIP-1-beta. CCL4, also known as Macrophage inflammatory protein-iβ (MIP-1β) is a CC chemokine with specificity for CCR5 receptors. It can be a chemoattractant for natural killer cells, monocytes and a variety of other immune cells. CCL4 is a HIV-suppressive factor produced by CD8+ T cells.

18. CCL22

In another embodiment, the immune cell product is CCL22 (chemokine (C-C motif) ligand 22. CCL22 is also known as MDC; ABCD-1; SCYA22; STCP-1; DC/B-CK; MGC34554; or A-152E5.1. MDC; ABCD-1; SCYA22; STCP-1; DC/B-CK; MGC34554; A-152E5.1 CCL22 is a CC family member; the CC cytokines are proteins characterized by two adjacent cysteines. CCL22 displays chemotactic activity for monocytes, dendritic cells, natural killer cells and for chronically activated T lymphocytes. It also displays a mild activity for primary activated T lymphocytes. CCL22 can bind to chemokine receptor CCR4. This chemokine can play a role in the trafficking of activated T lymphocytes to inflammatory sites and other aspects of activated T lymphocyte physiology.

19. CXCL2

In another embodiment, the immune cell product is CXCL2 (chemokine (C-X-C motif) ligand 2. CXCL2 is also known as GRO2; GROb; MIP2; MIP2A; SCYB2; MGSA-b; MIP-2a; or CINC-2a.

In one embodiment, a nucleic acid sequence is provided comprising a sequence that encodes an antigen fused to a cytokine. In one embodiment, a nucleic acid sequence is provided comprising a sequence that encodes an antigen fused to a chemokine. In one embodiment, a nucleic acid sequence is provided comprising a sequence that encodes an antigen fused to an immune cell product that targets an immature dendritic cell. In one embodiment, a nucleic acid sequence is provided comprising a sequence that encodes an antigen fused to an immune cell product that targets CCR6 receptor. In one embodiment, a nucleic acid sequence is provided comprising a sequence that encodes an antigen fused to MIP-3α.

B. Antigen

1. Parasite Antigen

In one embodiment, a nucleic acid sequence is provided comprising a sequence that encodes a parasite antigen fused to an immune cell product, e.g., MIP-3α or a fragment or mimic thereof. In one embodiment, a nucleic acid is provided comprising a sequence that encodes a parasite antigen fused to a ligand for a receptor on a dendritic cell, e.g., MIP-3α or a fragment or mimic thereof. In one embodiment, the parasite antigen is from the parasite *Acanthamoeba, African trypanosomiasis, Echinococcus granulosus, Echinococcus multilocularis, Entamoeba histolytica, Trypanosoma cruzi, Ascaris lumbricoides, Angiostrongylus cantonensis,* anisakid nematode, *Babesia microti, Balantidium coli, Cimex lectularius, Balamuthia mandrillaris, Baylisascaris, Schistosoma mansoni, S. haematobium, S. japonicum, Schistosoma masoni, Schistosoma intercalatum, B. hominis,* body lice, *Capillaria hepatica, Capillaria philippinensis, Austrobilharzia variglandis, Chilomastix mesnili, Endolimax nana, Entamoeba coli, Entamoeba dispar, Entamoeba hartmanni, Entamoeba polecki, Iodamoeba buetschlii, C. sinensis, Ancylostoma brazilense, A. caninum, A. ceylanicum, Uncinaria stenocephala,* lice, *Cryptosporidium, Cyclospora cayetanensis, Taenia, Cystoisospora belli, Dientamoeba fragilis, Diphyllobothrium latum, Dipylidium caninum, Dracunculus medinensis, Giardia intestinalis,* Brugia malayi, *Entamoeba histolytica, Enterobius vermicularis, Fasciola hepatica, Fasciola gigantica, Fasciolopsis buski, Toxoplasma gondii, Trichinella spiralis, Giardia lamblia, Giardia duodenalis, Gnathostoma spinigerum, Heterophyes heterophyes, Hymenolepis nana, Leishmania promastigotes, Pediculus humanus capitis, Pediculus humanus corporis, Pthirus pubis, Loa loa, Plasmodium vivax, Plasmodium ovale, Plasmodium falciparum, Plasmodium malariae, Plasmodium yoelii, Plasmodium bubalis, Plasmodium juxtanucleare, Plasmodium circumflexum, Plasmodium relictum, Plasmodium relictum, Plasmodium vaughani, Plasmodium minasense, Plasmodium agamae, Plasmodium dominicum, Brachiola algerae, B. connori, B. vesicularum, Encephalitozoon cuniculi, E. hellem, E. intestinalis, Enterocytozoon bieneusi Microsporidium ceylonensis, M. africanum, Nosema ocularum, Pleistophora* sp., *Trachipleistophora hominis, T. anthropophthera, Vittaforma corneae, Sarcoptes scabiei* var. *hominis, Dermatobia homi-* nis, *Naegleria fowleri, Toxocara canis, Toxocara cati, Onchocerca volvulus, Opisthorchis felineus, Paragonimus westermani, Pneumocystis jirovecii, Sappinia diploidea, Sappinia pedata, Trypanosoma brucei, Trichuris trichiura, Ascaris lumbricoides, Anclostoma duodenale, Necator americanus, Strongyloides stercoralis, Strongyloides fiilleborni, Capillaria philippinensis, Taenia saginata, Taenia solium, Taenia asiatica, Toxoplasma gondii, Trichinella,* or *Trichomonas vaginalis.* In one embodiment, the antigen is from a *Plasmodium* species. In one embodiment, the antigen is from *Plasmodium falciparum.*

In one embodiment, the antigen is a malaria antigen. The malaria antigen can be from a species of *Plasmodium.* The *Plasmodium* species can be, e.g., *Plasmodium vivax, Plasmodium ovale, Plasmodium falciparum, Plasmodium malariae, Plasmodium yoelii, Plasmodium bubalis, Plasmodium juxtanucleare, Plasmodium circumflexum, Plasmodium relictum, Plasmodium relictum, Plasmodium vaughani, Plasmodium minasense, Plasmodium agamae,* or *Plasmodium dominicum.*

The malaria antigen can be an antigen that is expressed during one or more stages of a *Plasmodium* life cycle. The *Plasmodium* life cycle is described, e.g., at http://dpd.cdc.gov/DPDx/HTML/Malaria.htm. A *Plasmodium* life cycle can involve two hosts. During a blood meal, a *Plasmodium* infected female *Anopheles* mosquito can inoculate sporozoites into the human host. Sporozoites can infect liver cells and mature into schizonts, which can rupture and release merozoites. In *P. vivax* and *P. ovale,* a dormant stage (hypnozoites) can persist in the liver and cause relapses by invading the bloodstream weeks, or even years later. After this initial replication in the liver (exo-erythrocytic schizogony), the parasites undergo asexual multiplication in the erythrocytes (erythrocytic schizogony). Meroziotes infect red blood cells. The ring stage trophozoites mature into schizonts, which rupture releasing merozoites. Some parasites differentiate into sexual erythrocytic stages (gametocytes). Blood stage parasites are responsible for clinical manifestations of malaria.

The gametocytes, male (microgametocyes) and female (macrogametocytes), are ingested by an *Anopheles* mosquito during a blood meal. The parasites' multiplication in the mosquito is called the sporogonic cycle. While in the mosquito's stomach, the microgametes can penetrate the macrogametes generating zygotes. The zygotes in turn become motile and elongated (ookinetes) which invade the midgut wall of the mosquito where they develop into oocysts. The oocysts grow, rupture, and release sporozoites, which make their way to the mosquito's salivary glands. Inoculation of the sporozoites into a new human host perpetuates the malaria life cycle.

The malaria antigen can be, e.g., circumsporozoite (CSP) protein or protein fragment, liver stage antigen-1 (LSA-1), erythrocyte binding antigen (EBA-175), merozoite surface antigen 1 & 2 (MSA-1 & 2), ring infected erythrocyte surface antigen (RESA), serine repeat antigen (SERA), rhoptry associated protein 1 (RAP1) and 2 (RAP2), histidine rich protein 2 (HRP), apical membrane antigen-1 (APM-1), Pfs 25, 48/45k, or Pfs 230. The malaria antigen can be a fragment of any of these antigens. The malaria antigen can be a fusion of all or part of one or more of these antigens.

The malaria antigen from the species *Plasmodium vivax, Plasmodium ovale, Plasmodium falciparum, Plasmodium malariae, Plasmodium yoelii, Plasmodium bubalis, Plasmodium juxtanucleare, Plasmodium circumflexum, Plasmodium relictum, Plasmodium relictum, Plasmodium vaughani, Plasmodium minasense, Plasmodium agamae,* or *Plasmodium dominicum.* In one embodiment, the malaria antigen is circumsporozoite protein or protein fragment. In another embodiment, the malaria antigen is circumsporozoite protein or protein fragment from *Plasmodium falciparum.*

In one embodiment, a nucleic acid sequence is provided comprising a sequence encoding circumsporozoite protein or protein fragment from *Plasmodium falciparum* fused to MIP-3α.

2. Cancer Antigen

In one embodiment, a nucleic acid sequence is provided comprising a sequence that encodes a cancer antigen or a fragment thereof fused to an immune cell product, e.g., MIP-3α or a fragment or mimic thereof. In one embodiment, a nucleic acid sequence is provided comprising a sequence that encodes a cancer antigen or a fragment thereof fused to a ligand for a receptor on a dendritic cell, e.g., MIP-3α or a fragment or mimic thereof. The cancer can be, e.g., acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenström's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sézary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer; thymic malignancies, including thyroid carcinoma, nodule evaluation, papillary carcinoma, follicular carcinoma, Hürthle cell neoplasm, medullary carcinoma, and anaplastic carcinoma; or uterine neoplasms, including endometrial cancer and uterine sarcoma.

The cancer antigen or a fragment thereof can be a tumor antigen or a fragment thereof listed in, e.g., U.S. Patent Application No. 20080044418 or a cancer antigen listed in U.S. Patent Application No. 20090074800, which are hereby incorporated by reference in their entireties. A cancer antigen or a fragment thereof can be a protein expressed in a cancer cell but not a normal cell. A cancer antigen or a fragment thereof can be a protein over-expressed in a cancer cell relative to a normal cell.

A cancer antigen or a fragment thereof can comprise, for example, an antigen selected from HER2, BRCA1, prostate-specific membrane antigen (PSMA), MART-1/MelanA, prostatic serum antigen (PSA), squamous cell carcinoma antigen (SCCA), ovarian cancer antigen (OCA), pancreas cancer associated antigen (PaA), MUC-1, MUC-2, MUC-3, MUC-18, carcino-embryonic antigen (CEA), polymorphic epithelial mucin (PEM), Thomsen-Friedenreich (T) antigen, gp100, tyrosinase, TRP-1, TRP-2, NY-ESO-1, CDK-4, b-catenin, MUM-1, Caspase-8, KIAA0205, HPVE7, SART-1, SART-2, PRAME, BAGE-1, DAGE-1, RAGE-1, NAG, TAG-72, CA125, mutated p21ras, mutated p53, HPV16 E7, RCC-3.1.3, MAGE-1, MAGE-2, MAGE-3, MAGE-4, MAGE-11, GAGE-I, GAGE-6, GD2, GD3, GM2, TF, sTn, gp75, EBV-LMP 1, EBV-LMP 2, HPV-F4, HPV-F6, HPV-F7, alpha-fetoprotein (AFP), CO17-1A, GA733, gp72, p-HCG, gp43, HSP-70, p17 mel, HSP-70, gp43, HMW, HOJ-1, HOM-MEL-55, NY-COL-2, HOM-HD-397, HOM-RCC-1.14, HOM-HD-21, HOM-NSCLC-11, HOM-MEL-2.4, HOM-TES-11, melanoma gangliosides, TAG-72, prostatic acid phosphatase, protein MZ2-E, folate-binding-protein LK26, truncated epidermal growth factor receptor (EGFR), GM-2 and GD-2 gangliosides, polymorphic epithelial mucin, folate-binding protein LK26, pancreatic oncofetal antigen, cancer antigen 15-3, cancer antigen 19-9, cancer antigen 549, cancer antigen 195 or a fragment thereof.

A cancer antigen or a fragment thereof can also comprise a novel antigen that is specific to an individual tumor. For example, mRNAs that are overexpressed in a tumor sample, as compared to a control sample from the same individual, can be used to construct a nucleic acid sequence comprising a tumor-specific antigen fused to MIP-3α.

In one embodiment, a nucleic acid sequence is provided comprising a sequence that encodes a cancer antigen or a fragment thereof fused to MIP-3α.

3 Alzheimer's Disease Antigen

In one embodiment, a nucleic acid sequence is provided comprising a sequence that encodes an Alzheimer's disease antigen or a fragment thereof fused to an immune cell product, e.g., MIP-3α or a fragment or mimic thereof. In one embodiment, a nucleic acid sequence is provided comprising a sequence that encodes an Alzheimer's disease antigen or a fragment thereof fused to a ligand for a receptor on a dendritic cell, e.g., MIP-3α or a fragment or mimic thereof. Alzheimer's disease is a form of dementia that can progressively worsen over time Alzheimer's disease can affect memory, thinking, and behavior Alzheimer's disease can result in problems with language, decision-making ability, judgment, and personality Alzheimer's disease can include early onset Alzheimer's disease (first symptoms before age 60) and late onset Alzheimer's disease (first symptoms develop at age 60 or older) Alzheimer's disease can be characterized by the presence of neurofibrillary tangles, neuritic plaques, or senile plaques in the brain.

An Alzheimer's disease antigen or a fragment thereof can be an antigen or a fragment thereof expressed in a subject with Alzheimer's disease but not in a subject without Alzheimer's disease. An Alzheimer's disease antigen or a fragment thereof can be an antigen or a fragment thereof overexpressed in a subject with Alzheimer's disease relative to a subject that does not have Alzheimer's disease. The Alzheimer's disease antigen can be, for example, A68, Aβ40, Aβ42 or a fragment thereof (see, e.g., Gao C M, et al. (2010) Ab40 Oligomers Identified as a Potential Biomarker for the Diagnosis of Alzheimer's Disease. PLoS ONE 5(12): e15725. doi: 10.1371/journal.pone.0015725).

In one embodiment, a nucleic acid sequence is provided comprising a sequence that encodes an Alzheimer's disease antigen fused to MIP-3α.

4. Viral Antigens

In one embodiment, a nucleic acid sequence is provided comprising a sequence that encodes a viral antigen or a fragment thereof fused to an immune cell product, e.g., MIP-3α or a fragment or mimic thereof. In one embodiment, a nucleic acid sequence is provided comprising a sequence that encodes a viral antigen or a fragment thereof fused to a ligand for a receptor on a dendritic cell, e.g., MIP-3α or a fragment or mimic thereof. In one embodiment, the virus is Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolas, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, or the Yug Bogdanovac virus.

In one embodiment, the viral antigen is a hepatitis C virus protein or protein fragment, a human immunodeficiency virus (HIV) protein or protein fragment, an influenza virus protein or protein fragment, or a herpes simplex visus protein or protein fragment (e.g., an hepatitis C virus E2, HIV env, HIV gag, HIV nef, HIV tat, HIV pol, influenza virus hemaglutinin (HA), influenza virus neuraminidase (NA), influenza virus matrix, herpes simplex virus glycoprotein D, or herpes simplex virus glycoprotein B protein or protein fragment.

5. Bacterial Antigens

In one embodiment, a nucleic acid sequence is provided comprising a sequence that encodes a bacterial antigen or a fragment thereof fused to an immune cell product, e.g., MIP-3α or a fragment or mimic thereof. In one embodiment, a nucleic acid sequence is provided comprising a sequence that encodes a bacterial antigen or a fragment thereof fused to a ligand for a receptor on a dendritic cell, e.g., MIP-3α or a fragment or mimic thereof. In one embodiment, the bacterium is *Acetobacter aurantius, Acinetobacter baumannii, Actinomyces israelii, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaminogenicus (Prevotella melaminogenica), Bartonella henselae, Bartonella quintana, Bordetella bronchiseptica, Bordetella pertussis, Borrelia burgdorferi, Brucella abortus, Brucella melitensis, Brucella suis, Burkholderia, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Clostridium botulinum, Clostridium difficile, Clostridium perfringens* (previously called *Clostridium welchii*), *Clostridium tetani, Corynebacterium diphtheria, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenza, Haemophilus parainfluenzae, Haemophilus pertussis, Haemophilus vaginalis, Helicobacter pylori, Klebsiella pneumonia, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheria, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumonia, Lactobacillus Bulgaricus, Neisseria gonorrhoeae, Neisseria meningitides, Pasteurella multocida, Pasteurella tularensis, Peptostreptococcus, Porphyromonas gingivalis, Pseudomonas aeruginosa, Rhizobium radiobacter, Rickettsia prowazekii, Rickettsia psittaci, Rickettsia Quintana, Rickettsia rickettsii, Rickettsia trachomas, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumonia, Streptococcus pyogenes, Streptococcus rattus, Streptococcus salivarius, Streptococcus sanguis, Streptococcus sobrinus, Treponema pallidum, Treponema denticola, Vibrio cholera, Vibrio comma, Vibrio para-*

*haemolyticus, Vibrio vulnificus, Yersinia enterocolitica, Yersinia pestis,* or *Yersinia pseudotuberculosis.*

6. Fungal Antigens

In one embodiment, a nucleic acid sequence is provided comprising a sequence that encodes a fungal antigen or a fragment thereof fused to an immune cell product, e.g., MIP-3α or a fragment or mimic thereof. In one embodiment, a nucleic acid sequence is provided comprising a sequence that encodes a fungal antigen or a fragment thereof fused to a ligand for a receptor on a dendritic cell, e.g., MIP-3α or a fragment or mimic thereof. In one embodiment, the fungi is *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Fusarium solani, Geotrichum candidum, Histoplasma capsulatum, Hortaea werneckii, Issatschenkia orientalis, Madurella grisae, Malassezia furfur, Malassezia globosa, Malassezia obtuse, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium marneffei, Pichia anomala, Pichia guilliermondii, Pneumocystis carinii, Pseudallescheria boydii, Rhizopus oryzae, Rhodotorula rubra, Scedosporium apiospermum, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin,* or *Trichosporon mucoides.*

7. Prion Antigen

In one embodiment, a nucleic acid sequence is provided comprising a sequence that encodes a prion disease antigen or a fragment thereof fused to an immune cell product, e.g., MIP-3α or a fragment or mimic thereof. In one embodiment, a nucleic acid sequence is provided comprising a sequence that encodes a prion disease antigen or a fragment thereof fused to a ligand for a receptor on a dendritic cell, e.g., MIP-3α or a fragment or mimic thereof. In one embodiment, the prion disease is Creutzfeldt-Jakob Disease (CJD), Variant Creutzfeldt-Jakob Disease (vCJD), Gerstmann-Straussler-Scheinker Syndrome, Fatal Familial Insomnia, or Kuru.

8. Epitope Types

In one embodiment, the antigen is a MHC Class I epitope, a MHC Class II epitope, or a B cell epitope. A T cell epitope presented by MHC Class I molecules can be a peptide of approximately 8 to 11 amino acids. A T cell epitope presented by MHC Class II molecules can be longer than a MHC Class I molecule. A T cell epitope (MHC Class I or MHC Class II) web-based prediction tool is available at, e.g., http://tools.immuneepitope.org/main/html/tcell_tools.html. A web based B cell epitope prediction tool is available at, e.g., http://tools.immuneepitope.org/main/html/bcell_tools.html C. Nucleic Acid Sequence Properties In one embodiment, the nucleic acid sequence is DNA, cDNA, RNA, mRNA, siRNA, miRNA, chromosomal DNA, genomic DNA, mitochondrial DNA, cell-free DNA, recombinant DNA, a plasmid, linear DNA, cosmid, shuttle plasmid, virus, retrovirus, and/or artificial chromosome. In one embodiment, a plasmid is provided comprising a sequence that encodes an antigen fused to an immune cell product, e.g., MIP-3α. In one embodiment, a plasmid is provided comprising a sequence that encodes an antigen fused to a molecule that binds a dendritic cell, e.g., MIP-3α. In one embodiment, a plasmid is provided comprising a sequence that encodes an antigen fused to a ligand for a receptor on a dendritic cell, e.g., MIP-3α or a fragment or mimic thereof.

In one embodiment, the plasmid can replicate in a mammalian cell. In another embodiment the plasmid cannot replicate in a mammalian cell.

The plasmid can comprise a viral promoter. The promoter can be, e.g., SV40 enhancer and early promoter region or cytomegalovirus (CMV) immediate/early promoter.

The plasmid can comprise intron A, which can improve mRNA stability.

The plasmid can comprise a polyadenylation or transcriptional termination signal. For example, the polyadenylation signal can be the bovine growth hormone polyadenylation signal, rabbit beta-globulin polyadenylation signal, or late SV40 polyadenylation signal.

In one embodiment, the nucleic acid sequence is codon optimized for expression in a eukaryotic cell.

The plasmid can comprise an antibiotic resistance gene to facilitate replication of the plasmid in a microorganism, e.g., bacteria. The antibiotic resistance gene can permit growth of a microorganism harboring a plasmid with the antibiotic resistance gene in medium containing, e.g., ampicillin, kanamycin, or chloramphenicol.

In one embodiment, the nucleic acid sequence comprises a leader sequence. The leader sequence can be, for example, a tissue plasminogen activator leader sequence, an IgG light chain leader sequence, an IL-2 leader sequence, an insulin leader sequence, an albumin leader sequence, a lysozyme leader sequence, or a trypsinogen-2 leader sequence.

In one embodiment, the nucleic acid sequence comprises an N-terminal secretion sequence.

In one embodiment, the nucleic acid sequence comprises a sequence between the sequence encoding the antigen and the sequence encoding the immune cell product (i.e. spacer sequence). In another embodiment, the nucleic acid sequence comprises sequence between the sequence encoding the antigen and the sequence encoding a molecule that binds a dendritic cell (i.e. spacer sequence). In one embodiment, the spacer sequence is about 3 to 300 nucleotides, 3 to 240 nucleotides, 3 to 210 nucleotides, 3 to 180 nucleotides, 3 to 150 nucleotides, 3 to 120 nucleotides, 3 to 90 nucleotides, 3 to 60 nucleotides, or 3 to 36 nucleotides in length. In one embodiment spacer sequence encodes the amino acid sequence: EFNDAQAPKSGS (SEQ ID NO: 1). In one embodiment, the spacer sequence encodes an amino acid sequence that comprises at least about 10, 15, 20, 25, 30, 35, 40, 45, 50, 55, 60, 65, 70, 75, 80, 85, 90, or 95 percent serine, glycine, and/or alanine. In one embodiment, the spacer sequence encodes at least 1, 2, or 3 prolines. In another embodiment, the spacer sequence encodes at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 35, 35 36, 37, 38, 39, or 40 amino acids. In another embodiment, the spacer sequence encodes about 1-40, 1-30, 1-20, 1-15, 1-10, 1-5, 5-40, 5-30, 5-20, or 5-15 amino acids. In one embodiment, the spacer sequence encodes the amino acid sequence (GGGS)$_2$GS (SEQ ID NO: 2), (GGGS)$_3$GS (SEQ ID NO: 3), (GGGS)$_4$GS(SEQ ID NO: 4), (GGGS)$_5$GS (SEQ ID NO: 5), or (GGGS)$_6$GS (SEQ ID NO: 6). In one embodiment, the spacer sequence encodes the amino acid sequence GPGPG (SEQ ID NO: 7). The spacer sequence can allow for proper folding of the antigen and the immune cell product, or the antigen and a molecule that binds a dendritic cell.

In one, the nucleic acid sequence further expresses a T cell helper epitope. In one embodiment, the T cell helper epitope is the pan DR epitope (PADRE).

The sequence encoding the antigen can be 5' of the sequence encoding the immune cell product. The sequence encoding the antigen can be 3' of the sequence encoding the immune cell product.

In another embodiment, the nucleic acid sequence comprises sequence encoding an antigen fused to an immune cell product, wherein the antigen fused to the immune cell product is also fused to an epitope tag. In one embodiment, the epitope tag is a Myc-tag, isopegtag, BCCP, calmodulin-tag, FLAG-tag, HA-tag, His-tag (e.g., 6His-tag (SEQ ID NO: 8)), maltose binding protein-tag, Nus-tag, glutathione-S-transferase-(GST)-tag, green fluorescent protein-(GFP)-tag, thioredoxin-tag, S-tag, Softag-1, Softag 3, Strep-tag, SBP-tag, Ty tag, or V5-tag. The epitope tag can be a tandem tag. The epitope tag can comprise multiple copies of an epitope tag (e.g., 3×Myc-tag, 13×Myc-tag, 3×FLAG-tag, 3×HA-tag). The epitope tag can be used to evaluate protein secretion and to facilitate protein purification.

The sequence encoding the epitope tag can be 5' of the sequence encoding the antigen. The sequence encoding the epitope tag can be 3' of the sequence encoding the antigen. The antigen-immune cell product protein, or an antigen fused to a molecule that binds a dendritic cell protein, expressed from a nucleic acid sequence, can have an epitope tag at the N-terminus, at the C-terminus, at the N-terminus and the C-terminus, internal, at the N-terminus and internal, at the C-terminus and internal, or at the N-terminus, internal, and at the C-terminus.

In one embodiment, a plasmid is provided. In one embodiment, DNA for a tissue plasminogen activator leader sequence and the DNA for macrophage inflammatory protein 3-alpha (CCL20) fused to a codon optimized DNA, encoding portions of the P. falciparum circumsporozoite protein is inserted into plasmid VR1012. In one embodiment, a VR1012 plasmid is synthesized to include restriction sites that permit insertion of sequences into the plasmid.

The nucleic acid sequence can comprises one or more base changes (e.g., insertion, deletion, mutation) in an antigen sequence or immune cell product sequence relative to wild-type. The nucleic acid sequence can comprise one or more base changes in an antigen sequence or molecule that binds a dendritic cell. Changes to nucleic acid sequence can be made, e.g., with the QuikChange site-directed mutagenesis kit.

III. Polypeptides

In one embodiment, a polypeptide is provided comprising an antigen or a fragment thereof fused to an immune cell product, e.g., MIP-3α. In another embodiment, a polypeptide is provided comprising an antigen or a fragment thereof fused to a molecule that binds a dendritic cell, e.g., MIP-3α. The polypeptide can be any polypeptide that can be expressed from a nucleic acid sequence described herein. In one embodiment the polypeptide is provided in a pharmaceutical composition for use in the treatment or prevention of a disease disclosed herein. In one embodiment the polypeptide is a vaccine. Polypeptide vaccines are described, e.g., in U.S. Patent Application Nos. 20090060915 and 20110027349, which are herein incorporated by reference in their entireties.

The polypeptide can be synthesized in, for example, a bacteria, yeast, insect cell, or mammalian cell. The bacteria can be, e.g., E. coli. The E. coli strain can be BL21. The expression system can make use of a T7lac promoter. The polypeptide can be expressed from, e.g., a pET vector or a pBAD vector. The yeast can be, e.g., Saccharomyces cerevisiae or Pichia pastoris. The insect cell can be SF-9 or SF-21 ovarian cell lines from Spodoptera frugiperda, or High-Five cells (egg cells from Trichoplusia ni). A baculovirus can be used to express the polypeptide in an insect cell. The polypeptide can be produced by fermentation.

The polypeptide can be synthesized in a cell free extract. A cell free expression system can couple transcription and translation. The cell free system can be, e.g., the Expressway™ Cell-Free Expression System from Invitrogen.

The polypeptide can be purified by conventional chromatography. The polypeptide can comprise an epitope tag, e.g., and epitope tag described herein, that can be used to facilitate purification of the polypeptide. Methods of purifying proteins are described, e.g., in Current Protocols in Protein Science, Print ISSN: 1934-3655.

Amino acids in a polypeptide can be in the L-isomeric form. The D-isomeric form of an amino acid can be substituted for the L-amino acid residue. $NH_2$ refers to the free amino group present at the amino terminus of a polypeptide, and COOH refers to the free carboxyl group present at the carboxyl terminus of a polypeptide. The amino acids herein can be represented by their standard 1-letter code or 3-letter code. An amino acid residue represented by "X" or "Xxx" refers to any one of the naturally occurring or non-naturally occurring amino acid residues known in the art or to a modification of a nearby residue. In keeping with standard protein nomenclature described in J. Biol. Chem., 1969, 247:3552-59, and adopted at 37 C.F.R. Sections 1.821-2461.822, all amino acid residue sequences represented herein by formulae have a left to right orientation in the conventional direction of amino-terminus to carboxyl-terminus. In addition, the phrase "amino acid residue" is broadly defined to include modified and unusual amino acids, such as those referred to in 37 C.F.R. Sections 1.821-1.822, and incorporated herein by reference. In a peptide or polypeptide, suitable conservative substitutions of amino acids are known to those of skill in this art and can be made generally without altering the biological activity of the resulting molecule. Watson et al., book (1987, Molecular Biology of the Gene, 4th Edition, The Benjamin Cummings Pub. Co., p. 224), is incorporated herein by reference Amino acid substitutions can be of single residues; such substitutions are preferably made with those set forth in Table I., but can be of multiple residues, either clustered or dispersed. An amino acid can be replaced with a different naturally occurring or a non-conventional amino acid residue. Such substitutions can be classified as "conservative," in which case an amino acid residue contained in a polypeptide is replaced with another naturally occurring amino acid of similar character either in relation to polarity, side chain functionality or size. Additions encompass the addition of one or more naturally occurring or non-conventional amino acid residues. Deletion encompasses the deletion of one or more amino acid residues.

TABLE I

Conservative amino acid substitution

| Original residue | Conservative substitution(s) |
| --- | --- |
| Ala | Gly; Ser |
| Arg | Lys |
| Asn | Gln; His |
| Cys | Ser |
| Gln | Asn |
| Glu | Asp |

TABLE I-continued

Conservative amino acid substitution

| Original residue | Conservative substitution(s) |
|---|---|
| Gly | Ala; Pro |
| His | Asn; Gln |
| Ile | Leu; Val |
| Leu | Ile; Val |
| Lys | Arg; Gln; Glu |
| Met | Leu; Tyr, Ile |
| Phe | Met; Leu; Tyr |
| Ser | Thr |
| Thr | Ser |
| Trp | Tyr |
| Tyr | Trp; Phe |
| Val | Ile; Leu |

Substitutions can be "non-conservative," in which an amino acid residue which is present in a peptide is substituted with an amino acid having different properties, such as naturally-occurring amino acid from a different group (e.g., substituting a charged or hydrophobic amino acid with alanine), or alternatively, in which a naturally-occurring amino acid is substituted with a non-conventional amino acid.

The term "analog(s)" as used herein can refer to a composition that retains the same structure or function (e.g., binding to a receptor) as a polypeptide or nucleic acid sequence herein, such as the same gene from a different organism. Examples of analogs include mimetics or peptidomimetics, peptide, nucleic acids, small and large organic or inorganic compounds, as well as derivatives and variants of a polypeptide or nucleic acid herein. Such derivatives and variants refer to peptides and nucleic acids that differ from the naturally occurring polypeptides and nucleic acids by one or more amino acid or nucleic acid deletions, additions, substitutions or side-chain modifications. In some embodiments, a peptide analog is a peptide in which one or more of the amino acids has undergone side-chain modifications. Examples of side-chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$. In some embodiments, a peptide analog is one in which the guanidine group of arginine residue(s) is modified by the formation of heterocyclic condensation products with reagents such as 2,3-butanedione, phenylglyoxal and glyoxal; carboxyl group(s) is modified by carbodiimide activation via O-acylisourea formation followed by subsequent derivitisation, for example, to a corresponding amide; sulphydryl group(s) can be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. In any of the analogs herein, any modification of cysteine residues can or can not affect the ability of the peptide to form disulphide bonds. In some embodiments, a peptide analog comprises tryptophan residue(s) that are modified by, for example, by oxidation with N-bromosuccinimide or alkylation of the indole ring with 2-hydroxy-5-nitrobenzyl bromide or sulphenyl halides; tyrosine residues altered by nitration with tetranitromethane to form a 3-nitrotyrosine derivative; imidazole ring(s) of a histidine residue modification accomplished by alkylation with iodoacetic acid derivatives or N-carbethoxylation with diethylpyrocarbonate; proline residue(s) modified by, for example, hydroxylation in the 4-position; glycosylation variants from a completely unglycosylated molecule to a modified glycosylated molecule; and altered glycosylation patterns as a result from expression of recombinant molecules in different host cells.

Provided in Table 2 are nucleic acid sequences or protein sequences for immune cell products and/or molecules that can target (e.g., bind) a dendritic cell.

TABLE 2

Sequences

| Antigen label | Nucleic acid sequence or protein sequence |
|---|---|
| DEFB4A mRNA [Homo sapiens] NM_004942.2 | agactcagct cctggtgaag ctcccagcca tcagccatga gggtcttgta tctcctcttc tcgttcctct tcatattcct gatgcctctt ccaggtgttt ttggtggtat aggcgatcct gttacctgcc ttaagagtgg agccatatgt catccagtct tttgccctag aaggtataaa caaattggca cctgtggtct ccctggaaca aaatgctgca aaaagccatg aggaggccaa gaagctgctg tggctgatgc ggattcagaa agggctccct catcagagac gtgcgacatg taaaccaaat taaactatgg tgtccaaaga tacgca (SEQ ID NO: 9) |
| DEFB4A protein [Homo sapiens] ACCESSION O15263 | mrvlyllfsf lfiflmplpg vfggigdpvt clksgaichp vfcprrykqi gtcglpgtkc ckkp (SEQ ID NO: 10) |
| Homo sapiens beta-defensin 3 mRNA, complete cds. ACCESSION AF301470.1 | caaatccata gggagctctg ccttaccatt gggttcctaa ttaactgagt gagtgggtgt gttctgcatg gtgagaggca ttggaatgat gcatcagaaa acatgtcata atgtcatcac tgtaatatga caagaattgc agctgtggct ggaacctttta taaagtgacc aagcacacct tttcatccag tctcagcgtg gggtgaagcc tagcagctat gaggatccat tatcttctgt ttgctttgct cttcctgttt ttggtgcctg ttccaggtca tggaggaatc ataaacacat tacagaaata ttattgcaga gtcagaggcg gccggtgtgc tgtgctcagc tgccttccaa aggaggaaca gatcggcaag tgctcgacgc gtggccgaaa atgctgccga agaaagaaat aaaaaccctg aaacatg (SEQ ID NO: 11) |

TABLE 2-continued

Sequences

| Antigen label | Nucleic acid sequence or protein sequence |
|---|---|
| Beta-Defensin 3 protein [Homo sapiens] ACCESSION AAG22030.1 | mrihyllfal lflflvpvpg hggiintlqk yycrvrggrc avlsclpkee qigkcstrgr kccrrkk (SEQ ID NO: 12) |
| CCL20 (MIP 3α) mRNA Homo sapiens chemokine (C-C motif) ligand 20 (CCL20), transcript variant 1 Accession number: NM_004591 | agaatataac agcactccca aagaactggg tactcaacac tgagcagatc tgttctttga gctaaaaacc atgtgctgta ccaagagttt gctcctggct gctttgatgt cagtgctgct actccacctc tgcggcgaat cagaagcagc aagcaacttt gactgctgtc ttggatacac agaccgtatt cttcatccta aatttattgt gggcttcaca cggcagctgg ccaatgaagg ctgtgacatc aatgctatca tctttcacac aaagaaaaag ttgtctgtgt gcgcaaatcc aaaacagact tgggtgaaat atattgtgcg tctcctcagt aaaaagtca agaacatgta aaaactgtgg cttttctgga atggaattgg acatagccca agaacagaaa gaaccttgct ggggttggag gtttcacttg cacatcatgg aggtttagt gcttatctaa tttgtgcctc actggacttg tccaattaat gaagttgatt catattgcat catagtttgc tttgtttaag catcacatta aagttaaact gtattttatg ttatttatag ctgtaggttt tctgtgttta gctatttaat actaattttc cataagctat tttggtttag tgcaaagtat aaaattatat ttggggggga ataagattat atggactttc ttgcaagcaa caagctattt tttaaaaaaa actatttaac attcttttgt ttatattgtt ttgtctccta aattgttgta attgcattat aaaataagaa aaatattaat aagacaaata ttgaaaataa agaaacaaaa agttcttctg ttaaaaaaaa a (SEQ ID NO: 13) |
| CCL20 protein human Accession number: P78556 | mcctkslla almsvlllhl cgeseaasnf dcclgytdri lhpkfivgft rqlanegcdi naiifhtkkk lsvcanpkqt wvkyivrlls kkvknm (SEQ ID NO: 14) |
| Homo sapiens chemokine (C-C motif) ligand 20 (CCL20), transcript variant 2, mRNA. ACCESSION NM_001130046 | agaatataac agcactccca aagaactggg tactcaacac tgagcagatc tgttctttga gctaaaaacc atgtgctgta ccaagagttt gctcctggct gctttgatgt cagtgctgct actccacctc tgcggcgaat cagaagcaag caactttgac tgctgtcttg gatacacaga ccgtattctt catcctaaat ttattgtggg cttcacacgg cagctggcca atgaaggctg tgacatcaat gctatcatct tcacacaaa gaaaagttg tctgtgtgcg caaatccaaa acagacttgg gtgaaatata ttgtgcgtct ccagtaaa aaggtcaaga acatgtaaaa actgtggctt ttctggaatg gaattggaca tagcccaaga acagaaagaa ccttgctggg gttggaggtt tcacttgcac atcatggagg tttagtgct tatctaattt gtgcctcact ggacttgtcc aattaatgaa gttgattcat attgcatcat agtttgcttt gtttaagcat cacattaaag ttaaactgta ttttatgtta tttatagctg taggttttct gtgtttagct atttaatact aattttccat aagctatttt ggtttagtgc aaagtataaa attatatttg gggggaata agattatatg gactttcttg caagcaacaa gctattttt aaaaaaact atttaacatt cttttgttta ttgttttg tctcctaaat tgttgtaatt gcattataaa ataagaaaa tattaataag acaaatattg aaaataaga acaaaaagt tcttctgtta aaaaaaaa (SEQ ID NO: 15) |
| Mus musculus chemokine (C-C motif) ligand 20 (Ccl20), transcript variant 1, mRNA. ACCESSION NM_016960 XM_484888 | gagcactcgc agggcactgg gtacccagca ctgagtacat caactcctgg agctgagaat ggcctgcggt ggcaagcgtc tgctcttcct tgctttggca tgggtactgc tggctcacct ctgcagccag gcagaagcag caagcaacta cgactgttgc ctctcgtaca tacagacgcc tcttcctcc agagctattg tgggtttcac aagacagatg gccgatgaag cttgtgacat taatgctatc atctttcaca cgaagaaaag aaaatctgtg tgcgctgatc aaagcagaa ctgggtgaaa agggctgtga acctcctcag cctaagagtc aagaagatgt aaaaactga tgctttttg gatggaatt ggacacagc caaggaggaa atgatcacag ctggggttga aggcttcacc tgcacatcac tgcacagacc tgatttgtgt cccagtggac ttgtccaatg gatgaagttg attcatattg catcatagtg tgtcatattt aagctcacat tagagttaag ttgtatttta tgttatttat agatctgaat tttctatgtt tagctattta atgttaattt cccacaatcc atggggcgc ttagtggaag gaataattat atggaccttt tttgtcaaca ataagctatt gtaaagatat ttaatgttct gtttatttaa ttgcttctta aattgatatg attttcttat aaaacagaaa agaattataa gaatatattg aaaataaaag aattgaaagg taaaaaaaaa aaaaaaaaaa aaaaaaaaaa aaaaaaaaaa aaaaaaaaaa aa (SEQ ID NO: 16) |
| Mus musculus chemokine (C-C motif) ligand 20 (Ccl20), transcript variant 2, mRNA. ACCESSION NM_001159738 | gagcactcgc agggcactgg gtacccagca ctgagtacat caactcctgg agctgagaat ggcctgcggt ggcaagcgtc tgctcttcct tgctttggca tgggtactgc tggctcacct ctgcagccag gcagaagcag caactacga ctgttgcctc tcgtacatac agacgcctct tcctccagag ctattgtggg ttcacaag acagatggcc gatgaagctt gtgacattaa tgctatcatc tttcacacga gaaaagaaa tctgtgtgc gctgatccaa agcagaactg ggtgaaaagg gctgtgaacc cctcagcct aagagtcaag aagatgtaaa aactgatgc ttttttggga tggaattgga cacagcccaa ggaggaaatg atcacagctg gggttgaagg cttcacctgc acatcactgc acagacctga tttgtgtccc agtggacttg tccaatggat gaagttgatt catattgcat catagtgtgt catatttaag ctcacattag agttaagttg tattttatgt tatttataga tctgaatttt ctatgtttag ctatttaatg ttaatttccc acaatccatg gggcgctta gtgaaggat taatatatg tttaaggatt agtttatat ggacctttt gtcaacaata agctattgt aagatatttt atgttctgtt tatttaattg cttcttaaat tgatatgatt tcttataa acagaaaga attataagaa tatattgaaa ataaaagaat tgaaaggtaa aaaaaaaa aaaaaaaaa aaaaaaaaaa aaaaaaaaa aaaaaaaa (SEQ ID NO: 17) |

TABLE 2-continued

Sequences

| Antigen label | Nucleic acid sequence or protein sequence |
|---|---|
| CCL20 protein [*Mus musculus*] Accession number: O89093 | macggkrllf lalawvllah lcsqaeaasn ydcclsyiqt plpsraivgf trqmadeacd inaiifhtkk rksvcadpkq nwvkravnll slrvkkm (SEQ ID NO: 18) |
| *Homo sapiens* chemokine (C-C motif) ligand 5 (CCL5), mRNA ACCESSION NM_002985 | gctgcagagg attcctgcag aggatcaaga cagcacgtgg acctcgcaca gcctctccca caggtaccat gaaggtctcc gcggcagccc tcgctgtcat cctcattgct actgccctct gcgctcctgc atctgcctcc ccatattcct cggacaccac acctgctgc tttgcctaca ttgcccgccc actgcccgt gcccacatca aggagtattt ctacaccagt ggcaagtgct ccaacccagc agtcgtcttt gtcacccgaa agaaccgcca agtgtgtgcc aacccagaga agaaatgggt tcgggagtac atcaactctt ggagatgag ctaggatgga gagtccttga acctgaactt acacaaattt gcctgtttct gcttgctctt gtcctagctt gggaggcttc ccctcactat cctaccccac ccgctccttg aagggcccaa attctaccac acagcagcag ttacaaaaac cttcccagg ctggacgtgg tggctcacgc ctgtaatccc agcactttgg gaggccaagg tgggtggatc acttgaggtc aggagttcga ccagcctg ccaacatga tgaaacccca tctctactaa aaatacaaaa aattagccgg gcgtggtagc gggcgcctgt agtcccagct actcgggagg ctgaggcagg agaatgggcgt gaacccggga gggagagctt gcagtgagcc gagatcgcgc cactgcactc cagcctgggc gacagagcga gactccgtct caaaaaaaaa aaaaaaaaaa aaaatacaaa aattagccgg gcgtggtggc ccacgcctgt aatcccagct actcgggagg ctaaggcagg aaaattgttt gaacccagga ggtggaggct gcagtgagcc gagattgtgc cactttcactc cagcctgggt gacaaagtga gactccgtca caacaacaac aacaaaaagc ttccccaact aaagcctaga agagcttctg aggcgctgct ttgtcaaaag gaagtctcta ggttctgagc tctggctttg ccttggcttt gccagggctc tgtgaccagg aaggaagtca gcatgcctct agaggcaagg aggggaggaa cactgcactc ttaagcttcc gccgtctcaa cccctcacag gagcttactg gcaaacatga aaaatcggct taccattaaa gttctcaatg caaccataaa aaaaaaa (SEQ ID NO: 19) |
| CCL5_HUMAN Protein [*Homo sapiens*] ACCESSION P13501 | mkvsaaalav iliatalcap asaspyssdt tpccfayiar plprahikey fytsgkcsnp avvfvtrknr qvcanpekkw vreyinslem s (SEQ ID NO: 20) |
| *Mus musculus* chemokine (C-C motif) ligand 5 (Ccl5) mRNA. ACCESSION NM_013653 | cttgcagagg actctgagac agcacatgca tctcccacag cctctgccgc gggtaccatg aagatctctg cagctgccct caccatcatc ctcactgcag ccgcccctg cacccccgca cctgcctcac catatgctc ggacaccact ccctgctgct ttgcctacct ctccctcgcg ctgcctcgtg cccacgtcaa ggagtatttc tacaccagca gcaagtgctc caatcttgca gtcgtgtttg tcactcgaag gaaccgccaa gtgtgtgcca acccagagaa gaagtgggtt caagaataca tcaactattt ggagatgagc taggatagag ggtttcttga ttctgaccct gtatagcttc cctgtcattg cttgctctag tcctagccag cttggggatg ccactcagta atcccctact cccactcggt cctgggaaaa tgggcatctc agctgctccg aggctctgca cagcaaaccc aagaaatcag catttcatta aaatttcaaa tgcaaggaca aaaaaaaaaa aaaaaaaaaa aaaaaaaaaa aaaaaaaaaa aaaaaaaa (SEQ ID NO: 21) |
| Ccl5 [*Mus musculus*] ACCESSION CAJ18523 | mkisaaalti iltaaalctp apaspygsdt tpccfaylsl alprahvkey fytsskcsnl avvfvtrrnr qvcanpekkw vqeyinylem s (SEQ ID NO: 22) |
| *Homo sapiens* chemokine (C-C motif) ligand 3 (CCL3), mRNA. ACCESSION NM_002983 | agctggtttc agacttcaga aggacacggg cagcagacag tggtcagtcc tttcttggct ctgctgacac tcgagcccac attccgtcac ctgcagaa tcatgcaggt ctccactgct gcccttgctg tcctcctctg caccatggct ctctgcaacc agttctctgc atcacttgct gctgacacgc gaccgcctgc tgcttcagc tacacctccc ggcagattcc acagaatttc atagctgact actttgagac gagcagccag tgctccaagc ccggtgtcat cttcctaacc aagcgaagcc ggcaggtctg tgctgacccc agtgaggagt gggtccagaa atatgtcagc gacctggagc tgagtgcctg aggggtccag aagcttcaga gcccagcgac ctcggtgggc ccagtgggga ggagcaggaa cctgagcctt gggaacatgc gtgtgacctc acagctacc tcttctatgg actggttgtt gccaaacagc cacactgtgg gactcttctt aacttaaatt ttaatttatt tatactattt agttttttgta atttatttc gatttcacag tgtgtttgtg attgtttgct ctgagagttc ccctgtcccc tcccccttcc ctcacaccgc gtctggtgac aaccgagtgg ctgtcatcag cctgtgtagg cagtcatggc accaaagcca ccagactgac aaatgtgtat cggatgcttt tgttcagggc tgtgatcggc ctggggaaat aataaagatg ctcttttaaa aggtaaaaaa aaaaaaaaaa aaa (SEQ ID NO: 23) |
| Chemokine (C-C motif) ligand 3 [*Hom sapiens*]. ACCESSION AAH71834 | mqvstaalav llctmalcnq fsasllaadtp taccfsytsr qipqnfiady fetsssqcskp gvifltkrsr qvcadpseew vqkyvsdlel sa (SEQ ID NO: 24) |
| *Mus musculus* chemokine (C-C motif) ligand 3 (Ccl3) mRNA. ACCESSION NM_011337 | gggcatatgg cttcagacac cagaaggata caagcagcag cgagtaccag tccctttct gttctgctga caagctcacc ctctgtcacc tgctcaacat catgaaggtc tccaccactg ccccttgctgt tcttctctgt accatgacac tctgcaacca agtcttctca gcgccatatg gagctgacac cccgactgcc tgctgcttct cctacagccg aagattcca cgccaattca tcgttgacta ttttgaaacc agcagccttt gctcccagcc aggtgtcatt ttcctgacta agagaaaccg gcagatctgc gctgactcca agagacctg gtccaagaa tacatcactg acctggaact gaatgcctga gagtccttgga ggcagcgagg aaccccccaa acctccatgg |

TABLE 2-continued

Sequences

| Antigen label | Nucleic acid sequence or protein sequence |
|---|---|
| | gtcccgtgta gagcaggggc ttgagccccg gaacattcct gccacctgca tagctccatc<br>tcctataagc tgtttgctgc caagtagcca catcgaggga ctcttcactt gaaattttat<br>ttaatttaat cctattggtt taatactatt taattttgta atttatttta ttgtcatact<br>tgtatttgtg actatttatt ctgaaagact tcaggacacg ttcctcaacc cccatctccc<br>tcccagttgg tcacactgtt tggtgacagc tattctaggt agacatgatg acaaagtcat<br>gaactgacaa atgtacaata gatgctttgt ttataccaga gaagtaataa atatgcccctt<br>taacaagtga aaaaaaaaaa aaaa (SEQ ID NO: 25) |
| C-C motif chemokine 3<br>[Mus musculus].<br>ACCESSION<br>NP_035467 | mkvsttalav llctmtlcnq vfsapygadt ptaccfsysr kiprqfivdy fetsslcsqp<br>gvifltkrnr qicadsketw vqeyitdlel na (SEQ ID NO: 26) |
| Mus musculus defensin beta 2 (Defb2), mRNA<br>ACCESSION<br>NM_010030 | ctctctggag tctgagtgcc ctttctacca gccatgagga ctctctgctc tctgctgctg<br>atatgctgcc tcctttctc atataccact ccagctgttg gaagtttaaa aagtattgga<br>tacgaagcag aacttgacca ctgccacacc aatggagggt actgtgtcag agccatttgt<br>cctccttctg ccaggcgtcc tgggagctgt ttcccagaga agaaccctg ttgcaagtac<br>atgaaatgat tagaaggaag cacatggaag tcaagtgaca gatgtgtaat tgatgtttca<br>ataaa (SEQ ID NO: 27) |
| beta-defensin 2 precursor [Mus musculus<br>ACCESSION<br>NP_034160 | mrtlcsllli ccllfsyttp avgslksigy eaeldhchtn ggycvraicp psarrpgscf<br>peknpcckym k (SEQ ID NO: 28) |

IV. Formulations, Routes of Administration, and Effective Doses

In another aspect, a pharmaceutical composition is provided comprising a nucleic acid sequence comprising a sequence encoding an antigen fused to an immune cell product, and an adjuvant. In another aspect, a pharmaceutical composition is provided comprising a nucleic acid sequence comprising a sequence encoding an antigen fused to a molecule that can bind a dendritic cell, and an adjuvant. In one embodiment, the pharmaceutical composition comprises a nucleic acid sequence encoding an antigen fused to MIP-3α, and an adjuvant. In another embodiment, the pharmaceutical composition comprises a nucleic acid sequence comprising a sequence encoding a parasite antigen fused to an immune cell product, and an adjuvant. In one embodiment, the pharmaceutical composition comprises nucleic acid sequence encoding circumsporozoite protein or protein fragment from P. falciparum fused to MIP-3α, and an adjuvant. In one embodiment, the pharmaceutical composition comprises nucleic acid sequence encoding circumsporozoite protein or protein fragment from P. falciparum fused to MIP-3α, and Vaxfectin® (Vical Inc., San Diego, Calif.). In other embodiments, a pharmaceutical composition is provided comprising a nucleic acid sequence that encodes a P. falciparum antigen fused to an immune cell product, e.g., MIP-3α, in combination with other known adjuvants.

In another aspect, formulations of a pharmaceutical composition, means of administration a pharmaceutical composition by different routes, and effective doses of a pharmaceutical composition are provided herein. In one embodiment a pharmaceutical composition comprises a pharmaceutical immunostimulatory agents described herein, e.g., a nucleic acid sequence or polypeptide described herein. Such pharmaceutical compositions can be used to prevent, inhibit, reduce the severity of, or treat a condition (e.g., malaria, cancer, Alzheimer's disease, bacterial infection, fungal infection, viral infection, parasite infection, etc.) as described herein.

Pharmaceutical immunostimulatory agents (e.g., nucleic acid sequence, polypeptide) described herein can be administered as pharmaceutical compositions including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999). In one embodiment, a pharmaceutical composition comprising a pharmaceutical immunostimulatory agent is provided by parenteral administration. In one embodiment parenteral administration comprises injection.

Liposomes

A pharmaceutical immunostimulatory agent can be encapsulated within a liposome using well-known technology. In one embodiment, an adjuvant is a liposome. In another aspect, biodegradable microspheres can also be employed as carriers a pharmaceutical immunostimulatory agent. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252 which are hereby incorporated by reference in their entireties.

An agent can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material can be dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art and can be tailored for passage through the gastrointestinal tract directly into the blood stream. A pharmaceutical immunostimulatory agent can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference in their entireties.

A liposome can be a particle comprising concentric lipid membranes containing phospholipids and other lipids in a bilayer configuration separated by aqueous compartments. Liposomes can be composed of naturally derived phospholipids or other surfactants. A liposome can encapsulate aqueous solution inside a hydrophobic membrane.

In one embodiment, the liposome comprises a cationic lipid. A cationic lipid can be an amphiphile that has a positive charge (at physiological pH) as measurable by instrumentation utilized at the time of the measurement. An amphiphile can be a molecule consisting of a water-soluble (hydrophilic) and an organic solvent-soluble (lipophilic) moiety. Where there are fatty acids or alkyl chains present on the cationic lipid, they can be 12-24 carbons in length, containing up to 6 unsaturations (double bonds), and linked to the backbone by either acyl or ether linkages; there can also only be one fatty acid or alkyl chain linked to the backbone. Where there is more than one fatty acid or alkyl chain linked to the backbone, the fatty acids can be different (asymmetric). Mixed formulations are also possible. In one embodiment, the cationic lipid is GAP-DMORIE, DSTAP, DMTAP, DC-cholesterol, Ethyl PC, DDAB, dimethyldioctadecyl ammonium bromide; N-[1-(2,3-dioloyloxy)propyl]-N,N,N-trimethyl ammonium methylsulfate; 1,2-diacyloxy-3-trimethylammonium propanes, (including but not limited to, dioleoyl (DOTAP), dilauroyloxy, dimyristoyloxy, dipalmitoyloxy, and distearoyloxy); N-[1-(2,3-dioleoyloxy)propyl]-N,N-dimethyl amine; 1,2-diacyl-3-dimethylammonium propanes, (including but not limited to, dioleoyl (DODAP), dilauroyl. dimyristoyl, dipalmitoyl, and distearoyl); DOTMA, N-[1-[2,3-bis(oleyloxy)]propyl]-N,N,N-trimethylammonium chloride, (including but not limited to, dioleyl (DOTMA), dilauryl, dimyristyl, dipalmityl, and distearyl); DOGS, dioctadecylamidoglycylspermine; DC-cholesterol, 3.beta.-[N—(N',N'-dimethylaminoethane)carbamoyl]cholesterol; DOSPA, 2,3-dioleoyloxy-N-(2-(sperminecarboxamido)-ethyl)-N,N-dimethyl-1-propanam-inium trifluoroacetate; 1,2-diacyl-sn-glycero-3-ethylphosphocholines (including but not limited to dioleoyl (DOEPC), dilauroyl, dimyristoyl, dipalmitoyl, distearoyl, and palmitoyl-oleoyl); .beta.-alanyl cholesterol; CTAB, cetyl trimethyl ammonium bromide; diC14-amidine, N-t-butyl-N'-tetradecyl-3-tetradecylaminopropionamidine; 14Dea2; TMAG, N-(alpha-trimethylammonioacetyl)didodecyl-D-glutamate chloride; O,O'-ditetradecanoyl-N-(trimethylammonioacetyl)diethanolamine chloride; DOSPER, 1,3-dioleoyloxy-2-(6-carboxy-spermyl)-propylamide; N,N,N',N'-tetramethyl-N,N'-bis(2-hydroxylethyl)-2,3-dioleoyloxy-1,4-butan-ediammonium iodide; 1[2-(acyloxy)ethyl]-2-alkyl (alkenyl)-3-(2-hydroxyethyl)imidazolinium chloride, derivatives as described by Solodin et al. (1995) Biochem. 43:13537-13544, such as DOTIM, 1-[2-(9(Z)-octadecenoyloxy)ethyl]-2-(8(Z)-heptadecenyl-3-(2-hydroxy-yethyl) imidazolinium chloride; DPTIM, 1-[2-(hexadecanoyloxy)ethyl]-2-pentadecyl-3-(2-hydroxyethyl)imidazolinium chloride; 2,3-dialkyloxypropyl quaternary ammonium compound derivatives, contain a hydroxyalkyl moiety on the quaternary amine, as described e.g., Feigner et al. (1994) J. Biol. Chem. 269:2550-2561, such as: DOR1, 1,2-dioleoyl-3-dimethyl-hydroxyethyl ammonium bromide; DORIE, 1,2-dioleyloxypropyl-3-dimethyl-hydroxyethyl ammonium bromide; DORIE-HP, 1,2-dioleyloxypropyl-3-dimethyl-hydroxypropyl ammonium bromide; DORIE-HB, 1,2-dioleyloxypropyl-3-dimethyl-hydroxybutyl ammonium bromide; DORIE-HPe, 1,2-dioleyloxypropyl-3-dimethyl-hydroxypentyl ammonium bromide; DMRIE, 1,2-dimyristyloxypropyl-3-dimethyl-hydroxylethyl ammonium bromide; DPRIE, 1,2-dipalmityloxypropyl-3-dimethyl-hydroxyethyl ammonium bromide; or DSRIE, 1,2-disteryloxypropyl-3-dimethyl-hydroxyethyl ammonium bromide. Cationic lipids are described, e.g., in U.S. Pat. No. 7,794,747, which is herein incorporated by reference in its entirety.

In another embodiment, the liposome comprises a neutral lipid, e.g., a neutral phospholipid. In another embodiment, the neutral phospholipid is DPyPE. In another embodiment, a neutral lipid is, e.g., cholesterol; 1,2-diacyl-sn-glycero-3-phosphoethanolamines (including but not limited to dioleoyl (DOPE)); 1,2-diacyl-sn-glycero-3-phosphocholines; natural egg yolk or soy bean phosphatidylcholine (PC), and the like; or synthetic mono- and diacyl-phosphoethanolamines.

In another embodiment, the liposome comprises a commixture of a cationic lipid and a neutral phospholipid which, when combined in an aqueous vehicle, self-assemble to form liposomes. In another embodiment, the liposome comprises a commixture of (±)-N-(3-aminopropyl)-N,N-dimethyl-2,3-bis(cis-9-tetradecenyloxy)-1-propanaminium bromide (GAP-DMORIE) and 1,2-diphytanoyl-sn-glycero-3-phosphoethanolamine (DPyPE). In another embodiment, the liposome that comprises a commixture of GAP-DMORIE and DPyPE is Vaxfectin (Vical). See http://www.vical.com/technology/formulations/vaxfectin/default.aspx Upon mixing with pharmaceutical immunostimulatory agents (e.g., nucleic acid sequence, protein, or vaccine), these cationic liposomes can associate through ionic, charge-based interactions with the pharmaceutical immunostimulatory agents and as a result provide an adjuvant effect, boosting the pharmaceutical immunostimulatory agent's (e.g., vaccine's) ability to stimulate immune responses. In mechanism of action studies, Vaxfectin has been shown to increase a number of cytokines and chemokines, while Toll-like receptor signaling was contributory.

Liposomes can be a liposome from, e.g., Avanti Polar Lipids, Inc., Encapsula Nano Sciences (ENS), Taiwan Liposome Company (tlc), Liposome Company, Inc., Avestin, Inc, and Lyotropic Therapeutics. Liposome-based vaccines are described, e.g., in Schwender R A et al. Liposome-based vaccines. *Methods Mol. Biol.* vol. 605, pp. 163-175 (2010). Interbilayer-crosslinked multilamellar vesicles as synthetic vaccines for potent humoral and cellular immune responses are described, e.g., in James L. Moon et al. (2011) *Nature Materials* vol 10., pp. 243-251, which are hereby incorporated by reference in their entireties.

Examples of DNA vaccines that make use of liposomes are described, e.g., in G. Gregoriadis et al. Entrapment of Plasmid DNA Vaccines into Lipsomes by Dehydration/Rehydration. *Methods in Molecular Medicine* vol. 29 pp. 305-311; Yvonne Perrie et al. Liposome-mediated DNA vaccination: the effect of vesicle composition. *Vaccine* vol. 19, pp. 3301-3310; D. Wang. Liposomal oral DNA vaccine (mycobacterium DNA) elicits immune response. *Vaccine* vol. 28 pp. 3134-42 (2010);

Use of Vaxfectin is described, e.g., in M Shlapobersky et al. Vaxfectin-adjuvanted seasonal influenza protein vaccine: correlation of systemic and local immunological markers with formulation parameters. *Vaccine* 2009 vol. 27: 6404-6410, which are hereby incorporated by reference in their entireties.

Liposomes are described, e.g., in U.S. Pat. Nos. 6,586,409, 6,638,621, 6,989,195, 6,991,809, 7,105,229, 7,105,574, 7,537,768, 7,582,613, 7,628,993, and 7655235, which are hereby incorporated by reference in their entireties.

Other Adjuvants

An adjuvant is an agent, pharmacological or immunological, that can modify the effect of another agent in a vaccine, without having an antigenic effect itself. Various adjuvants can be used to substitute for the pathogen components that elicit inflammatory responses. Use of an inexpensive adjuvant with specific activity targeting vaccine antigens to the most effective antigen-presenting cells can enhance the immune response without inducing undesirable inflammatory effects. An adjuvant can function in a variety of ways. For example, an adjuvant can act as a releasing agent, presenting an antigen over a period of time (depot adjuvant). A depot adjuvant can be, e.g., and oil emulsion. An adjuvant can be an irritant that amplifies and immune response. An adjuvant can also stabilize formulations of antigens. In one embodiment the pharmaceutical compositions described herein comprise one or more different adjuvants (e.g., 1, 2, 3, 4, 5, 6, 7, 8, 9, 10 or more).

In one embodiment, the adjuvant is a virosome. A virosome can comprise a unilamellar phospholipid bilayer vesicle that incorporates proteins derived from viruses that permit the virosome to fuse to target cells, e.g., cells of the immune system. A virosome can comprise a phospholipid bilayer membrane intercalated with viral envelope glycoproteins, e.g., influenza virus hemagglutinin (HA) and neuraminidase (NA). The HA and NA can confer structural stability and homogeneity to virosome particles. A virosome can be endocytosed by an antigen presenting cell, antigen synthesis/uptake can occur in the cell, the antigen can be proteolyzed, and the antigen can be presented on the cell for stimulation of T-cells. T-cell cytokines can stimulate B-cells to produce antibodies. Alternatively, if the antigen is displayed on the surface of the virosome, the antigen can directly stimulate B-cells to produce antibodies. A virosome can be provided by, e.g., Crucell, Pevion Biotech AG, or Virosome Biologicals B.V. In one embodiment the virosome-based vaccines include but are not limited to, Epaxal® or Inflexal®.

In another embodiment, the adjuvant is an inorganic adjuvant. For example, an adjuvant can be an aluminum salt. The aluminum salt can be, e.g., aluminum phosphate, aluminum hydroxide, aluminum potassium sulfate. An adjuvant can be calcium phosphate. Aluminum adjuvants can allow slow release of antigen In another embodiment, the adjuvant comprises squalene. Squalene is an organic polymer termed a triterpene.

In another embodiment, the adjuvant is an oil emulsion, products form bacteria, product from gram-negative bacteria, an endotoxin, cholesterol, fatty acids, aliphatic amines, or paraffinic or vegetable oil. In another embodiment, the adjuvant can be the oil-in water emulsion MF59, ASO2, or ASO3. MF59 is a sub-micron oil-in-water emulsion of a squalene, polyoxyethylene sorbitan moooleate (Tween 80) and sorbitan trioleate. The adjuvant can be ASO4 (aluminum and monophosphoryl lipid A).

In another embodiment, the adjuvant is Freund's adjuvant. Freund's adjuvant comprises a water-in-oil emulsion of aqueous antigen in paraffin (mineral) oil of low specific gravity and low viscosity. Drakeol 6VR and Arlacel A (mannide monoleate) can be used as emulsifiers. Incomplete Freund's adjuvant comprises water-in-oil emulsion without added mycobacteria. Complete Freund's adjuvant comprises water-in-oil emulsion with heat-killed *Mycobacterium tuberculosis* or butyricum added.

In another embodiment, microorganisms, or components of microorganisms, can be used as adjuvant including, e.g., *Bordetella pertussis* components, *Corenybacterium* derived P40 component, cholera toxin, and mycobacteria.

In another embodiment, the adjuvant is lipopolysaccharide (LPS).

In another embodiment, the adjuvant is a CpG oligodeoxynucleotides (CpG ODN). CpGs are short single-stranded synthetic DNA molecules that contain a cytosine "C" followed by a guanine "G". The "p" refers to the phosphodiester backbone of DNA, however some ODN can have a modified phosphorothioate (PS) backbone. When these CpG motifs are unmethlyated, they act as immunostimulants. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is expressed in B cells and plasmacytoid dendritic cells (pDCs) in humans and other higher primates. Numerous sequences have been shown to stimulate TLR9 with variations in the number and location of CpG dimers, as well as the precise base sequences flanking the CpG dimers. This led to the creation of five classes or categories of CpG ODN based on their sequence, secondary structures, and effect on human peripheral blood mononuclear cells (PBMCs). The five classes are Class A (Type D), Class B (Type K), Class C, Class P, and Class S. The Class A ODNS have structural features that include: the presences of a poly G sequence at the 5' end, the 3' end, or both; an internal palindrome sequence; GC dinucleotides contained within the internal palindrome; and a partially PS-modified backbone. In one embodiment the internal palindrome sequence can be 4 to 8 base pairs in length and vary in the order of bases. In one embodiment the palindrome sequence is 5'-Pu Pu CG Pu Py CG Py Py-3'. In one embodiment Class A CpG ODNs can induce the production of large amounts of Type I interferons (e.g. IFNa) or induce the maturation of peripheral dendritic cells (pDCs). The Class B ODNs have structural features that include: one or more timer CpG motif 5'-Pu Py C G Py Pu-3; a fully phosphorothioated (PS-modified) backbone; and are generally 18 to 28 nucleotides in length. are strong stimulators of human B cell and monocyte maturation. In one embodiment Class B ODNs stimulate human B cell and monocyte maturation. In another embodiment Class B ODNs stimulate the maturation of pDCs or the production of small amounts of IFNα.

In another embodiment, the adjuvant is an immunostimulating complexe (ISCOM). An ISCOM can be a stable but non-covalently-bound complex of saponin adjuvant Quil-A, cholesterol, and amphipathic antigen in a molar ratio of approximately 1:1:1.

In one embodiment, and adjuvant is a cytokine, e.g., interleukins such as interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), granulocyte colony stimulating factor (G-CSF) and erythropoietin, tumor necrosis factors (TNF) such as TNF alpha, lymphokines such as lymphotoxin, regulators of metabolic processes such as leptin, interferons such as interferon alpha, interferon beta, and interferon gamma, and chemokines, e.g., CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXC12, CXCL13, CXCL14, CXCL15, CXCL16, CXCL17, XCL1, XCL2, or CX3CL1. In one embodiment the cytokine can be expressed from a plasmid. In another embodiment, the cytokine can be provided as a polypeptide.

Other Agents/Formulations/Modes of Delivery

In one embodiment, a pharmaceutical composition comprises carriers and/or excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another embodiment, a pharmaceutical composition is substantially free of preservatives. In another embodiment, a pharmaceutical composition can contain at least one preservative. General methodology on pharmaceutical dosage forms is found in, e.g., in Ansel et al., Pharmaceutical Dosage Forms and Drug Delivery Systems (Lippencott Williams & Wilkins, Baltimore Md. (1999)), which is herein incorporated by reference in its entirety. While any suitable carrier known to those of ordinary skill in the art can be employed to administer the pharmaceutical composition, the type of carrier will vary depending on the mode of administration.

The concentration of components of the pharmaceutical composition, e.g., nucleic acid sequence of polypeptide, can be adjusted, the pH of the solution buffered and the isotonicity adjusted to be compatible with intravenous injection, as is well known in the art.

A pharmaceutical immunostimulatory agent (e.g., nucleic acid sequence or polypeptide) can be formulated as a sterile solution or suspension, in suitable vehicles, well known in the art. A pharmaceutical composition can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described, e.g., in Remington "The Science and Practice of Pharmacy" ($20^{th}$ Ed., Lippincott Williams & Wilkins, Baltimore Md.), the teachings of which are incorporated by reference in their entirety herein.

A pharmaceutical immunostimulatory agent (e.g., nucleic acid sequence or polypeptide) in a pharmaceutical composition can be provided alone or in combination with one or more other agents (e.g., adjuvants) or with one or more other forms. For example a formulation can comprise one or more agents in particular proportions, depending on the relative potencies of each agent and the intended indication. For example, in compositions comprising two different nucleic acid sequences, and where potencies are similar, about a 1:1 ratio of the nucleic acid sequences can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of an agent used in a pharmaceutical composition described herein, and which are not biologically or otherwise undesirable. For example, a pharmaceutically acceptable salt does not interfere with the beneficial effect of an agent in preventing, inhibiting, reducing the severity of, or treating a condition (e.g., malaria, cancer, Alzheimer's disease, bacterial infection, fungal infection, viral infection, parasite infection, etc.).

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if an agent contains a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of an agent used in a pharmaceutical composition described herein, and which are not biologically or otherwise undesirable. For example, the ester or amide does not interfere with the beneficial effect of an agent in preventing, inhibiting, reducing the severity of, or treating a condition (e.g., malaria, cancer, Alzheimer's disease, bacterial infection, fungal infection, viral infection, parasite infection, etc.). Esters can include, e.g., ethyl, methyl, isobutyl, ethylene glycol, and the like. Amides can include, e.g., unsubstituted amides, alkyl amides, dialkyl amides, and the like.

In another embodiment, a pharmaceutical immunostimulatory agent (e.g., nucleic acid sequence or polypeptide) can be administered in combination with one or more other compounds, forms, and/or agents, e.g., as described above. Pharmaceutical compositions comprising combinations of a nucleic acid sequence or polypeptide with one or more other active agents can be formulated to comprise certain molar ratios. For example, molar ratios of about 99:1 to about 1:99 of a nucleic acid sequence or polypeptide to the other active agent can be used. In some subset of the embodiments, the range of molar ratios of nucleic acid sequence or polypeptide: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of nucleic acid sequence or polypeptide: other active agent can be about 1:9, and in another embodiment can be about 1:1. Two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

In one embodiment, a pharmaceutical immunostimulatory agent (e.g., nucleic acid sequence or polypeptide) and/or combinations of agents can be administered with one or more agents with a therapeutic effect. In one embodiment the one or more other agents can be co-administered with the pharmaceutical immunostimulatory agent. In another embodiment the one or more other agents can be administered before or after the pharmaceutical immunostimulatory agent. In one embodiment the pharmaceutical immunostimulatory agent and the one or more other agents can be administered by the same route of delivery. In another embodiment the pharmaceutical immunostimulatory agent and the one or more other agents can be administered by different routes of delivery. The choice of agents that can be co-administered with the agents (e.g., nucleic acid sequence or polypeptide) and/or combinations of agents can depend, at least in part, on the condition being treated. Agents that can be used in the formulations described herein include, for example, any agent having a therapeutic effect for a condition (e.g., malaria, cancer, Alzheimer's disease, bacterial infection, fungal infection, viral infection, parasite infection, etc.), including, e.g., drugs used to treat inflammatory conditions.

In one embodiment an agent with a therapeutic effect can be an anti-inflammatory drugs, such as an NSAID, e.g., ibuprofen, naproxen, acetaminophen, ketoprofen, or aspirin. In another embodiment, an agent with a therapeutic effect can be an influenza antiviral agents, such as amantadine, rimantadine, zanamivir, and oseltamivir. In another embodiment, an agent with a therapeutic effect can be an antiviral drugs, such as protease inhibitors (lopinavir/ritonavir {Kaletra}, indinavir {Crixivan}, ritonavir {Norvir}, nelfinavir {Viracept}, saquinavir hard gel capsules {Invirase}, atazanavir {Reyataz}, amprenavir {Agenerase}, fosamprenavir {Telzir}, tipranavir{Aptivus}), reverse transcriptase inhibitors, including non-Nucleoside and Nucleoside/nucleotide inhibitors (AZT {zidovudine, Retrovir}, ddI {didanosine, Videx}, 3TC {lamivudine, Epivir}, d4T {stavudine, Zerit}, abacavir {Ziagen}, FTC {emtricitabine, Emtriva}, tenofovir {Viread}, efavirenz {Sustiva} and nevirapine {Viramune}), fusion inhibitors T20 {enfuvirtide, Fuzeon}, integrase inhibitors (MK-0518 and GS-9137), and maturation inhibitors (PA-457 {Bevirimat}). In another embodiment, an agent with a therapeutic effect can be an vitamin C, E or other anti-oxidants.

In one embodiment a formulations of a pharmaceutical composition described herein can contain one or more conventional anti-inflammatory drugs, such as an NSAID, e.g., ibuprofen, naproxen, acetaminophen, ketoprofen, or aspirin. In another embodiment, a formulations of a pharmaceutical composition described herein can described herein can additionally contain one or more conventional influenza antiviral agents, such as amantadine, rimantadine, zanamivir, and oseltamivir. In treatments for retroviral infections, such as HIV, a formulations of a pharmaceutical composition described herein can additionally contain one or more conventional antiviral drugs, such as protease inhibitors (lopinavir/ritonavir {Kaletra}, indinavir {Crixivan}, ritonavir {Norvir}, nelfinavir {Viracept}, saquinavir hard gel capsules {Invirase}, atazanavir {Reyataz}, amprenavir {Agenerase}, fosamprenavir {Telzir}, tipranavir{Aptivus}), reverse transcriptase inhibitors, including non-Nucleoside and Nucleoside/nucleotide inhibitors (AZT {zidovudine, Retrovir}, ddI {didanosine, Videx}, 3TC {lamivudine, Epivir}, d4T {stavudine, Zerit}, abacavir {Ziagen}, FTC {emtricitabine, Emtriva}, tenofovir {Viread}, efavirenz {Sustiva} and nevirapine {Viramune}), fusion inhibitors T20 {enfuvirtide, Fuzeon}, integrase inhibitors (MK-0518 and GS-9137), and maturation inhibitors (PA-457 {Bevirimat}). In another embodiment, a formulations of a pharmaceutical composition described herein can additionally contain one or more supplements, such as vitamin C, E or other anti-oxidants.

In one embodiment, an agent with a therapeutic effect is an anticancer agent. In one embodiment, the agent with a therapeutic effect is 13-cis-Retinoic Acid, 2-CdA, 2-Chlorodeoxyadenosine, 5-Azacitidine, 5-Fluorouracil, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex ®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea ®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone ®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®

In one embodiment, an agent is an Alzheimer's drug. In one embodiment, the Alzheimer's drug is Namenda (memantine), Razadyne (galantamine), Exelon (rivastigmine), Aricept (donepezil), or Cognex.

An agent (e.g., nucleic acid sequence of polypeptide) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the methods described herein can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the pharmaceutical compositions, kits, and methods described herein, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, a pharmaceutical immunostimulatory agent (e.g., nucleic acid sequence or polypeptide) can be formulated readily by combining the active agent(s) with pharmaceutically acceptable carriers well known in the art. Such carriers enable the agents described herein to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets can contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, an agent (e.g., nucleic acid sequence or polypeptide) will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use can contain a pharmaceutical immunostimulatory agents (e.g., nucleic acid sequence or polypeptide) with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In another embodiment, oils or non-aqueous solvents can be required to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl. Acad. Sci. USA 75: 4194-4198 (1978), incorporated herein by reference. Ligands can also be attached to the liposomes to direct these compositions to particular sites of action. A pharmaceutical immunostimulatory agent (e.g., nucleic acid sequence or polypeptide) can also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active agent (e.g., nucleic acid sequence or polypeptide) can be dissolved or suspended in suitable liquids, such as fatty oils, liquid paraffin, or liquid polyethylene glycols. In addition, stabilizers can be added. All formulations for oral administration can be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or can contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension can be made by adding the active compound to a concentrated, aqueous solution of a sugar, e.g., sucrose, to which can also be added any accessory ingredients. Such accessory ingredients can include flavoring, an agent to retard crystallization of the sugar or an agent to increase the solubility of any other ingredient, e.g., as a polyhydric alcohol, for example, glycerol or sorbitol.

When formulating a pharmaceutical immunostimulatory agent (e.g., nucleic acid sequence or polypeptide) for oral administration, it can be desirable to use gastroretentive formulations to enhance absorption from the gastrointestinal (GI) tract. A formulation which is retained in the stomach for several hours can release compounds of the invention slowly and provide a sustained release that can be used in methods of the invention. Disclosure of such gastro-retentive formulations are found in Klausner, E.A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques can be utilized to maximize absorption of the compounds of the invention.

A pharmaceutical immunostimulatory agent (e.g., nucleic acid sequence or polypeptide) can be formulated for parenteral administration (e.g., by injection, for example bolus injection or continuous infusion) and can be presented in unit dose form in ampoules, pre-filled syringes, small volume infusion or in multi-dose containers with an added preservative. The pharmaceutical compositions can take such forms as suspensions, solutions, or emulsions in oily or aqueous vehicles, for example solutions in aqueous polyethylene glycol. In one embodiment, the pharmaceutical immunostimulatory agent (e.g., nucleic acid sequence or polypeptide) is administered by parenteral injection (e.g., intravenous, subcutaneous, intramuscular, or intraperitoneal). In one embodiment the pharmaceutical immunostimulatory agent comprises a nucleic acid sequence encoding a fusion protein comprising an antigen or a fragment thereof and an immune cell product (e.g., MIP-3$\alpha$).

For injectable formulations, a vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In one embodiment, a pharmaceutical immunostimulatory agent (e.g., nucleic acid sequence or polypeptide) is administered by in vivo electroporation. In vivo electroporation can be performed with a syringe pre-loaded with nucleic acid sequence, polypeptide, and/or a pharmaceutical composition. The syringe and needle electrodes can be inserted into tissue, and the nucleic acid sequence, polypeptide, and/or pharmaceutical composition can be injected. A low micro-second electric pulse can be applied through the syringe needle. Electroporation can involve application of a millisecond electrical pulse, which can form an electric field. The electrical field can cause permeability is a cell membrane and can increase the uptake of biological material injected into local tissue. In vivo electroporation techniques are described, e.g., in U.S. Patent Application Nos. 20090156787 and 20050052630, which are hereby incorporated by reference in their entireties. Electroporation devices are also described in U.S. Pat. Nos. 7,245,963, 6,912,417, 6,319,901, 6,278,895, 6,041,252, 5,873,849, 6,117,660, or 6653114, which are hereby incorporated by reference in their entireties. In vivo electroporation can be performed with technology from Inovio Pharmaceuticals, Inc., Ichor Medical Systems, or Cyto Pulse Sciences (e.g., Easy Vax Clinical Epidermal Electroporation System).

The Easy Vax vaccine delivery system can deliver large molecules, using pulsed electric fields, directly in vivo into human skin cells to elicit an immune response against a specific target. The delivery system can include a single-use microneedle array in which each needle is coated with the polynucleotide. Hundreds of microneedles in the array can be aligned in 20 or more rows, with each row of needles dielectrically isolated. The array can be a few millimeters square and the needles can be <1 mm long. When inserted into the skin, there can be approximately 6200 epithelial cells and 25 Langerhans cells within the volume between any two rows when inserted 0.15 mm. The system can include a Waveform Generator that can apply a pulsed voltage (1-50 volts) from one row of needles to the next. The electric field established between the needle rows can permeabilize the membranes of the cells between the rows permitting polynucleotide or polypeptide to enter the cells. This system introduces several design features that can enhance immunization. First, the electrode needles are only 150-500μ long, ensuring that the majority of the needles do not penetrate significantly beyond the basal lamina of the skin. Second, the needles can be spaced close together, reducing the absolute voltage required to achieve cell membrane permeabilization. This can result in a painless delivery system and place the nucleic acid sequence or polypeptide at a site of abundant Langerhans cells to engage the proteins secreted by the cells that take up the DNA. The results of an experiment comparing immunization with vaccinia DNA using the Cyto-Pulse Easy Vax system vs. immunization using the standard scarification technique with live vaccinia demonstrated that equivalent ELISA and neutralization titers were obtained with either method (data not shown). Published studies also indicate a dramatic enhancement of the response to DNA encoding HBsAg when electroporation using the Easy Vax system is added to the immunization regimen.

A composition can be formulated in accordance with routine procedures as a pharmaceutical composition adapted for intravenous administration to human beings. Pharmaceutical compositions for intravenous administration can be solutions in sterile isotonic aqueous buffer. Where necessary, the pharmaceutical composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a pharmaceutical composition is to be administered by infusion, it can be dispensed with an infusion bottle containing sterile pharmaceutical grade water or saline. Where a pharmaceutical composition is administered by injection, an ampoule of sterile water for injection or saline can be provided so that the ingredients can be mixed prior to administration.

When administration is by injection, a pharmaceutical immunostimulatory agent (e.g., nucleic acid sequence or polypeptide) can be formulated in aqueous solutions, e.g., in physiologically compatible buffers such as Hanks solution, Ringer's solution, or physiological saline buffer. The solution can contain formulatory agents such as suspending, stabilizing and/or dispersing agents. An agent (e.g., nucleic acid sequence or polypeptide) can be in powder form for constitution with a suitable vehicle, e.g., sterile pyrogen-free water, before use. In another embodiment, a pharmaceutical composition does not comprise an adjuvant or any other substance added to enhance the immune response stimulated by an agent (e.g., nucleic acid sequence or polypeptide). In another embodiment, the pharmaceutical composition comprises a substance that inhibits an immune response an agent (e.g., nucleic acid sequence or polypeptide). Methods of formulation are known in the art, for example, as disclosed in Remington's Pharmaceutical Sciences, latest edition, Mack Publishing Co., Easton P.

In addition to the formulations described previously, a pharmaceutical immunostimulatory agent (e.g., nucleic acid sequence or polypeptide) can also be formulated as a depot preparation. Such long acting formulations can be administered by implantation or transcutaneous delivery (for example subcutaneously or intramuscularly), intramuscular injection or use of a transdermal patch. Thus, for example, an agent (e.g., nucleic acid sequence or polypeptide) can be formulated with suitable polymeric or hydrophobic materials (for example as an emulsion in an acceptable oil) or ion exchange resins, or as sparingly soluble derivatives, for example, as a sparingly soluble salt. A pharmaceutical composition can be self-administered.

In another embodiment, a pharmaceutical composition comprising one or more pharmaceutical immunostimulatory agents (e.g., nucleic acid sequence or polypeptide) exerts local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce, e.g., local and/or regional effects. Pharmaceutically appropriate vehicles for such formulation include, e.g., lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another embodiment, local/topical formulations comprising a nucleic acid sequence or polypeptide are used in preventing, inhibiting, reducing the severity of, or treating a condition (e.g., malaria, cancer, Alzheimer's disease, bacterial infection, fungal infection, viral infection, parasite infection, etc.).

A pharmaceutical composition can contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent (e.g., nucleic acid sequence or polypeptide) or combination of agents can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams can, e.g., be formulated with an aqueous or oily base with the addition of suitable thickening and/or gelling agents. Lotions can be formulated with an aqueous or oily base and can in general also contain one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139 which are hereby incorporated by reference in their entireties. Such patches can be constructed for continuous, pulsatile, or on demand delivery of pharmaceutical agents.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

A pharmaceutical compositions can treat prevent a disease or condition in a subject. A pharmaceutical compositions can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. A pharmaceutical composition can be prepared according to conventional methods. A pharmaceutical composition can be provided as a creams, milks, lotions, gels or foams for the face, for the hands, for the body and/or for the mucous membranes, or for cleansing the skin. A pharmaceutical composition can consist of solid preparations constituting soaps or cleansing bars.

A pharmaceutical composition can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants can be those conventionally used in the fields considered and, for example, can be from about 0.01% to about 20% of the total weight of the composition. Depending on their nature, these adjuvants can be introduced into the fatty phase, into the aqueous phase and/or into the lipid vesicles.

In another embodiment, an ocular infection can be effectively treated with ophthalmic solutions, suspensions, ointments or inserts comprising an agent (e.g., nucleic acid sequence or polypeptide) or combination of agents. Eye drops can be prepared by dissolving an agent (e.g., nucleic acid sequence or polypeptide) in a sterile aqueous solution such as physiological saline, buffering solution, etc., or by combining powder compositions to be dissolved before use. Other vehicles can be chosen, as are known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

A pharmaceutical composition can be packaged in multidose form. Preservatives can be used to prevent microbial contamination during use. Suitable preservatives include, e.g., benzalkonium chloride, thimerosal, chlorobutanol, methyl paraben, propyl paraben, phenylethyl alcohol, edetate disodium, sorbic acid, Onamer M, or other agents known to those skilled in the art. In ophthalmic products, such preservatives can be employed at a level of from 0.004% to 0.02%. In the compositions of the present application the preservative, e.g., benzalkonium chloride, can be employed at a level of from 0.001% to less than 0.01%, e.g. from 0.001% to 0.008%, preferably about 0.005% by weight. A concentration of benzalkonium chloride of 0.005% can be sufficient to preserve a pharmaceutical composition from microbial attack.

In another embodiment, an infection of the ear can be effectively prevented, inhibited, reduced, or treated with otic solutions, suspensions, ointments or inserts comprising a pharmaceutical immunostimulatory agent (e.g., nucleic acid sequence or polypeptide) or combination of agents.

In another embodiment, a pharmaceutical immunostimulatory agent (e.g., nucleic acid sequence or polypeptide) can be delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, can provide immediate, short-term exposure.

In another embodiment relating to topical/local application, a pharmaceutical composition can include one or more penetration enhancers. For example, a pharmaceutical composition can comprise suitable solid or gel phase carriers or excipients that increase penetration or help delivery of a pharmaceutical immunostimulatory agent (e.g., nucleic acid sequence or polypeptide) or combinations of agents across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, a-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In another embodiment, a pharmaceutical compositions can include one or more such penetration enhancers.

In another embodiment, a pharmaceutical composition for local/topical application can include one or more antimicrobial preservatives such as quaternary ammonium compounds, organic mercurials, p-hydroxy benzoates, aromatic alcohols, chlorobutanol, and the like.

Gastrointestinal infections can be effectively prevented, inhibited, reduced, or treated with orally- or rectally delivered solutions, suspensions, ointments, enemas and/or suppositories comprising an agent (e.g., nucleic acid sequence or polypeptide) of the present invention.

Respiratory infections can be effectively prevented, inhibited, reduced, or treated with aerosol solutions, suspensions or dry powders comprising an agent (e.g., nucleic acid sequence or polypeptide) or combination of agents. Administration by inhalation can be useful in treating viral infections of the lung. The aerosol can be administered through the respiratory system or nasal passages. For example, one skilled in the art will recognize that a pharmaceutical composition can be suspended or dissolved in an appropriate carrier, e.g., a pharmaceutically acceptable propellant, and administered directly into the lungs using a nasal spray or inhalant. For example, an aerosol formulation comprising an agent (e.g., nucleic acid sequence or polypeptide) can be dissolved, suspended or emulsified in a propellant or a mixture of solvent and propellant, e.g., for administration as a nasal spray or inhalant. Aerosol formulations can contain any acceptable propellant under pressure, such as a cosmetically or dermatologically or pharmaceutically acceptable propellant, as conventionally used in the art.

An aerosol formulation for nasal administration can generally be an aqueous solution designed to be administered to the nasal passages in drops or sprays. Nasal solutions can be similar to nasal secretions in that they can be isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that an agent (e.g., nucleic acid sequence or polypeptide) or combination of agents can be carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998 which are hereby incorporated by reference in their entireties. Hydrocarbon propellants can include, e.g., propane, isobutane, n-butane, pentane, isopentane and neopentane. A blend of hydrocarbons can also be used as a propellant. Ether propellants can include, e.g., dimethyl ether as well as the ethers. An aerosol formulation can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. A pharmaceutical composition can also be dispensed with a compressed gas, e.g., an inert gas such as carbon dioxide, nitrous oxide or nitrogen.

Aerosol formulations can also include other components, e.g., ethanol, isopropanol, propylene glycol, as well as surfactants or other components such as oils and detergents. These components can serve to stabilize the formulation and/or lubricate valve components.

An aerosol formulation can be packaged under pressure and can be formulated as an aerosol using solutions, suspensions, emulsions, powders and semisolid preparations. For example, a solution aerosol formulation can comprise a solution of a pharmaceutical immunostimulatory agent (e.g., nucleic acid sequence or polypeptide) in (substantially) pure propellant or as a mixture of propellant and solvent. The solvent can be used to dissolve the pharmaceutical immunostimulatory agent (e.g., nucleic acid sequence or polypeptide) and/or retard the evaporation of the propellant. Solvents useful can include, e.g., water, ethanol and glycols. Any combination of suitable solvents can be used, optionally combined with preservatives, antioxidants, and/or other aerosol components.

An aerosol formulation can also be a dispersion or suspension. A suspension aerosol formulation can comprise a suspension of a pharmaceutical immunostimulatory agent (e.g., nucleic acid sequence or polypeptide) or combination of agents, and a dispersing agent. Dispersing agents can include, e.g., sorbitan trioleate, oleyl alcohol, oleic acid, lecithin and corn oil. A suspension aerosol formulation can also include lubricants, preservatives, antioxidant, and/or other aerosol components.

An aerosol formulation can be formulated as an emulsion. An emulsion aerosol formulation can include, e.g., an alcohol such as ethanol, a surfactant, water and a propellant, as well as an agent (e.g., nucleic acid sequence or polypeptide) or combination of agents. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

A pharmaceutical composition can be formulated for administration as suppositories. A low melting wax, such as a mixture of triglycerides, fatty acid glycerides, Witepsol S55 (trademark of Dynamite Nobel Chemical, Germany), or cocoa butter can be first melted and the active component can be dispersed homogeneously, e.g., by stirring. The molten homogeneous mixture can then be poured into convenient sized molds, allowed to cool, and to solidify. 1002111A pharmaceutical composition can be formulated for vaginal administration. Pessaries, tampons, creams, gels, pastes, foams or sprays containing, in addition to an active ingredient, such carriers as are known in the art to be appropriate.

An agent (e.g., nucleic acid sequence or polypeptide) can be attached releasably to biocompatible polymers for use in sustained release formulations on, in or attached to inserts for topical, intraocular, periocular, or systemic administration. The controlled release from a biocompatible polymer can be used with a water soluble polymer to form a instillable formulation. The controlled release from a biocompatible polymer, such as as, e.g., PLGA microspheres or nanospheres, can be used in a formulation suitable for intra ocular implantation or injection for sustained release administration. Any suitable biodegradable and biocompatible polymer can be used.

A pharmaceutical compositions can include compositions wherein a pharmaceutical immunostimulatory agent (e.g., nucleic acid sequence or polypeptide) is present in an effective amount, i.e., in an amount effective to achieve therapeutic and/or prophylactic benefit in a subject. The actual amount effective for a particular application will depend on the condition or conditions being treated, the condition of the subject, the formulation, and the route of administration, as well as other factors known to those of skill in the art. Determination of an effective amount of an agent (e.g., nucleic acid sequence or polypeptide) is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present invention appropriate for humans.

The effective amount when referring to an agent (e.g., nucleic acid sequence or polypeptide) or combination of agents can generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

Appropriate doses for an agent (e.g., nucleic acid sequence or polypeptide) can be determined based on in vitro experimental results. For example, the in vitro potency of an agent can provide information useful in the development of effective in vivo dosages to achieve similar biological effects.

In one embodiment, a pharmaceutical composition comprising a nucleic acids sequence encoding an antigen protein or a fragment thereof fused to a human chemokine and a liposomal adjuvant is administered to a human subject at sufficient dosage and frequency to treat or prevent a disease or condition. In one embodiment the pharmaceutical composition is administered to the human subject once every two days, every three days, every five days, once a week, once every two weeks, once or twice a month, once a year, twice a year, three times a year, four times a year, five times a year, six times a year, seven times a year, 8 times a year, 9 times a year, 10 times a year, 11 times a year, 12 times a year, once a decade, twice a decade, three times a decade. In another embodiment the pharmaceutical composition is administered to the human subject 1-3× a week, 4-7× a week, 1-5× a month, 5-10× a month, 1-10× over six months, 10-20× over six months, 1-12× a year or 12-24× a year. In another embodiment the pharmaceutical composition is administered to the human subject once a week for 1, 2, 3, 4, 5, or 6 weeks, once every other week for 3, 6, 9, 12, or 15 weeks, once a month for 1, 2, 3, 4, 5, or 6 months, once every other month for 3, 6, 9, 12, or 15 months.

In another embodiment, a pharmaceutical composition comprising a nucleic acids sequence encoding an antigen protein or a fragment thereof fused to a human chemokine and a liposomal adjuvant is administered to a non-human subject at sufficient dosage and frequency to treat or prevent a disease or condition. In one embodiment the pharmaceutical composition is administered to the non-human subject once every two days, every three days, every five days, once a week, once every two weeks, once or twice a month, once a year, twice a year, three times a year, four times a year, five times a year, six times a year, seven times a year, 8 times a year, 9 times a year, 10 times a year, 11 times a year, 12 times a year, once a decade, twice a decade, three times a decade. In another embodiment the pharmaceutical composition is administered to the non-human subject 1-3× a week, 4-7× a week, 1-5× a month, 5-10× a month, 1-10× over six months, 10-20× over six months, 1-12× a year or 12-24× a year. In another embodiment the pharmaceutical composition is administered to the non-human subject once a week for 1, 2, 3, 4, 5, or 6 weeks, once every other week for 3, 6, 9, 12, or weeks, once a month for 1, 2, 3, 4, 5, or 6 months, once every other month for 3, 6, 9, 12, or 15 months.

In another embodiment, a pharmaceutical composition comprising (e.g., nucleic acid sequence or polypeptide) and an adjuvant can be administered to a mammalian subject intermittently, for example administration at least once every two days, every three days, every five days, once a week, once every two weeks, once or twice a month, once a year, twice a year, three times a year, four times a year, five times a year, six times a year, seven times a year, 8 times a year, 9 times a year, 10 times a year, 11 times a year, 12 times a year, once a decade, twice a decade, three times a decade, and the like. In another embodiment, the pharmaceutical composition can be administered at least once a day, twice a day, three times a day, four times a day, five times a day, six times a day, eight times a day, nine times a day, ten times a day, or more.

In another embodiment, the amount, form of pharmaceutical composition, and/or amounts of the different forms of pharmaceutical composition can be varied at different times of administration. A pharmaceutical composition can be administered to a subject once a month, once a year, or once a decade.

Regulatory T Cell Inhibitor

In one embodiment, a pharmaceutical composition can comprise a regulatory T cell inhibitor. In another embodiment a regulatory T cell inhibitor can be administered to a human or non-human subject affected by or at risk of being affected by a disease or condition. In another embodiment a regulatory T cell inhibitor can be administered with a pharmaceutical composition disclosed herein to a human or non-human subject affected by or at risk of being affected by a disease or condition. A regulatory T can also be known as a $T_{reg}$ cell or suppressor T cell). A regulatory T cell can suppress activation of the immune system. A regulatory T cell can help an organism maintain tolerance to self-antigens. Regulatory T cells can express CD8 (CD8+), CD4, CD25, and Foxp3. The T regulatory cell inhibitory agent can be, for example, ONTAK, HuMax-Tac, Zenapax, or MDX-010 or a combination thereof. The $T_{reg}$ agent can comprise an antibody, or a fragment thereof, which specifically binds to a T regulatory cell surface protein. The T regulatory cell surface protein can be, for example, CD25 or CTLA4. The antibody, or fragment thereof, can further comprise a radionuclide or toxic moiety such that the antibody can kill the T regulatory cell. Antibodies that comprise a Treg agent can target a surface protein of the Treg cell, which include, for example, CD25, CD4, CD28, CD38, CD62L (selectin), OX-40 ligand (OX-40L), CTLA4, CCR4, CCR8, FOXP3, LAG3, CD103, NRP-1, or glucocorticoid-induced TNF receptor (GITR). The Treg agent can comprise a fusion protein, and the fusion protein can comprise a targeting moiety and a toxic moiety. The targeting moiety can comprise a ligand or portion thereof of a regulatory T cell surface protein. The ligand can be, for example, IL2, T cell receptor (TCR), MHCII, CD80, CD86, TARC, CCL17, CKLF1, CCL1, TCA-3, eotaxin, TER-1, E-cadherin, VEGF, semaphorin3a, CD134, CD31, CD62, CD38L, or glucocorticoid-induced TNF receptor ligand (GITRL). The toxic moiety can comprise, for example, lectin, ricin, abrin, viscumin, modecin, diphtheria toxin, cholera toxin, gelonin, Pseudomonas exotoxin, Shigella toxin, botulinum toxin, tetanus toxin, calicheamicin, or pokeweed antiviral protein. A regulatory T cell inhibitor can be, for example, an shRNA, siRNA, miRNA, antisense RNA, or ribozyme. Regulatory T cell inhibitors are described, e.g., in U.S. Patent Application No. 20090214533, which is hereby incorporated by reference in its entirety.

V. Methods of Treatment or Prevention

In another aspect, methods of using pharmaceutical compositions and kits comprising a pharmaceutical immunostimulatory agent (e.g., nucleic acid sequence or polypeptide) to prevent, inhibit, reduce the severity of, or treat a condition are provided. In one embodiment, a method is provided to use pharmaceutical compositions or kits to prevent, inhibit, reduce the severity of, or treat a condition of an animal subject. The term "animal subject" as used herein includes humans as well as other mammals, e.g., mouse, cow, horse, camel, gorilla, chimpanzee, rabbit, pig, dog, cat, camel, rat, elephant, deer, rhinoceros, bear, weasel, seal, whale, dolphin, porpoise, bat, shrew, mole, hedgehog, squirrel, chipmunk, gopher, monkey, lemur, anteater, sloth, armadillo, manatee, sea cow, or aardvark.

The condition can be a disease or condition e.g., cancer, Alzheimer's disease, viral infection, bacterial infection, fungal infection, parasite infection, e.g., malaria.

The term "treating" as used herein includes achieving a therapeutic benefit and/or a prophylactic benefit. By therapeutic benefit is meant eradication or amelioration of a condition. Also, a therapeutic benefit can be achieved with the eradication or amelioration of one or more of the physiological symptoms associated with the underlying condition such that an improvement is observed in the animal subject, notwithstanding the fact that the animal subject can still be afflicted with the underlying condition.

For embodiments where treatment of a subject is desired, a pharmaceutical composition disclosed herein can be administered to a patient with a disease or condition, such as cancer, Alzheimer's disease, viral infection, bacterial infection, fungal infection, parasite infection, e.g., malaria, or to a patient reporting one or more of the physiological symptoms of a condition, even though a diagnosis of the condition may not have been made. Administration of a pharmaceutical composition disclosed herein can treat, reduce, lessen, shorten and/or otherwise ameliorate the disease or condition. In one embodiment the pharmaceutical composition produces an immune response to an antigen sufficient to treat infection by a disease or condition comprising the antigen. In one embodiment the pharmaceutical composition can modulate the immune system.

For embodiments where a prophylactic benefit is desired (e.g., prevention), a pharmaceutical composition of the invention can be administered to a patient at risk of developing condition, such as cancer, Alzheimer's disease, viral infection, bacterial infection, fungal infection, parasite infection, e.g., malaria, or to a patient reporting one or more of the physiological symptoms of a condition, even though a diagnosis of the condition may not have been made. Administration can prevent the condition from developing, or it can reduce, lessen, shorten and/or otherwise ameliorate the disease or condition that develops. In one embodiment the pharmaceutical composition produces an immune response to an antigen sufficient to prevent infection by a disease comprising the antigen or development of a condition comprising the antigen. In one embodiment the pharmaceutical composition can modulate the immune system.

Provided herein also are kits that can be used to prevent, inhibit, reduce the severity of, or treat a condition. These kits comprise a pharmaceutical immunostimulatory agent (e.g., nucleic acid sequence or polypeptide) and some embodiments instructions teaching the use of the kit according to the various methods and approaches described herein. Such kits can also include information, such as scientific literature references, package insert materials, clinical trial results, and/or summaries of these and the like, which indicate or establish the activities and/or advantages of the agent. Such information can be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

In another aspect, a kit is provided comprising a nucleic acid sequence encoding a parasite antigen fused to an immune cell product; and an adjuvant. In one embodiment, the adjuvant is a liposome. In another embodiment, the liposome is Vaxfectin.

In another aspect, a kit is provided comprising a polypeptide comprising a parasite antigen fused to an immune cell product, and an adjuvant. In one embodiment, the adjuvant is a liposome. In another embodiment, the liposome is Vaxfectin.

In one embodiment, administering a pharmaceutical composition to a subject comprising a nucleic acid sequence encoding a malaria antigen fused to an immune cell product, e.g., MIP-3α, and an adjuvant, e.g., a liposome comprising a commixture of GAP-DMORIE and DPyPE, results in a synergistic reduction in liver stage parasites in a mammal infected with a malaria parasite relative to the sum of the effects of administration of a pharmaceutical composition comprising an adjuvant with a nucleic acid sequence that encodes the antigen without the immune cell product and a pharmaceutical composition comprising a nucleic acid encoding an antigen fused to an immune cell product but without the adjuvant.

In another aspect, a kit is provided comprising a nucleic acid sequence encoding an antigen fused to MIP-3α, and an adjuvant. In one embodiment, the adjuvant is a liposome. In another embodiment, the liposome is Vaxfectin.

In another aspect, a kit is provided comprising a nucleic acid sequence encoding circumsporozoite protein or protein fragment from *Plasmodium falciparum* fused to MIP-3α, and an adjuvant. In one embodiment, the adjuvant is a liposome. In another embodiment, the liposome is Vaxfectin.

VI. Non-Human Animal Models

Exemplary non-human animals that can be used to study the nucleic acid sequences, polypeptides, and pharmaceutical compositions described herein can include mice, rats, guinea pigs, hamsters, sheep, pigs, and primates. Mouse models can be used to study malaria. In one embodiment, the non-human animal is an immunocompromised mouse, e.g., an immunocompromised mouse transgenic for urokinase-type plasminogen activator (uPA), e.g., an immunocompromised mouse comprising a transgene that provides for liver-specific production of uPA (e.g., an Alb-uPA transgene, see, e.g., Heckel et al Cell 62:447 (1990)). Mice that can be used to study the nucleic acid sequences, polypeptides, and pharmaceutical compositions described herein include the strains C.B-17, C3H, BALB/c, C57131/6, AKR, BA, B10, 129, etc. The animal can be male or female.

BALB/c mice can be used to study infections, e.g., malaria infection. BALB/c mice are albino, laboratory-bred strain of mice that can be used for both cancer and immunology research. C57BL/6 mice can be used to study infections, e.g., malaria infection. JAX® Mice strain NOD.Cg-Prkdc$^{scid}$ Il2rg$^{tm1Wjl}$/SzJ, 005557, abbreviated NSG for NOD scid gamma, a NOD scid strain with a null mutation of the interleukin 2 receptor gamma (IL2rg) chain, can be used to study antimalarial drugs. See e.g., Jimenez-Diaz et al. *Antimicrob Agents Chemother*. Vol. 53, pp. 4533-6 (2009). Other mouse models for studying malaria infection are described, e.g., in Angulo-Barturen I. et al. *PLoS One*, vol. 3 e2252 (2008), and Mohmmed A. Biochem *Biophys Res Commun*. Vol. 309 pp. 506-11 (2003), which are hereby incorporated by reference in their entireties.

Mouse models for studying malaria are described, e.g., in U.S. Pat. No. 7,273,963, which is hereby incorporated by reference in its entirety.

Mouse models are available for studying cancer. Mouse models for studying cancer are disclosed in, e.g., *Nature Reviews Cancer*, vol. 7, pp. 654-658 (2007) which is hereby incorporated by reference in its entirety.

1002381A mouse model of Alzheimer's disease is described, e.g., in Koldamova R P et al. *Journal of Biological Chemistry* vol. 280, 4079-4088 (2005) which is hereby incorporated by reference in its entirety.

A mouse model used to study herpes simplex virus infection is described, e.g., in Tuyama ACG. Et al. *The Journal of Infectious Diseases* vol. 194, pp. 795-803 (2006) which is hereby incorporated by reference in its entirety.

A mouse model used to study hepatitis infection is described, e.g., in Morrissey D V. et al. *Hepatology* vol. 41, pp. 1349-1356 (2005) which is hereby incorporated by reference in its entirety.

Animal models used to study simian immunodeficiency virus (SIV), related to HIV, include rhesus macaques. See e.g., Ambrose Z. et al. *Trends in Biotechnology* vol. 25, pp. 33-337 (2007) which is hereby incorporated by reference in its entirety.

Guinea pigs models used to study influenza virus are described, e.g., in Mubareka S. et al. *The Journal of Infectious Diseases*, vol. 199 pp. 858-865 (2009) which is hereby incorporated by reference in its entirety.

EXAMPLES

Example 1

Figure 2:
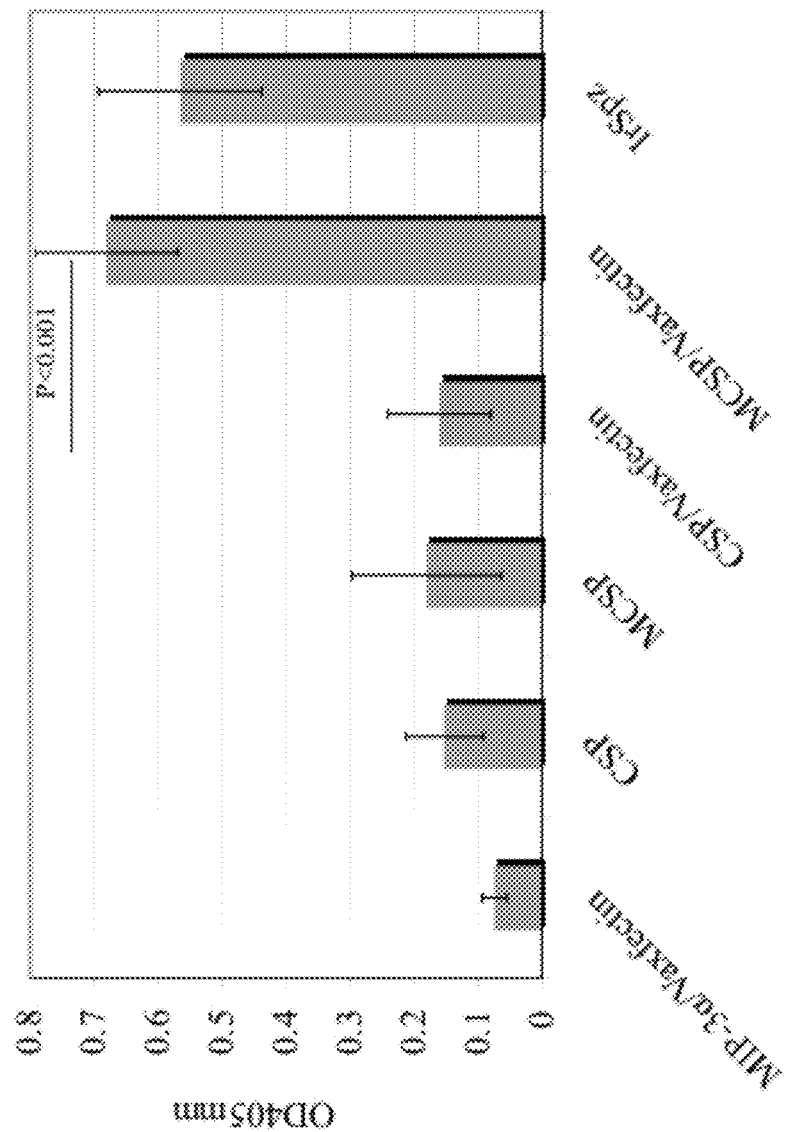
FIG. 2 illustrates ELISA for antibody response.
Figure 3:
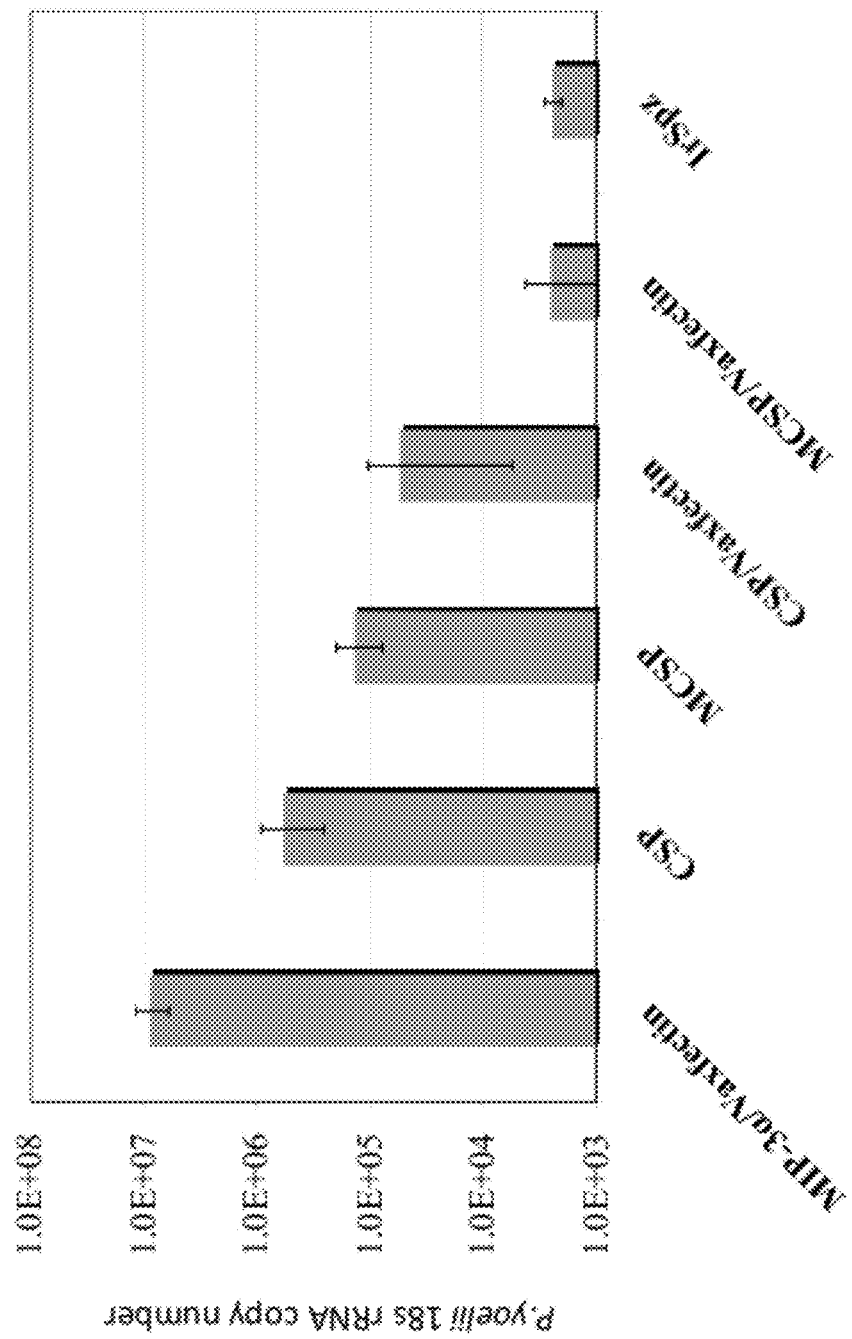
FIG. 3 illustrates protective efficacy against sporozoites challenge.
Figure 4:
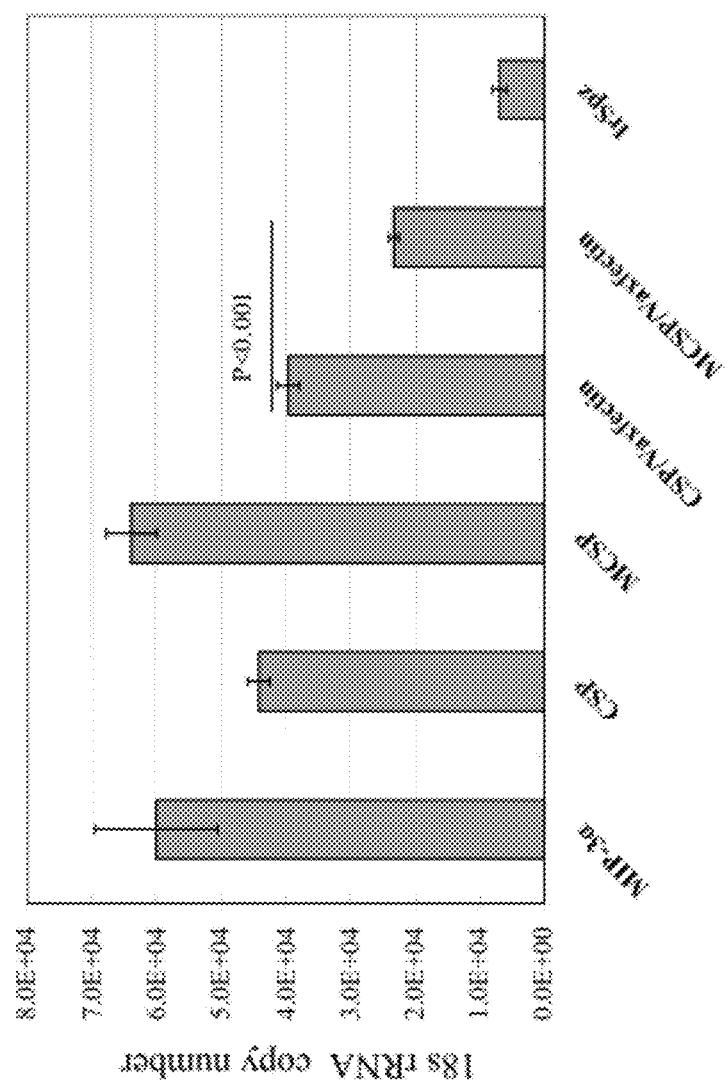
FIG. 4 illustrates results of a neutralization assay.

C57BL/6 mice were immunized with 2 µg of the constructs (FIG. 1), and were delivered as single injection in 100 µl of PBS or PBS formulated with Vaxfectin. Mice received three immunizations at bi-weekly intervals (i.e. over 6 weeks). For the control group, $10^5$ (initial immunization) and $5 \times 10^4$ (booster immunizations) irradiated *P. yoelii* sporozoites (17XN) were inoculated by tail-vein injection at the same time-points. All challenges were accomplished by injecting $5 \times 10^3$ sporozoites in the tail vein two weeks after last immunization. Results for antibody responses are illustrated in FIG. 2; results for protective efficacy against sporozoites challenge are illustrated in FIG. 3; and results for antibody neutralization activity are illustrated in FIG. 4.

Example 2

Figure 5:
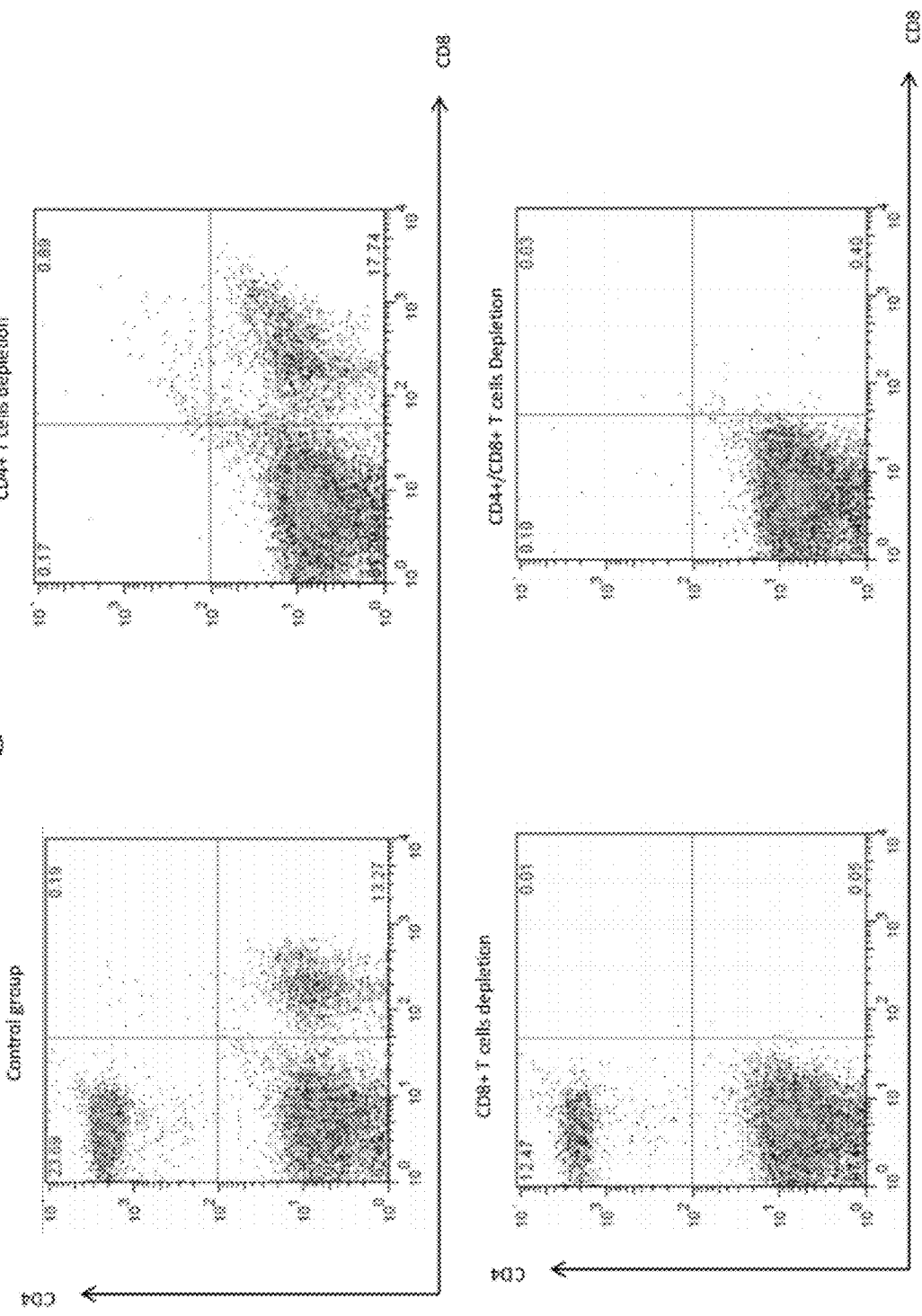
FIG. 5 illustrates the efficacy of the depletion estimated by two-color flow cytometry analysis of peripheral blood lymphocytes using FITC-conjugated anti-CD4 or APC-conjugated anti-CD8 mAbs.
Figure 6:
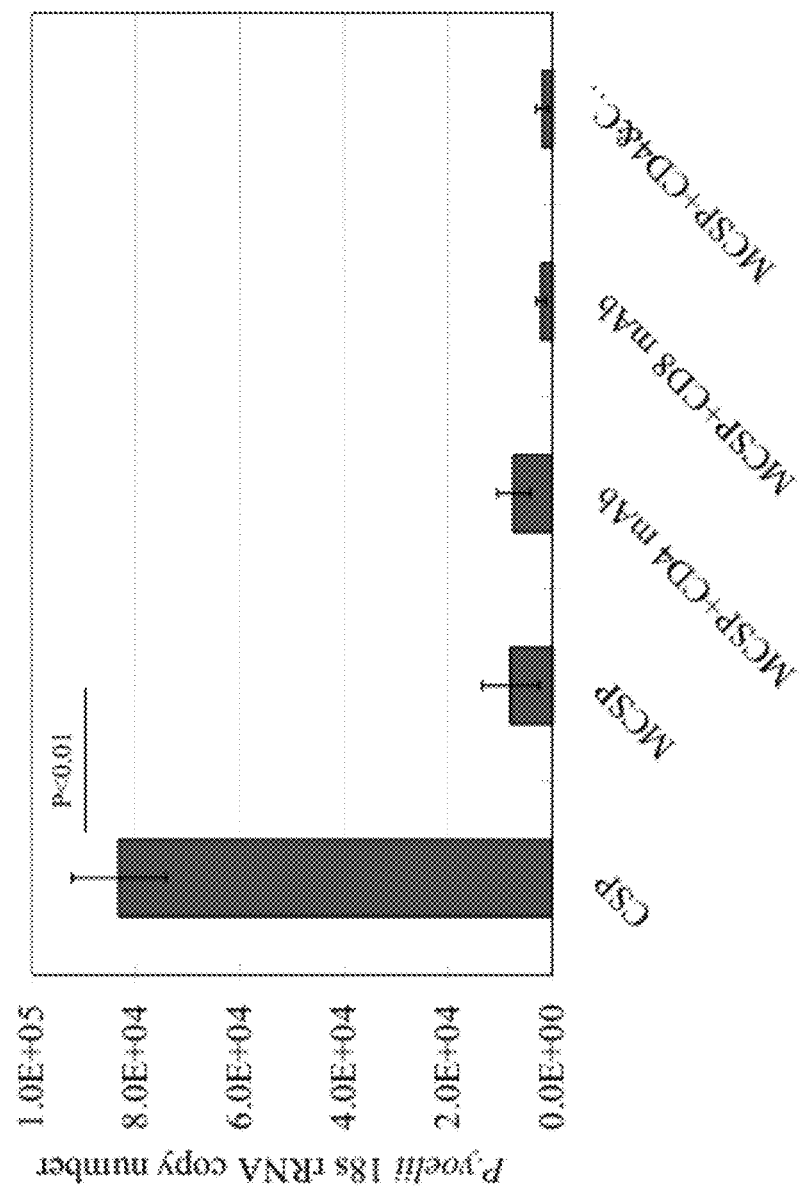
FIG. 6 illustrates protection mediated by immunization with Vaxfectin-formulated CSP or MCSP after T cell depletion prior to challenge.
Figure 7:
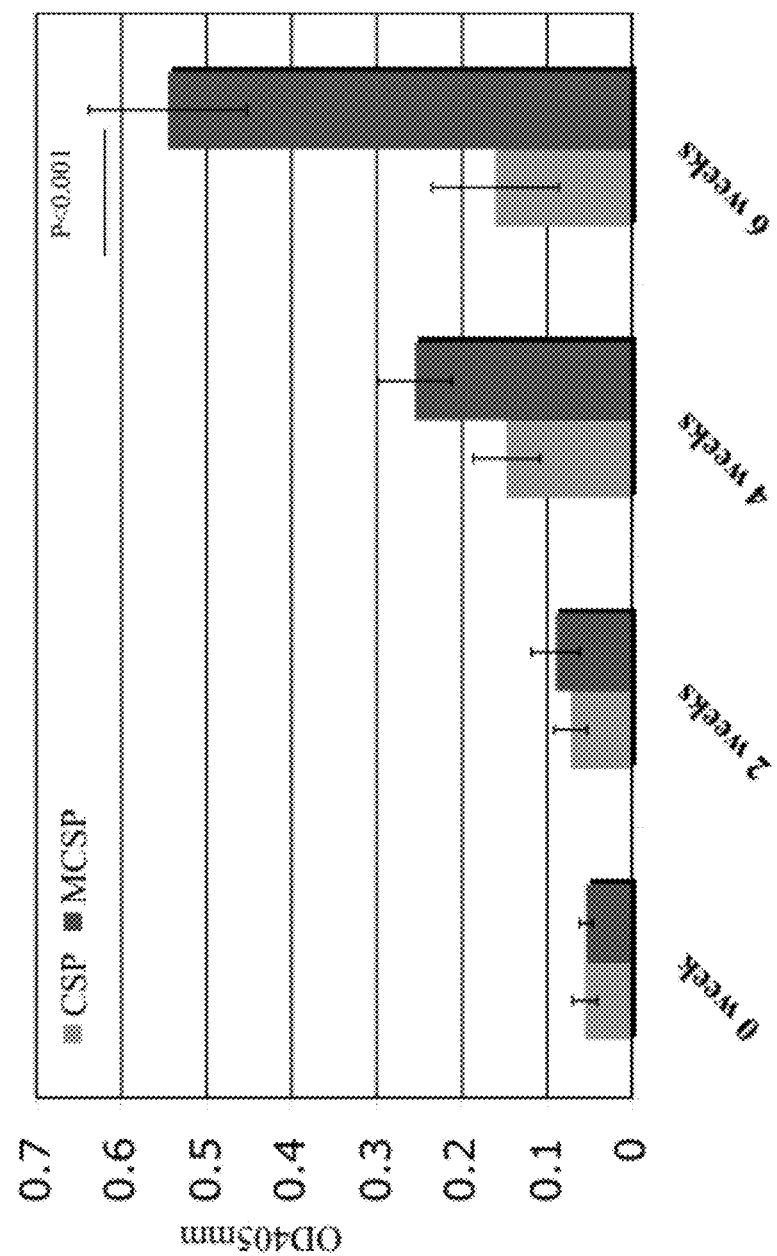
FIG. 7 illustrates antibody response from mice immunized with Vaxfectin-formulated with CSP and MCSP.
Figure 8:
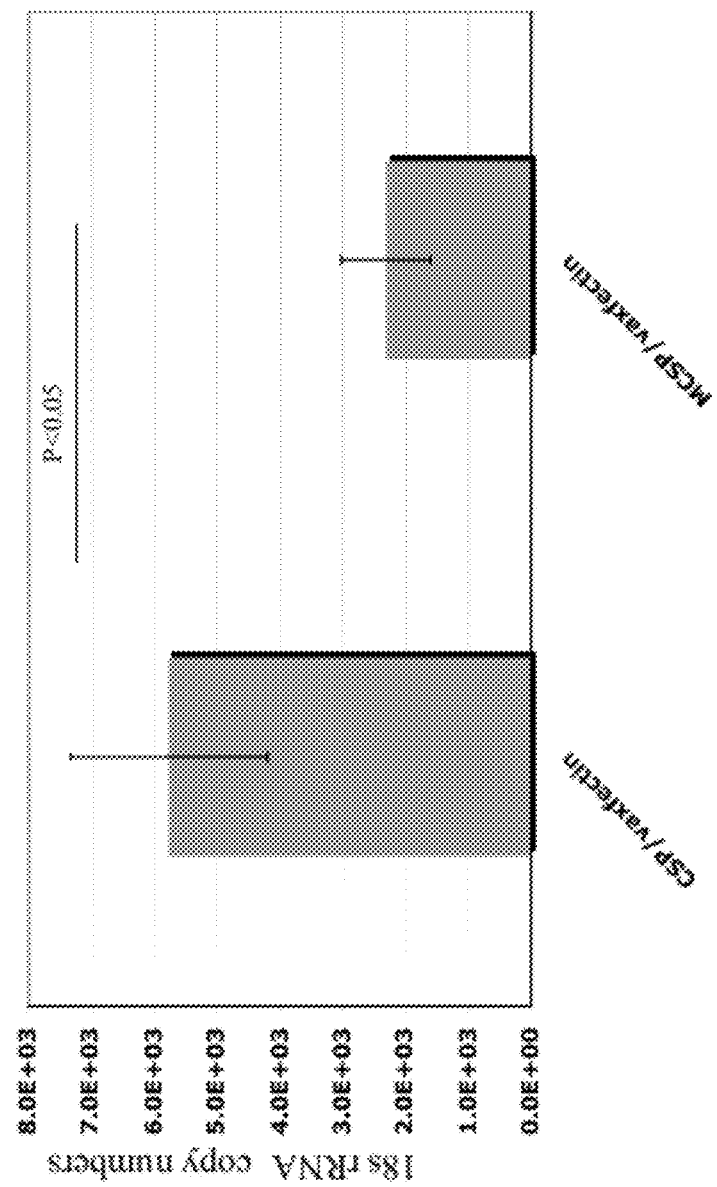
FIG. 8 illustrates antibody neutralization activity.

C57BL/6 mice were immunized with 2 µg of pCSP or pMCSP constructs (see FIG. 1) and were delivered as single injection in 100 µl of PBS formulated with Vaxfectin. Mice received three immunizations at bi-weekly intervals (i.e. over 6 weeks). To deplete the CD4+, CD8+, or both T cell subsets, immunized mice were injected (intraperitoneal; i.p) with anti-CD4, anti-CD8, or both mAbs two weeks after last immunization. Twenty four hours later, the efficacy of the depletion was estimated by two-color flow cytometry analysis of peripheral blood lymphocytes using FITC-conjugated anti-CD4 or APC-conjugated anti-CD8 mAbs (FIG. 5). Data show the CD4 and CD8 expression on combined peripheral lymphocytes of three mice in each group. Sporozoites challenge was performed by injecting 2500 sporozoites in mice tail vein. FIG. 6 illustrates protection mediated by immunization with Vaxfectin-formulated CSP or MCSP. Antibody response is illustrated in FIG. 7 and antibody neutralization activity is illustrated in FIG. 8.

Example 3

Figure 9:
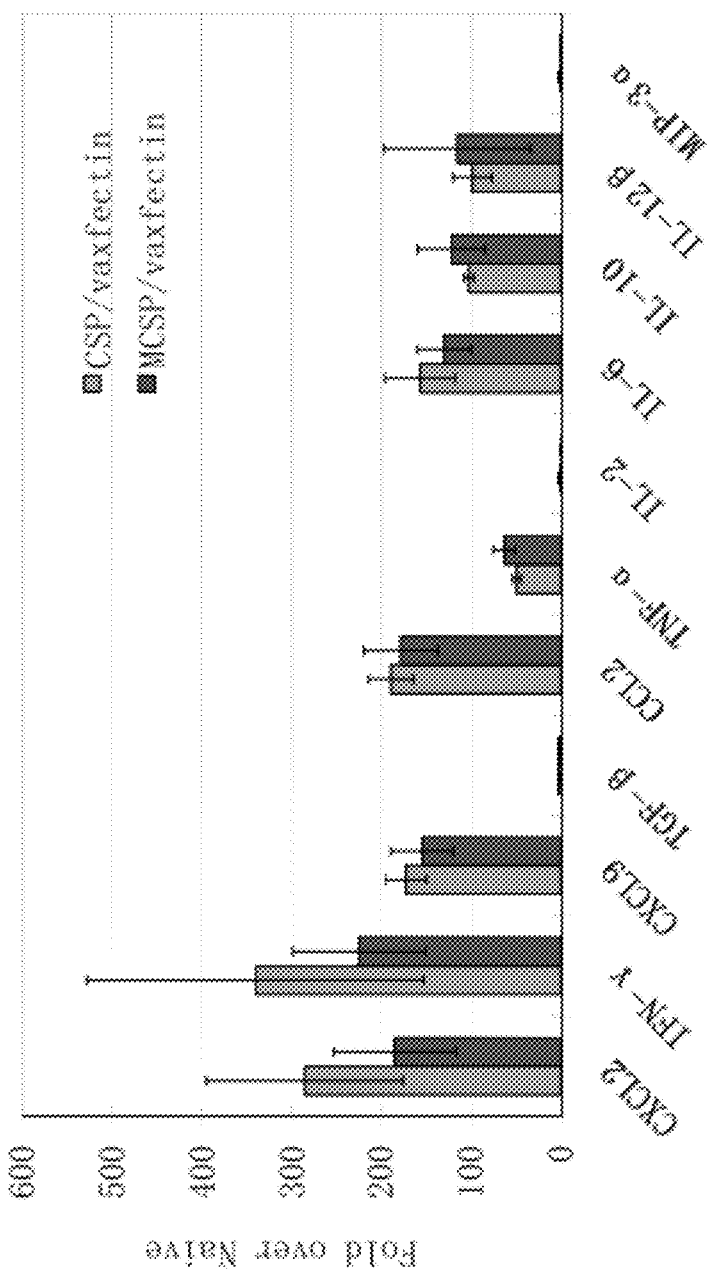
FIG. 9 illustrates real-time PCR evaluation of expression levels of cytokines at site of immunization (24 h after immunization).
Figure 10:
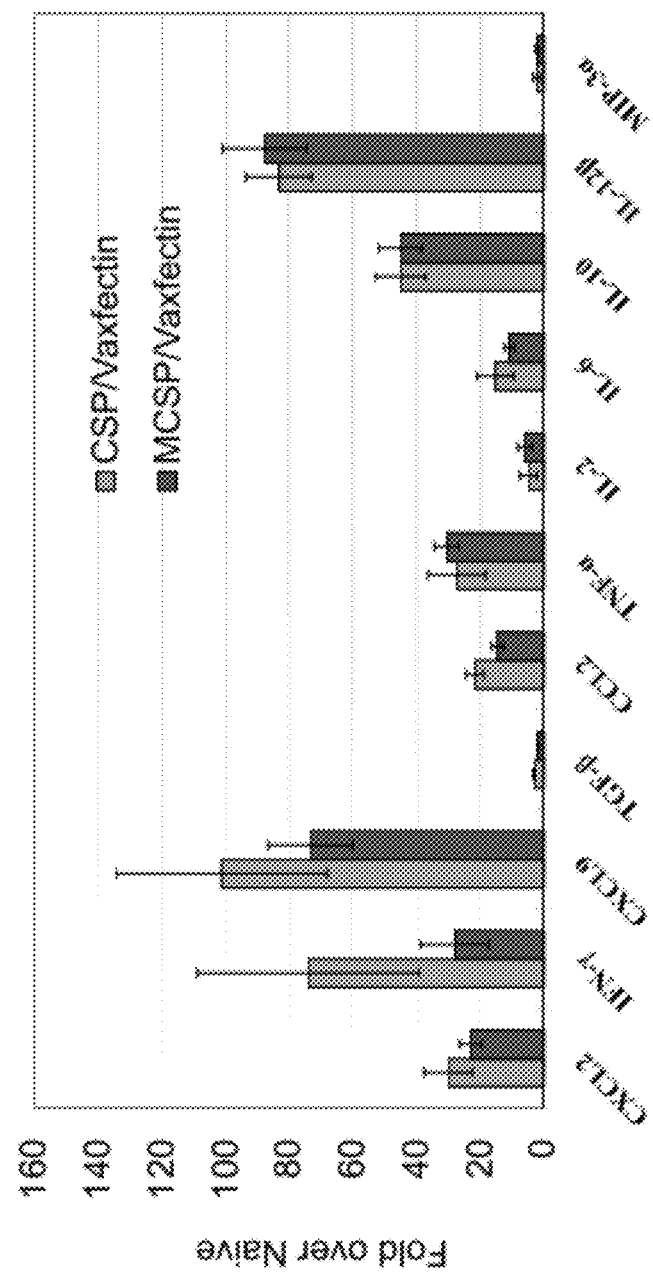
FIG. 10 illustrates real-time PCR evaluation of expression levels of cytokine at site of immunization (48 hr after immunization).

C57BL/6 mice were immunized with 100 µl PBS or 2 µg of Vaxfectin formulated plasmids DNA (100 µl) (see FIG. 1). 24 or 48 hours later, injected muscles are harvested and total RNA is isolated. Indicated cytokine or chemokine levels were analyzed by real-time PCR. FIG. 9 illustrates real-time PCR evaluation of expression levels of cytokines (24 h after immunization). FIG. 10 illustrates real-time PCR evaluation of expression levels of cytokines (48 h after immunization).

Example 4

Materials and methods. Experiments in examples 1-3 were performed using the materials and methods described below.

Mice

Six- to eight-week-old female BALB/c (H-2d) mice or C57BL/6 (H-2b) mice were purchased from The Jackson Laboratory (Bar Harbor, Me.) and maintained in a pathogen-free micro-isolation facility in accordance with the National Institutes of Health guidelines for the humane use of laboratory animals. All experimental procedures involving mice were approved by the Institutional Animal Care and Use Committee of the Johns Hopkins University.

Plasmids

The plasmid DNAs encoding *P. yoelii* circumsporozoite protein (pCSP) fused with MIP-3α (pCSP) are described in FIG. 1. Plasmid encoding MIP-3α is used as negative control. Plasmids were purified using Endofree purification columns (Qiagen, Hilden, Germany) and stored at −20° C. in PBS.

Vaxfectin Formulation

Formulations were prepared by adding 2 ml of 0.9% NaCl solution in 2.18 mg of Vaxfectin (Vical, San Diego, Calif.). Then, the same volumes of 1 mg/ml DNA and Vaxfectin were mixed, and the mixture was diluted to the desired concentration with PBS.

Immunization

BALB/c mice or C57BL/6 mice were immunized with 2 ug of the constructs described above, which were delivered as single injection in 100 ul of PBS formulated with Vaxfectin. Mice received three immunizations at bi-weekly intervals (over 6 weeks). For the control group, $10^5$ (initial immunization) and $5 \times 10^4$ (booster immunizations) irradiated *P. yoelii* sporozoites (17XN) obtained from *Anopheles stephensi* maintained in the Johns Hopkins Malaria Research Institute insectary were inoculated by tail-vein injection at the same time-points.

Parasites for Challenge

*P. yoelii* parasites were used for challenge. Sporozoites were obtained by hand dissection of infected mosquito salivary glands. The isolated sporozoites were suspended in HBSS medium containing 1% normal mouse serum. All challenges were accomplished by injecting $5 \times 10^3$ sporozoites in the tail vein.

Immunogenicity Assay

Humoral immune responses to the immunodominant B cell epitope was measured using variants of CSP-specific ELISA assays developed in the laboratory of Dr. Fidel Zavala, Johns Hopkins School of Public Health. CSP-epitope specific INF-γ ELISpots was measured by ELISpots assays (BD Biosciences).

Real-time PCR for liver stage parasites

Real-time PCR was used for the detection and quantification of the liver stages of *Plasmodium yoelii* parasites. Two specific primers, 5'-GGGGATTG-GTTTTGACGTTTTTGCG-3' (SEQ ID NO: 29) (forward primer) and 5'-AAGCATTAAATAAAGCGAATACATCCT-TAT-3' (SEQ ID NO: 30) (reverse primer), were designed to amplify the parasite 18S rRNA sequence. The primers were selected based on the previously published *P. yoelii* (17XNL) 18S rRNA sequence (GeneBank accession number: U44379) using the Primer Express software (PE Applied Biosystems). Amplification with these primers generates a 133 by fragment of the parasite 18S rRNA sequence that contains the maximum number of critical mismatches to the homologous sequence of the mouse 18S rRNA, thereby cross-amplification of the mouse molecules is avoided.

Sporozoite Neutralization Assay

Sporozoite neutralization assay were performed in a total volume of 100 ul that contained $1 \times 10^5$ sporozoites in dissection medium and 10 ul of immune serum from each immunized mouse. The sporozoite mixtures were incubated for 40 min on ice. The sporozoites were then added to HepG1.6 cell cultures that were maintained at 37° C. in 5% $CO_2$. The incubation was carried out for 48 h with changes of culture media every 24 h. All neutralization assays were performed in duplicates. At the end of 48 hours, the cells were harvested. Total RNA was isolated and reverse transcription is performed. 18s rRNA were detected and quantified by real-time PCR.

In Vivo Depletion of T Cell Subsets

To deplete the CD4+, CD8+, or both T cell subsets, immunized mice are injected i.p. with anti-CD4, anti-CD8 or both mAbs. Each mouse received daily doses of 200 µg of anti-CD4 or anti-CD8 or both antibodies for two days. The antibodies were provided by Dr. Fidel Zavala, Johns Hopkins School of Public Health. 24 h after the last immunization, the efficacy of the depletion was estimated by two-color flow cytometry analysis of peripheral blood lymphocytes, using FITC-conjugated anti-CD4 or APC-conjugated anti-CD8 mAbs.

Example 5

Membrane Bound Form of a *P. falciparum* Malaria Vaccine

```
DNA sequence (1504 bp)
                                                (SEQ ID NO: 31)
       CTGCAGTCACCGTCGTCGACAGAGCTGAGATCCTACAGGAGTCCAGGGCTGG

AGAGAAAACCTCTGCGAGGAAAAGGAAGGAGCAAGCCGTGAATTTAAGGGACGCTGTGAAGC

AATCATGGATGCAATGAAGAGAGGGCTCTGCTGTGTGCTGCTGCTGTGTGGAGCAGTCTTCG

TTTCGCCCAGCGGTACCGGATCCGCAGCAAGCAACTTTGACTGCTGTCTTGGATACACAGAC

CGTATTCTTCATCCTAAATTTATTGTGGGCTTCACACGGCAGCTGGCCAATGAAGGCTGTGA

CATCAATGCTATCATCTTTCACACAAAGAAAAAGTTGTCTGTGTGCGCAAATCCAAAACAGA

CTTGGGTGAAATATATTGTGCGTCTCCTCAGTAAAAAAGTCAAGAACATGGAATTCAACGAC

GCTCAGGCGCCGAAGAGTGGATCCATGATGCGCAAGCTGGCCATCCTGTCCGTGTCCTCCTT

CCTGTTCGTGGAGGCCCTGTTCCAGGAGTACCAGTGCTACGGCTCCTCCTCCAACACCCGCG

TGCTGAACGAGCTGAACTACGACAACGCCGGCACCAACCTGTACAACGAGCTGGAGATGAAC

TACTACGGCAAGCAGGAGAACTGGTACTCCCTGAAGAAGAACTCCCGCTCCCTGGGCGAGAA

CGACGACGGCAACAACGAGGACAACGAGAAGCTGCGCAAGCCCAAGCACAAGAAGCTGAAGC

AGCCCGCCGACGGCAACCCCGACCCCAACGCCAACCCCAACGTGGACCCCAACGCCAACCCC

AACGTGGACCCCAACGCCAACCCCAACGTGGACCCCAACGCCAACCCCAACGCCAACCCCAA

CGCCAACCCCAACGCCAACCCCAACGCCAACCCCAACGCCAACCCCAACGCCAACCCCAACG

CCAACCCCAACGCCAACCCCAACGCCAACCCCAACGCCAACCCCAACGCCAACCCCAACGCC

AACCCCAACGCCAACCCCAACGCCAACCCCAACGCCAACCCCAACGCCAACCCCAACGTGGA

CCCCAACGCCAACCCCAACGCCAACCCCAACAAGAACAACCAGGGCAACGGCCAGGGCCACA

ACATGCCCAACGACCCCAACCGCAACGTGGACGAGAACGCCAACGCCAACTCCGCCGTGAAG

AACAACAACAACGAGGAGCCCTCCGACAAGCACATCAAGGAGTACCTGAACAAGATCCAGAA

CTCCCTGTCCACCGAGTGGTCCCCCTGCTCCGTGACCTGCGGCAACGGCATCCAGGTGCGCA

TCAAGCCCGGCTCCGCCAACAAGCCCAAGGACGAGCTGGACTACGCCAACGACATCGAGAAG

AAAATCTGCAAGATGGAGAAGTGCTCCTCCGTGTTCAACGTGGTGAACTCCTCCATCGGCCT

GATCATGGTGCTGTCCTTCCTGTTCCTGAACAGATCCGCAGAAGAACAGAAACTGATCTCAG

AAGAGGATCTGTGATCTAGAAGATCT
```

Single underlined sequence encodes signal sequence for translocation. Double underlined sequence encodes glycosylphatidylinositol (GPI) signal sequence.

Translated protein sequence (457 aa):
(SEQ ID NO: 32)
MDAMKRGLCCVLLLCGAVFVSPSGTGSAASNFDCCLGYTDRILHPKFIVGFT

RQLANEGCDINAIIFHTKKKLSVCANPKQTWVKYIVRLLSKKVKNMEFNDAQAPKSGSMMRK

LAILSVSSFLFVEALFQEYQCYGSSSNTRVLNELNYDNAGTNLYNELEMNYYGKQENWYSLK

KNSRSLGENDDGNNEDNEKLRKPKHKKLKQPADGNPDPNANPNVDPNANPNVDPNANPNVDP

NANPNANPNANPNANPNANPNANPNANPNANPNANPNANPNANPNANPNANPNANPNANPNA

NPNANPNVDPNANPNANPNKNNQGNGQGHNMPNDPNRNVDENANANSAVKNNNNEEPSDKHI

KEYLNKIQNSLSTEWSPCSVTCGNGIQVRIKPGSANKPKDELDYANDIEKKICKMEKCSSVF

NVVNSSIGLIMVLSFLFLNRSAEEQKLISEEDL-

Single underlined sequence is signal sequence for translocation. Double-underlined sequence is glycosylphatidylinositol (GPI) signal sequence.

Example 6

Secreted form of malaria vaccine (GPI deletion)

DNA sequence (1435 bp)
(SEQ ID NO: 33)
CTGCAGTCACCGTCGTCGACAGAGCTGAGATCCTACAGGAGTCCAGGGCTGGAGAGAAAACCTCTGCG

AGGAAAAGGAAGGAGCAAGCCGTGAATTTAAGGGACGCTGTGAAGCAATCATGGATGCAATGAAGAGA

GGGCTCTGCTGTGTGCTGCTGCTGTGTGGAGCAGTCTTCGTTTCGCCCAGCGGTACCGGATCCGCAGC

AAGCAACTTTGACTGCTGTCTTGGATACACAGACCGTATTCTTCATCCTAAATTTATTGTGGGCTTCA

CACGGCAGCTGGCCAATGAAGGCTGTGACATCAATGCTATCATCTTTCACACAAAGAAAAAGTTGTCT

GTGTGCGCAAATCCAAAACAGACTTGGGTGAAATATATTGTGCGTCTCCTCAGTAAAAAAGTCAAGAA

CATGGAATTCAACGACGCTCAGGCGCCGAAGAGTGGATCCATGATGCGCAAGCTGGCCATCCTGTCCG

TGTCCTCCTTCCTGTTCGTGGAGGCCCTGTTCCAGGAGTACCAGTGCTACGGCTCCTCCTCCAACACC

CGCGTGCTGAACGAGCTGAACTACGACAACGCCGGCACCAACCTGTACAACGAGCTGGAGATGAACTA

CTACGGCAAGCAGGAGAACTGGTACTCCCTGAAGAAGAACTCCCGCTCCCTGGGCGAGAACGACGACG

GCAACAACGAGGACAACGAGAAGCTGCGCAAGCCCAAGCACAAGAAGCTGAAGCAGCCCGCCGACGGC

AACCCCGACCCCAACGCCAACCCCAACGTGGACCCCAACGCCAACCCCAACGTGGACCCCAACGCCAA

CCCCAACGTGGACCCCAACGCCAACCCCAACGCCAACCCCAACGCCAACCCCAACGCCAACCCCAACG

CCAACCCCAACGCCAACCCCAACGCCAACCCCAACGCCAACCCCAACGCCAACCCCAACGCCAACCCC

AACGCCAACCCCAACGCCAACCCCAACGCCAACCCCAACGCCAACCCCAACGCCAACCCCAACGCCAA

CCCCAACGCCAACCCCAACGTGGACCCCAACGCCAACCCCAACGCCAACCCCAACAAGAACAACCAGG

GCAACGGCCAGGGCCACAACATGCCCAACGACCCCAACCGCAACGTGGACGAGAACGCCAACGCCAAC

TCCGCCGTGAAGAACAACAACAACGAGGAGCCCTCCGACAAGCACATCAAGGAGTACCTGAACAAGAT

CCAGAACTCCCTGTCCACCGAGTGGTCCCCCTGCTCCGTGACCTGCGGCAACGGCATCCAGGTGCGCA

TCAAGCCCGGCTCCGCCAACAAGCCCAAGGACGAGCTGGACTACGCCAACGACATCGAGAAGAAAATC

TGCAAGATGGAGAAGTGCAGATCCGCAGAAGAACAGAAACTGATCTCAGAAGAGGATCTGTGATCTAG

AAGATCT

Translated protein sequence (434 aa):
(SEQ ID NO: 34)
MDAMKRGLCCVLLLCGAVFVSPSGTGSAASNFDCCLGYTDRILHPKFIVGFTRQLANEGDCI

NAIIFHTKKKLSVCANPKQTWVKYIVRLLSKKVKNMEFNDAQAPKSGSMMRKLAILSVSSFL

-continued

FVEALFQEYQCYGSSSNTRVLNELNYDNAGTNLYNELEMNYYGKQENWYSLKKNSRSLGEND

DGNNEDNEKLRKPKHKKLKQPADGNPDPNANPNVDPNANPNVDPNANPNVDPNANPNANPNA

NPNANPNANPNANPNANPNANPNANPNANPNANPNANPNANPNANPNANPNANPNANPNVDP

NANPNANPNKNNQGNGQGHNMPNDPNRNVDENANANSAVKNNNNEEPSDKHIKEYLNKIQNS

LSTEWSPCSVTCGNGIQVRIKPGSANKPKDELDYANDIEKKICKMEKCRSAEEQKLISEEDL

Example 7

Secreted Form of Malaria Vaccine (Signal Sequence for Translocation and GPI Double Deletion)

```
DNA sequence (1375 bp)
                                                    (SEQ ID NO: 35)
           CTGCAGTCACCGTCGTCGACAGAGCTGAGATCCTACAGGAGTCCAGGGCTGG

AGAGAAAACCTCTGCGAGGAAAAGGAAGGAGCAAGCCGTGAATTTAAGGGACGCTGTGAAGC

AATCATGGATGCAATGAAGAGAGGGCTCTGCTGTGTGCTGCTGCTGTGTGGAGCAGTCTTCG

TTTCGCCCAGCGGTACCGGATCCGCAGCAAGCAACTTTGACTGCTGTCTTGGATACACAGAC

CGTATTCTTCATCCTAAATTTATTGTGGGCTTCACACGGCAGCTGGCCAATGAAGGCTGTGA

CATCAATGCTATCATCTTTCACACAAAGAAAAAGTTGTCTGTGTGCGCAAATCCAAAACAGA

CTTGGGTGAAATATATTGTGCGTCTCCTCAGTAAAAAAGTCAAGAACATGGAATTCAACGAC

GCTCAGGCGCCGAAGAGTGGATCCATGGAGTACCAGTGCTACGGCTCCTCCTCCAACACCCG

CGTGCTGAACGAGCTGAACTACGACAACGCCGGCACCAACCTGTACAACGAGCTGGAGATGA

ACTACTACGGCAAGCAGGAGAACTGGTACTCCCTGAAGAAGAACTCCCGCTCCCTGGGCGAG

AACGACGACGGCAACAACGAGGACAACGAGAAGCTGCGCAAGCCCAAGCACAAGAAGCTGAA

GCAGCCCGCCGACGGCAACCCCGACCCCAACGCCAACCCCAACGTGGACCCCAACGCCAACC

CCAACGTGGACCCCAACGCCAACCCCAACGTGGACCCCAACGCCAACCCCAACGCCAACCCC

AACGCCAACCCCAACGCCAACCCCAACGCCAACCCCAACGCCAACCCCAACGCCAACCCCAA

CGCCAACCCCAACGCCAACCCCAACGCCAACCCCAACGCCAACCCCAACGCCAACCCCAACG

CCAACCCCAACGCCAACCCCAACGCCAACCCCAACGCCAACCCCAACGCCAACCCCAACGTG

GACCCCAACGCCAACCCCAACGCCAACCCCAACAAGAACAACCAGGGCAACGGCCAGGGCCA

CAACATGCCCAACGACCCCAACCGCAACGTGGACGAGAACGCCAACGCCAACTCCGCCGTGA

AGAACAACAACAACGAGGAGCCCTCCGACAAGCACATCAAGGAGTACCTGAACAAGATCCAG

AACTCCCTGTCCACCGAGTGGTCCCCCTGCTCCGTGACCTGCGGCAACGGCATCCAGGTGCG

CATCAAGCCCGGCTCCGCCAACAAGCCCAAGGACGAGCTGGACTACGCCAACGACATCGAGA

AGAAAATCTGCAAGATGGAGAAGTGCAGATCCGCAGAAGAACAGAAACTGATCTCAGAAGAG

GATCTGTGATCTAGAAGATCT

Translated protein sequence (414 aa):
                                                    (SEQ ID NO: 36)
MDAMKRGLCCVLLLCGAVFVSPSGTGSAASNFDCCLGYTDRILHPKFIVGFTRQLANEGDCI

NAIIFHTKKKLSVCANPKQTWVKYIVRLLSKKVKNMEFNDAQAPKSGSMEYQCYGSSSNTRV

LNELNYDNAGTNLYNELEMNYYGKQENWYSLKKNSRSLGENDDGNNEDNEKLRKPKHKKLKQ

PADGNPDPNANPNVDPNANPNVDPNANPNVDPNANPNANPNANPNANPNANPNANPNANPNA

NPNANPNANPNANPNANPNANPNANPNANPNANPNVDPNANPNANPNKNNQGNGQGHN

MPNDPNRNVDENANANSAVKNNNNEEPSDKHIKEYLNKIQNSLSTEWSPCSVTCGNGIQVRI

KPGSANKPKDELDYANDIEKKICKMEMCRSAEEQKLISEEDL-
```

Example 8

Membrane Bound Form of a Malaria Vaccine

DNA sequence (1504 bp)
(SEQ ID NO: 31)

```
CTGCAGTCACCGTCGTCGACAGAGCTGAGATCCTACAGGAGTCCAGGGCTGGAGAGA
AAACCTCTGCGAGGAAAAGGAAGGAGCAAGCCGTGAATTTAAGGGACGCTGTGAAGCAATCA
TGGATGCAATGAAGAGAGGGCTCTGCTGTGTGCTGCTGCTGTGTGGAGCAGTCTTCGTTTCG
CCCAGCGGTACCGGATCCGCAGCAAGCAACTTTGACTGCTGTCTTGGATACACAGACCGTAT
TCTTCATCCTAAATTTATTGTGGGCTTCACACGGCAGCTGGCCAATGAAGGCTGTGACATCA
ATGCTATCATCTTTCACACAAAGAAAAAGTTGTCTGTGTGCGCAAATCCAAAACAGACTTGG
GTGAAATATATTGTGCGTCTCCTCAGTAAAAAAGTCAAGAACATGGAATTCAACGACGCTCA
GGCGCCGAAGAGTGGATCCATGATGCGCAAGCTGGCCATCCTGTCCGTGTCCTCCTTCCTGT
TCGTGGAGGCCCTGTTCCAGGAGTACCAGTGCTACGGCTCCTCCTCCAACACCCGCGTGCTG
AACGAGCTGAACTACGACAACGCCGGCACCAACCTGTACAACGAGCTGGAGATGAACTACTA
CGGCAAGCAGGAGAACTGGTACTCCCTGAAGAAGAACTCCCGCTCCCTGGGCGAGAACGACG
ACGGCAACAACGAGGACAACGAGAAGCTGCGCAAGCCCAAGCACAAGAAGCTGAAGCAGCCC
GCCGACGGCAACCCCGACCCCAACGCCAACCCCAACGTGGACCCCAACGCCAACCCCAACGT
GGACCCCAACGCCAACCCCAACGTGGACCCCAACGCCAACCCCAACGCCAACCCCAACGCCA
ACCCCAACGCCAACCCCAACGCCAACCCCAACGCCAACCCCAACGCCAACCCCAACGCCAAC
CCCAACGCCAACCCCAACGCCAACCCCAACGCCAACCCCAACGCCAACCCCAACGCCAACCC
CAACGCCAACCCCAACGCCAACCCCAACGCCAACCCCAACGCCAACCCCAACGTGGACCCCA
ACGCCAACCCCAACGCCAACCCCAACAAGAACAACCAGGGCAACGGCCAGGGCCACAACATG
CCCAACGACCCCAACCGCAACGTGGACGAGAACGCCAACGCCAACTCCGCCGTGAAGAACAA
CAACAACGAGGAGCCCTCCGACAAGCACATCAAGGAGTACCTGAACAAGATCCAGAACTCCC
TGTCCACCGAGTGGTCCCCCTGCTCCGTGACCTGCGGCAACGGCATCCAGGTGCGCATCAAG
CCCGGCTCCGCCAACAAGCCCAAGGACGAGCTGGACTACGCCAACGACATCGAGAAGAAAAT
CTGCAAGATGGAGAAGTGCTCCTCCGTGTTCAACGTGGTGAACTCCTCCATCGGCCTGATCA
TGGTGCTGTCCTTCCTGTTCCTGAACAGATCCGCAGAAGAACAGAAACTGATCTCAGAAGAG
GATCTGTGATCTAGAAGATCT
```

Translated Protein sequence (457aa):

(SEQ ID NO: 32)

```
MDAMKRGLCCVLLLCGAVFVSPSGTGSAASNFDCCLGYTDRILHPKFIVGFTRQLAN
EGCDINAIIFHTKKKLSVCANPKQTWVKYIVRLLSKKVKNMEFNDAQAPKSGSMMRKLAILS
VSSFLFVEALFQEYQCYGSSSNTRVLNELNYDNAGTNLYNELEMNYYGKQENWYSLKKNSRS
LGENDDGNNEDNEKLRKPKHKKLKQPADGNPDPNANPNVDPNANPNVDPNANPNVDPNANPN
ANPNANPNANPNANPNANPNANPNANPNANPNANPNANPNANPNANPNANPNANPNANPNAN
PNVDPNANPNANPNKNNQGNGQGHNMPNDPNRNVDENANANSAVKNNNNEEPSDKHIKEYLN
KIQNSLSTEWSPCSVTCGNGIQVRIKPGSANKPKDELDYANDIEKKICKMEKCSSVFNVVNS
SIGLIMVLSFLFLNRSAEEQKLISEEDL-
```

The underlined sequence is deleted in the secreted form in Example 10.

Example 9

Secreted Form of a Malaria Vaccine

```
DNA sequence (1435 bp)
                                                      (SEQ ID NO: 33)
     CTGCAGTCACCGTCGTCGACAGAGCTGAGATCCTACAGGAGTCCAGGGCTGGAGAGA

AAACCTCTGCGAGGAAAAGGAAGGAGCAAGCCGTGAATTTAAGGGACGCTGTGAAGCAATCA

TGGATGCAATGAAGAGAGGGCTCTGCTGTGTGCTGCTGCTGTGTGGAGCAGTCTTCGTTTCG

CCCAGCGGTACCGGATCCGCAGCAAGCAACTTTGACTGCTGTCTTGGATACACAGACCGTAT

TCTTCATCCTAAATTTATTGTGGGCTTCACACGGCAGCTGGCCAATGAAGGCTGTGACATCA

ATGCTATCATCTTTCACACAAAGAAAAAGTTGTCTGTGTGCGCAAATCCAAAACAGACTTGG

GTGAAATATATTGTGCGTCTCCTCAGTAAAAAAGTCAAGAACATGGAATTCAACGACGCTCA

GGCGCCGAAGAGTGGATCCATGATGCGCAAGCTGGCCATCCTGTCCGTGTCCTCCTTCCTGT

TCGTGGAGGCCCTGTTCCAGGAGTACCAGTGCTACGGCTCCTCCTCCAACACCCGCGTGCTG

AACGAGCTGAACTACGACAACGCCGGCACCAACCTGTACAACGAGCTGGAGATGAACTACTA

CGGCAAGCAGGAGAACTGGTACTCCCTGAAGAAGAACTCCCGCTCCCTGGGCGAGAACGACG

ACGGCAACAACGAGGACAACGAGAAGCTGCGCAAGCCCAAGCACAAGAAGCTGAAGCAGCCC

GCCGACGGCAACCCCGACCCCAACGCCAACCCCAACGTGGACCCCAACGCCAACCCCAACGT

GGACCCCAACGCCAACCCCAACGTGGACCCCAACGCCAACCCCAACGCCAACCCCAACGCCA

ACCCCAACGCCAACCCCAACGCCAACCCCAACGCCAACCCCAACGCCAACCCCAACGCCAAC

CCCAACGCCAACCCCAACGCCAACCCCAACGCCAACCCCAACGCCAACCCCAACGCCAACCC

CAACGCCAACCCCAACGCCAACCCCAACGCCAACCCCAACGCCAACCCCAACGTGGACCCCA

ACGCCAACCCCAACGCCAACCCCAACAAGAACAACCAGGGCAACGGCCAGGGCCACAACATG

CCCAACGACCCCAACCGCAACGTGGACGAGAACGCCAACGCCAACTCCGCCGTGAAGAACAA

CAACAACGAGGAGCCCTCCGACAAGCACATCAAGGAGTACCTGAACAAGATCCAGAACTCCC

TGTCCACCGAGTGGTCCCCCTGCTCCGTGACCTGCGGCAACGGCATCCAGGTGCGCATCAAG

CCCGGCTCCGCCAACAAGCCCAAGGACGAGCTGGACTACGCCAACGACATCGAGAAGAAAAT

CTGCAAGATGGAGAAGTGCAGATCCGCAGAAGAACAGAAACTGATCTCAGAAGAGGATCTGT

GATCTAGAAGATCT

Translated Protein sequence (434 aa):
                                                      (SEQ ID NO: 34)
     MDAMKRGLCCVLLLCGAVFVSPSGTGSAASNFDCCLGYTDRILHPKFIVGFTRQLAN

EGCDINAIIFHTKKKLSVCANPKQTWVKYIVRLLSKKVKNMEFNDAQAPKSGSMMRKLAILS

VSSFLFVEALFQEYQCYGSSSNTRVLNELNYDNAGTNLYNELEMNYYGKQENWYSLKKNSRS

LGENDDGNNEDNEKLRKPKHKKLKQPADGNPDPNANPNVDPNANPNVDPNANPNVDPNANPN

ANPNANPNANPNANPNANPNANPNANPNANPNANPNANPNANPNANPNANPNANPNANPNAN

PNVDPNANPNANPNKNNQGNGQGHNMPNDPNRNVDENANANSAVKNNNNEEPSDKHIKEYLN

KIQNSLSTEWSPCSVTCGNGIQVRIKPGSANKPKDELDYANDIEKKICKMEKCRSAEEQLKI

SEEDL-
```

Example 10

Figure 11:
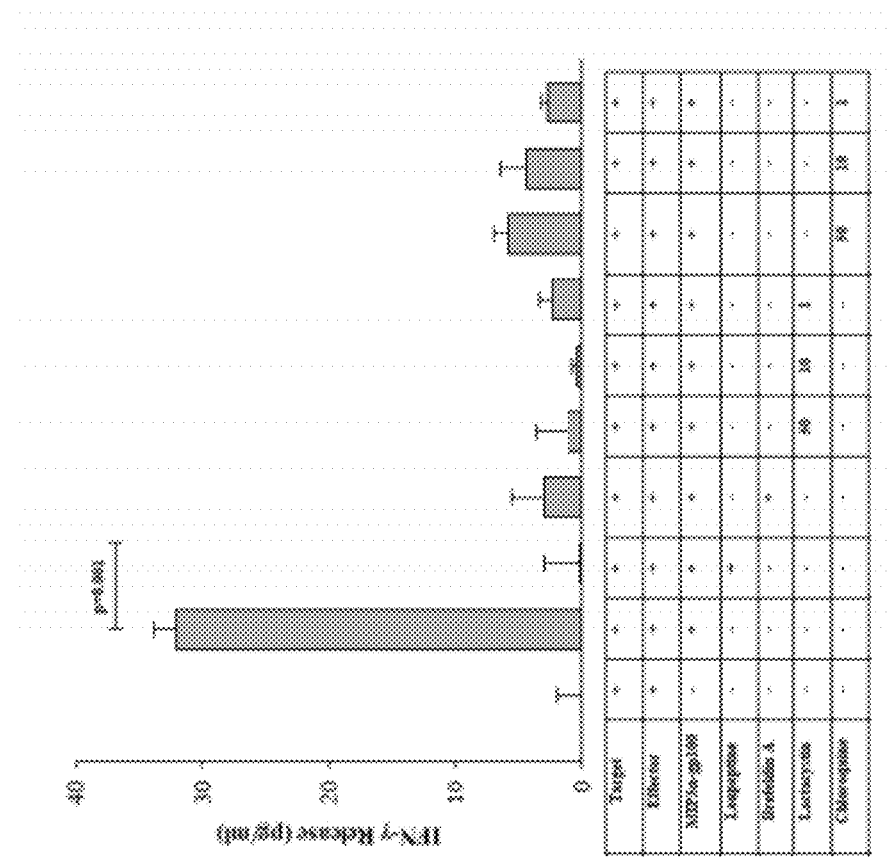
FIG. 11 illustrates the ability of lysosomal and proteosomal inhibitors to block MIP3alpha-gp100-induced IFN-gamma secretion.

Immunization with Chemokine-Fusion Vaccines Enables Cross Presentation of Immunogens Introduction of a melanoma-derived protein antigen (gp100) by fusion to MIP-3α results in cross-presentation via class 1 molecules to CD8 T cells. In one experiment bone marrow derived iDC from naïve C57BL/6 mice were co-incubated with splenocytes from gp100-immune C57BL/6 mice and iDC in the presence of 0.1 mg/ml MIP3α-gp100. After 24 hours IFN-γ concentrations of 425 pg/ml were attained in the culture supernatant fluid. Control DC treated with gp100 alone secreted 100 pg/ml of IFN-γ (background levels). The response was MHC class I dependent; secreted IFN-γ release was reduced significantly to 30 pg/ml. in the presence of specific anti-class I mAb. In a second series of experiments (FIG. 11) it was shown that lactacystin, a specific inhibitor of the proteosomal processing that is required for Class I presentation, could reduce IFN-γ release in response to MIP3α-gp100 in excess of 90%. This effect was not due to toxic effects of lactacystin, since lactacystin treatment did not affect presentation of chemokine fused antigens to CD4 T cells via MHC class II presentation (57). Thus uptake directed to iDC is able to activate both Class I and Class II restricted T cell responses, due to cross presentation of antigen. This allows for development of both the CD8 T-cell-mediated cytotoxic responses that might eliminate infected cells, but also the CD4 T cell-mediated helper responses that would ensure that the cytotoxic responses and any antibody responses that might be generated are optimized.

Example 11

Figure 12:
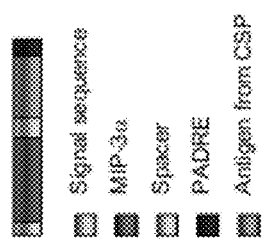
FIG. 12 is a diagrammatic representation of candidate *P. yoelii* vaccine used in preliminary studies.
Figure 13:
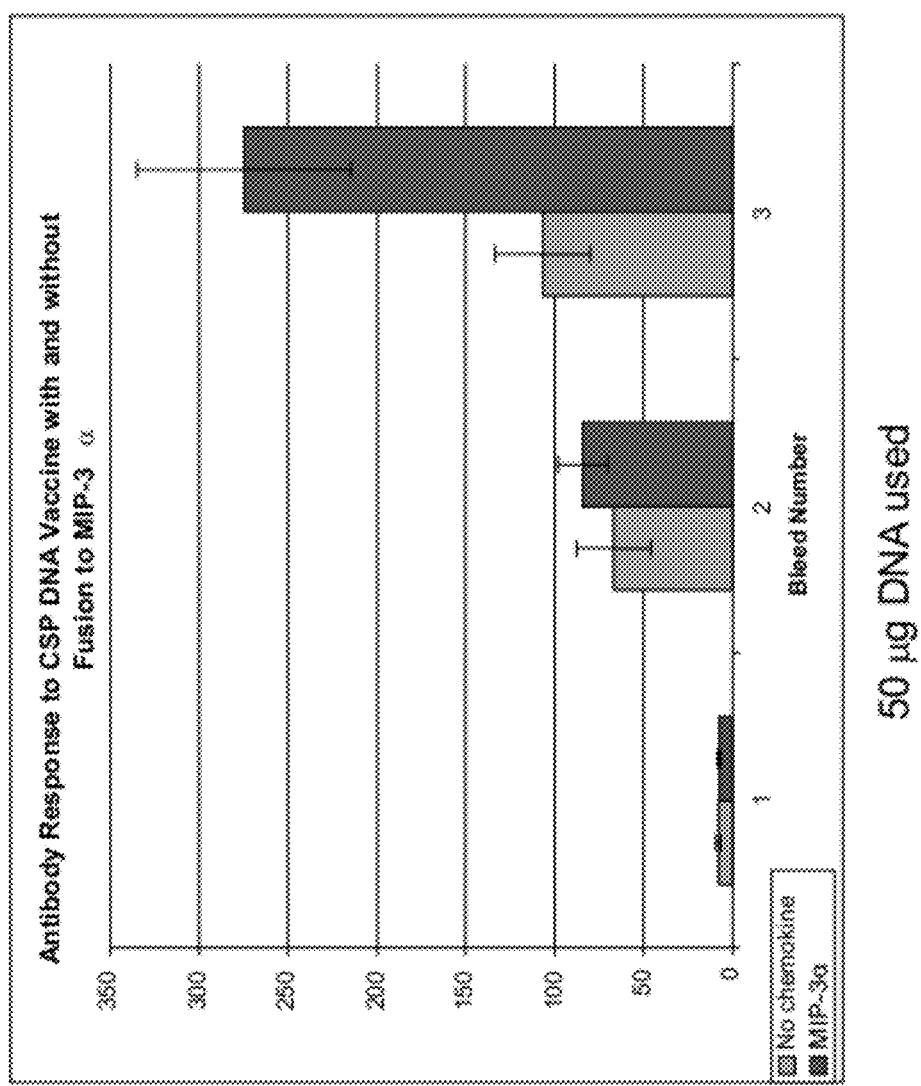
FIG. 13 illustrates results from an experiment in which four BALB/c mice/group were immunized with 50 μg of the DNA vaccine construct described in FIG. 15, with or without DNA encoding the MIP-3α fusion protein included in the construct. Control mice receiving plasmid DNA encoding MIP-3α and an irrelevant immunogen had no detectable antibody (not shown), as was the case for all mice prior to the first immunization. p=0.05 for differences in antibody levels between the constructs shown after the third immunization.
Figure 14:
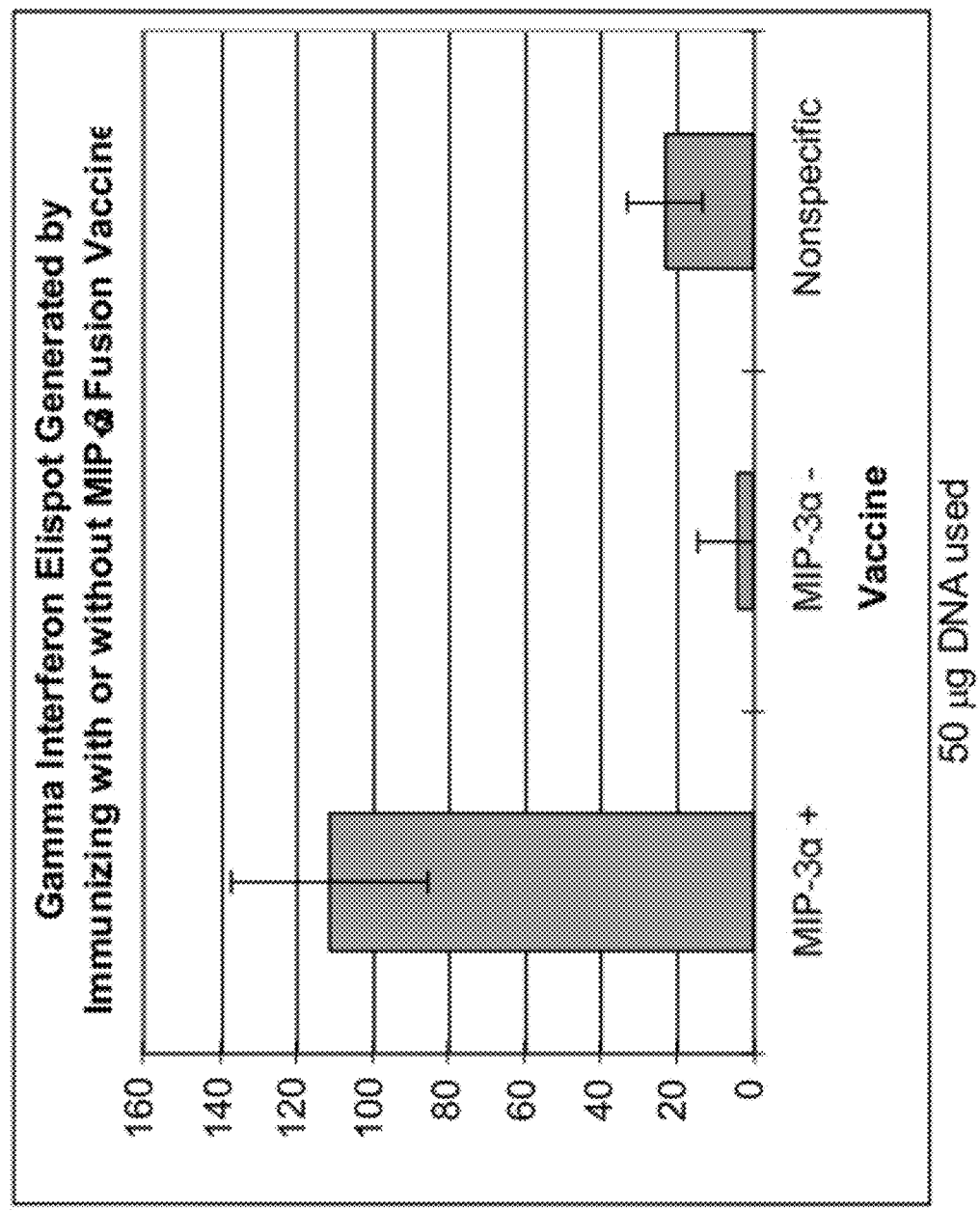
FIG. 14 illustrates Interferon gamma Elispots generated from the spleen of BALB/c mice two weeks after the last of 3 immunizations with 50 μg of the vaccine construct described in FIG. 15. Results represent the mean of Elispots obtained from four mice. p=0.03 for difference between constructs with and without MIP-3alpha.

A MIP-3alpha-encoding DNA fusion vaccine markedly enhances immune responses to P. yoelii CSP antigens over and above the enhanced immunity achieved by in vivo electroporation Pilot studies have been conducted to evaluate the ability of the chemokine-fusion approach to enhance responses to a candidate P. yoelii vaccine in BALB/c mice. A DNA construct (FIG. 12) composed of the SYVPSAEQI (SEQ ID NO: 37) immunodominant P. yoelii Class I-restricted T cell epitope and the (QGPGAP)4 (SEQ ID NO 38) immunodominant P. yoelii B cell epitope were combined with the pan T-cell helper epitope (PADRE) for the class II MHC-restricted epitope of the CSP to maximize responses. The PADRE epitope has been shown to stimulate helper T cells that enhance B and Class I-restricted T cell responses across a wide range of human and mouse class II MHC allotypes. In this initial construct DNA encoding a spacer peptide, (Gly3Ser)3GlySer (SEQ ID NO: 3), was placed between the DNA encoding CSP peptides and that encoding the MIP-3α protein to ensure proper folding of the MIP-3α. Mice received three immunizations of 40 to 50 µg DNA by electroporation at bi-weekly (every two weeks) intervals. Serum was obtained for determination of antibody levels prior to each immunization and two weeks after the last immunization. At the time of the last bleed for serum antibody levels, mice were euthanized and spleen cells were removed for enumeration of interferon gamma secreting cells using standard ELISpot procedures following incubation with the SYVPSAEQI peptide (SEQ ID NO: 37). Results of these studies are shown in FIGS. 13 and 14. A standard t-test was used to evaluate the significance of the observed differences. It is particularly striking that ELISpot responses were 1.5 to 2 orders of magnitude higher in mice receiving the MIP-3α fusion construct compared to those receiving a construct lacking the chemokine gene. It should also be noted that the results are reported as per $10^5$ spleen cells, as opposed to results typically reported as per $10^6$ spleen cells.

Example 12

Figure 15:
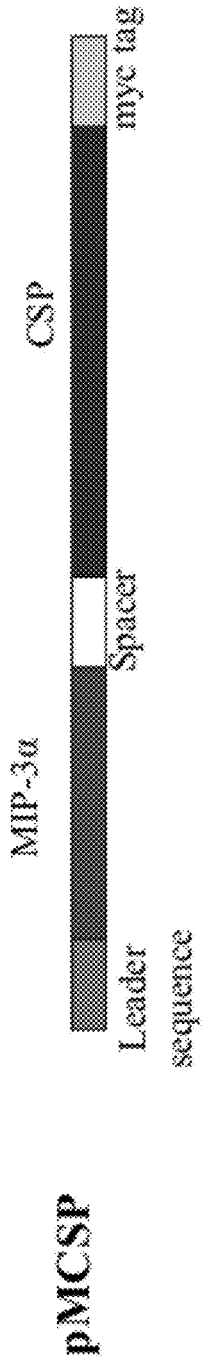
FIG. 15 illustrates a MIP-3α-CSP (*P. yoelli*) fusion DNA vaccine for mouse studies.
Figure 16:
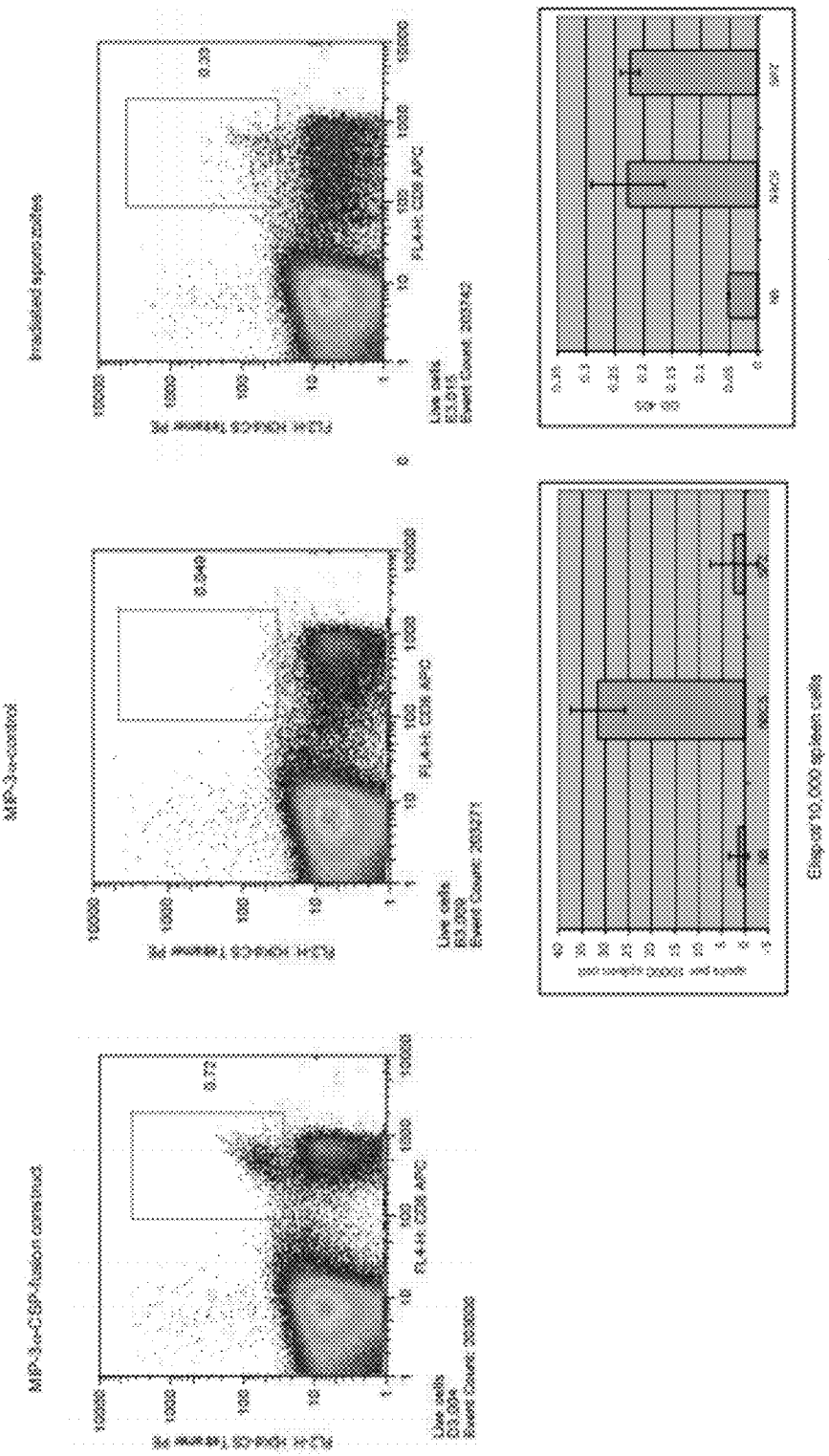
FIG. 16 illustrates comparative antibody concentrations and frequency of tetramer binding and Elispot producing cells from the spleens of mice immunized according to the described regimens. N8=MIP-3a DNA construct without CSP epitopes, N8CS=same construct with CSP epitopes, SPZ=irradiated sporozoites. N8=pM construct in FIG. 1. N8CS=MpMCSP in FIG. 1. Numbers at right side of flow diagrams indicate percentage of cells binding tetramers (represented in inset rectangle).

Comparison of Immune Responses Elicited by MIP-3α-CSP Fusion DNA Vaccine with Irradiated Sporozoites Pilot studies were undertaken comparing the response of the MIP-3α-CSP fusion DNA vaccine (FIG. 15) with irradiated sporozoites. For this study mice were immunized via electroporation with a new vaccine construct in which PADRE used in the previous construct was replaced by the YNRNIVNRLLGDALNGKPEEK (SEQ ID NO: 39) Class II MHC T cell epitope derived from the CSP protein. The responses to this vaccine and a control DNA construct lacking the CSP epitopes (40 to 50 µg DNA administered by electroporation followed by two boosts at 4 week intervals) were compared to the response to 50,000 irradiated P. yoelii sporozoites followed by two boosts of 25,000 irradiated sporozoites at 4 week intervals. Two weeks after the final immunization mice were bled for antibody concentrations and euthanized to obtain spleen cells to determine Elispot responses and the frequency of T cells binding a tetramer consisting of the mouse H-2K$^b$ antigen and the SYVPSAEQI (SEQ ID NO: 37) Class I restricted epitope included in the vaccine. Tetramers were provided by Dr. Zavala and prepared as previously described (Hafalla J.C. et al. J. Immunol. Vol. 171, pp. 964-970 (2003)). Responses to the different vaccines are shown in FIG. 16. For a control immunized mouse, 0.05% of CD8-bearing T cells bound the tetramer, compared to 0.72% of T cells from a mouse immunized with the MIP-3α-CSP fusion construct and 0.33% of T cells from a mouse immunized with the irradiated sporozoites. Antibody responses were equivalent between recipients of the sporozoite vaccine vs. the fusion vaccine, while Elispot responses to the Class I restricted epitope were an order of magnitude higher in the recipients of the fusion vaccine compared to that in recipients of the sporozoite vaccine.

Example 13

Figure 17:
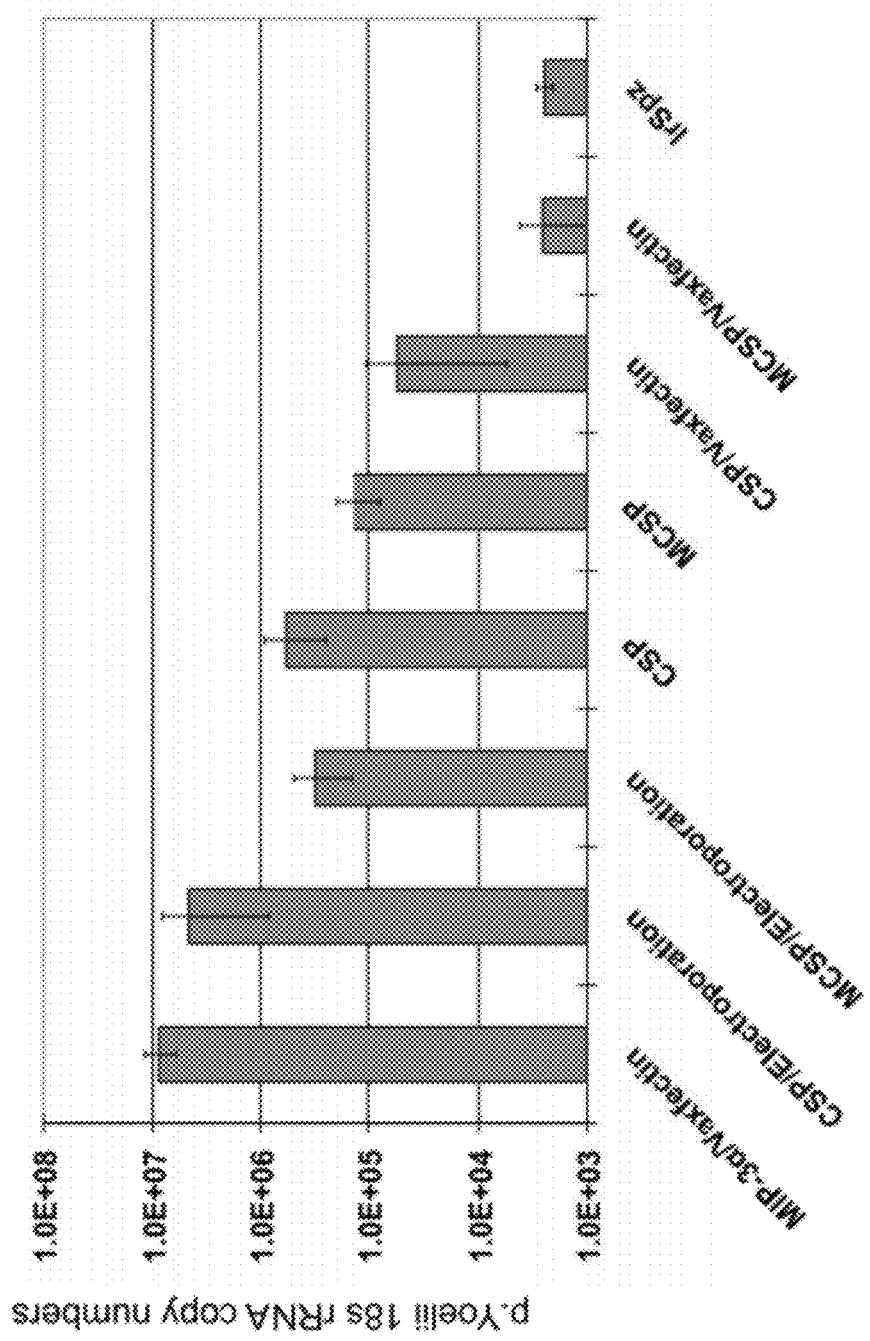
FIG. 17 illustrates liver stage parasites recovered from C57Bl/6 mice immunized with 2 μg of different DNA constructs and challenged with 5000 sporozoites.
Figure 18:
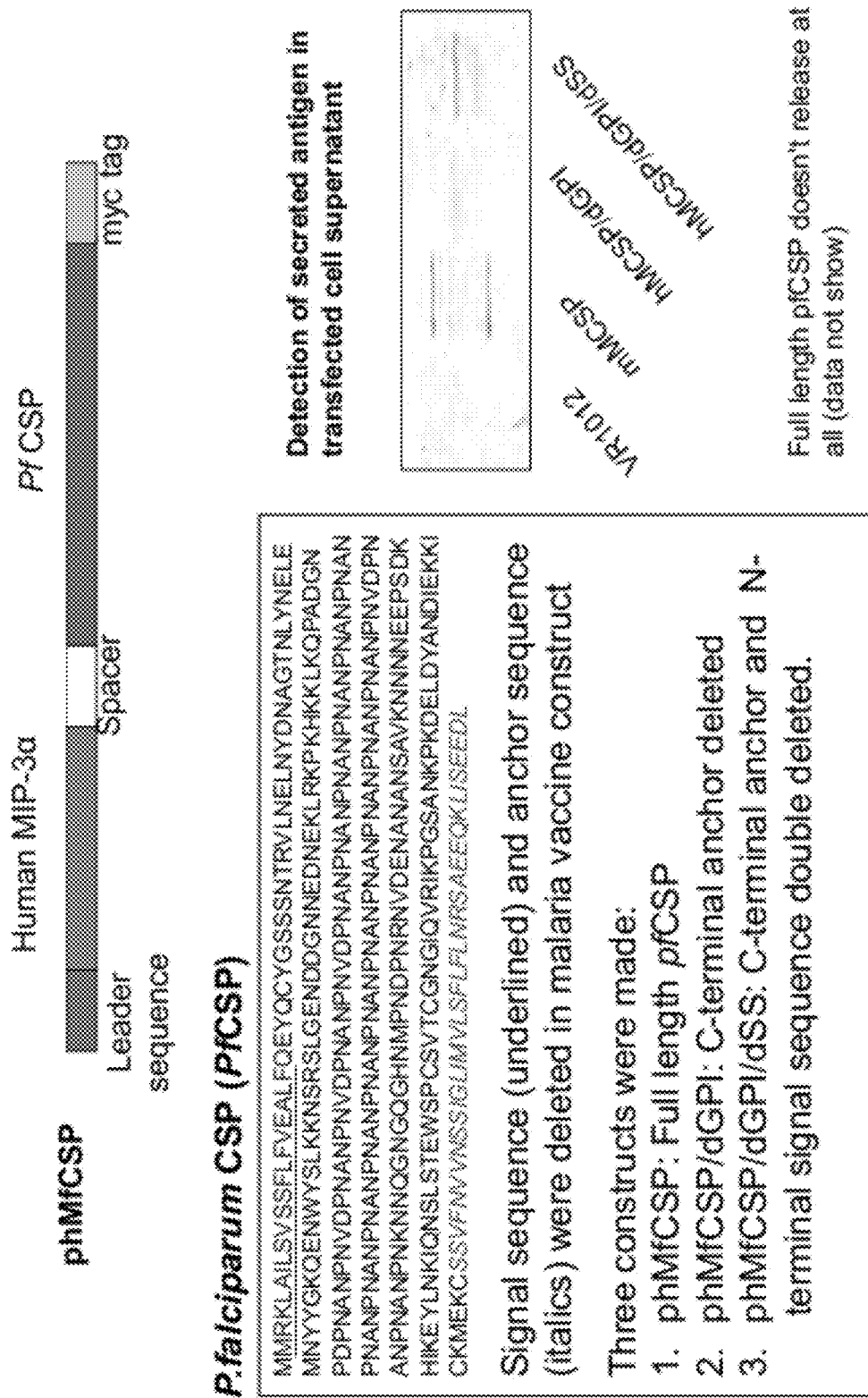
FIG. 18 illustrates a diagrammatic representation of sequences inserted into plasmid VR1012.

A DNA vaccine was prepared using DNA encoding CSP of Plasmodium yoelli (P. yoelli) fused to DNA encoding murine MIP-3α separated by DNA encoding a linker peptide (EFNDAQAPKS (SEQ ID NO: 40)). Both Balb/c mice, which are known to develop both humoral and CD8+ T-cell response to CSP, and C57Bl/6 mice, for which CD8+ T-cell responses to CSP have not been demonstrated, were immunized on three occasions with this DNA construct in combination with Vaxfectin adjuvant, along with various controls, including, but not limited to, the "gold standard" control of irradiated sporozoites, as well as the DNA construct administered by electroporation to improve in vivo transfection of the DNA into host cells. Two to three weeks after the final immunization all of the mice were challenged intravenously with 5000 live sporozoites and 48 hours later the mice were euthanized and the presence of P. yoelii ribosomal RNA in the mouse liver was quantitated using reverse transcribed quantitative polymerase chain reaction. As is evident from the FIG. 17, the MIP-3 alpha +Vaxfectin provided the best protection among the DNA vaccines. In the case of C57Bl/6 mice, the parasite load was reduced by four orders of magnitude and was equivalent to that observed with irradiated sporozoites. For the Balb/c mice the parasite load was only reduced by a single order of magnitude with the MIP-3 alpha CSP-Vaxfectin immunization, but these mice can be more susceptible to infection, as evidenced by the higher parasite load in the livers of control mice. Natural infection transmitted by mosquito can result in exposure of the host to between 1 and 1000 malaria sporozoites, considerably below the challenge levels used in the current studies.

Example 14

Figure 19:
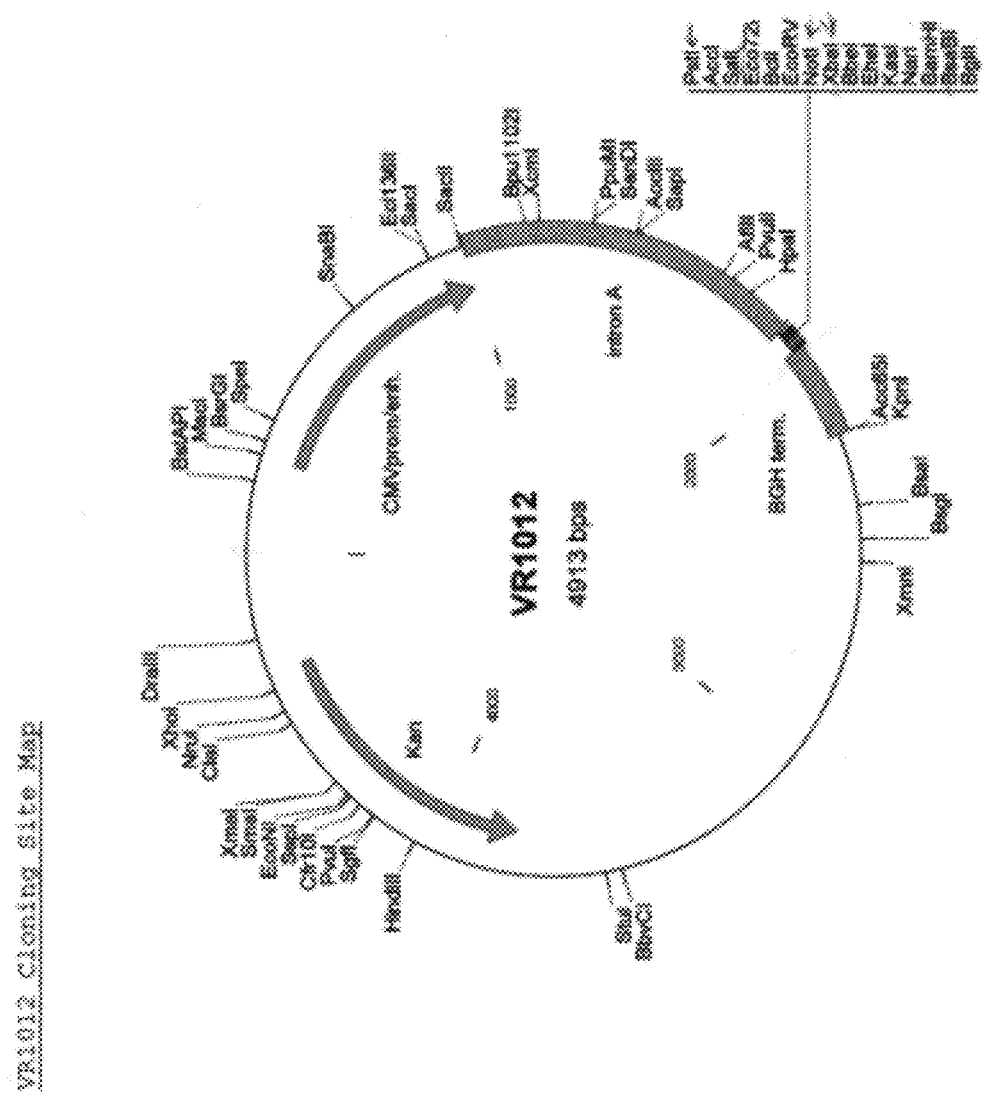
FIG. 19 illustrates VR1012 cloning site map.

Vector VR1012 (4913 bp; Map in FIG. 19)

(SEQ ID NO: 41)
TCGCGCGTTTCGGTGATGACGGTGAAAACCTCTGACACATGCAGCTCCCGGAGACGGTCACA

GCTTGTCTGTAAGCGGATGCCGGGAGCAGACAAGCCCGTCAGGGCGCGTCAGCGGGTGTTGGCGGGTG

TCGGGGCTGGCTTAACTATGCGGCATCAGAGCAGATTGTACTGAGAGTGCACCATATGCGGTGTGAAA

TACCGCACAGATGCGTAAGGAGAAAATACCGCATCAGATTGGCTATTGGCCATTGCATACGTTGTATC

CATATCATAATATGTACATTTATATTGGCTCATGTCCAACATTACCGCCATGTTGACATTGATTATTG

ACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACGGTAA

ACTGCCCACTTGGCAGTACATCAAGTGTATCATATGCCAAGTACGCCCCCTATTGACGTCAATGACGG

TAAATGGCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGATAGCGG

TTTGACTCACGGGGATTTCCAAGTCTCCACCCCATTGACGTCAATGGGAGTTTGTTTTGGCACCAAAA

TCAACGGGACTTTCCAAAATGTCGTAACAACTCCGCCCCATTGACGCAAATGGGCGGTAGGCGTGTAC

GGTGGGAGGTCTATATAAGCAGAGCTCGTTTAGTGAACCGTCAGATCGCCTGGAGACGCCATCCACGC

TGTTTTGACCTCCATAGAAGACACCGGGACCGATCCAGCCTCCGCGGCCGGGAACGGTGCATTGGAAC

GCGGATTCCCCGTGCCAAGAGTGACGTAAGTACCGCCTATAGACTCTATAGGCACACCCCTTTGGCTC

TTATGCATGCTATACTGTTTTTGGCTTGGGGCCTATACACCCCCGCTTCCTTATGCTATAGGTGATGG

TATAGCTTAGCCTATAGGTGTGGGTTATTGACCATTATTGACCACTCCCCTATTGGTGACGATACTTT

CCATTACTAATCCATAACATGGCTCTTTGCCACAACTATCTCTATTGGCTATATGCCAATACTCTGTC

CTTCAGAGACTGACACGGACTCTGTATTTTTACAGGATGGGGTCCCATTTATTATTTACAAATTCACA

TATACAACAACGCCGTCCCCCGTGCCCGCAGTTTTTATTAAACATAGCGTGGGATCTCCACGCGAATC

TCGGGTACGTGTTCCGGACATGGGCTCTTCTCCGGTAGCGGCGGAGCTTCCACATCCGAGCCCTGGTC

CCATGCCTCCAGCGGCTCATGGTCGCTCGGCAGCTCCTTGCTCCTAACAGTGGAGGCCAGACTTAGGC

ACAGCACAATGCCCACCACCACCAGTGTGCCGCACAAGGCCGTGGCGGTAGGGTATGTGTCTGAAAAT

GAGCGTGGAGATTGGGCTCGCACGGCTGACGCAGATGGAAGACTTAAGGCAGCGGCAGAAGAAGATGC

AGGCAGCTGAGTTGTTGTATTCTGATAAGAGTCAGAGGTAACTCCCGTTGCGGTGCTGTTAACGGTGG

AGGGCAGTGTAGTCTGAGCAGTACTCGTTGCTGCCGCGCGCGCCACCAGACATAATAGCTGACAGACT

AACAGACTGTTCCTTTCCATGGGTCTTTTCTGCAGTCACCGTCGTCGACACGTGTGATCAGATATCGC

GGCCGCTCTAGACCAGGCGCCTGGATCCAGATCTGCTGTGCCTTCTAGTTGCCAGCCATCTGTTGTTT

GCCCCTCCCCCGTGCCTTCCTTGACCCTGGAAGGTGCCACTCCCACTGTCCTTTCCTAATAAAATGAG

GAAATTGCATCGCATTGTCTGAGTAGGTGTCATTCTATTCTGGGGGGTGGGGTGGGCAGGACAGCAA

GGGGGAGGATTGGGAAGACAATAGCAGGCATGCTGGGGATGCGGTGGGCTCTATGGGTACCCAGGTGC

TGAAGAATTGACCCGGTTCCTCCTGGGCCAGAAAGAAGCAGGCACATCCCCTTCTCTGTGACACACCC

TGTCCACGCCCCTGGTTCTTAGTTCCAGCCCCACTCATAGGACACTCATAGCTCAGGAGGGCTCCGCC

-continued

```
TTCAATCCCACCCGCTAAAGTACTTGGAGCGGTCTCTCCCTCCCTCATCAGCCCACCAAACCAAACCT
AGCCTCCAAGAGTGGGAAGAAATTAAAGCAAGATAGGCTATTAAGTGCAGAGGGAGAGAAAATGCCTC
CAACATGTGAGGAAGTAATGAGAGAAATCATAGAATTTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAA
TCAGGGGATAACGCAGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGCGC
TCTCCTGTTCCGACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGAACAGTATTTGGTATCTGCG
CTCTGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGATCC
TTTGATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTAAAGT
ATATATGAGTAAACTTGGTCTGACAGTTACCAATGCTTAATCAGTGAGGCACCTATCTCAGCGATCTG
TCTATTTCGTTCATCCATAGTTGCCTGACTCCGGGGGGGGGGGCGCTGAGGTCTGCCTCGTGAAGAA
GGTGTTGCTGACTCATACCAGGCCTGAATCGCCCCATCATCCAGCCAGAAAGTGAGGGAGCCACGGTT
GATGAGAGCTTTGTTGTAGGTGGACCAGTTGGTGATTTTGAACTTTTGCTTTGCCACGGAACGGTCTG
CGTTGTCGGGAAGATGCGTGATCTGATCCTTCAACTCAGCAAAAGTTCGATTTATTCAACAAAGCCGC
CGTCCCGTCAAGTCAGCGTAATGCTCTGCCAGTGTTACAACCAATTAACCAATTCTGATTAGAAAAAC
TCATCGAGCATCAAATGAAACTGCAATTTATTCATATCAGGATTATCAATACCATATTTTGAAAAAG
CCGTTTCTGTAATGAAGGAGAAAACTCACCGAGGCAGTTCCATAGGATGGCAAGATCCTGGTATCGGT
CTGCGATTCCGACTCGTCCAACATCAATACAACCTATTAATTTCCCCTCGTCAAAAATAAGGTTATCA
AGTGAGAAATCACCATGAGTGACGACTGAATCCGGTGAGAATGGCAAAAGCTTATGCATTTCTTTCCA
GACTTGTTCAACAGGCCAGCCATTACGCTCGTCATCAAAATCACTCGCATCAACCAAACCGTTATTCA
TTCGTGATTGCGCCTGAGCGAGACGAAATACGCGATCGCTGTTAAAAGGACAATTACAAACAGGAATC
GAATGCAACCGGCGCAGGAACACTGCCAGCGCATCAACAATATTTTCACCTGAATCAGGATATTCTTC
TAATACCTGGAATGCTGTTTTCCCGGGGATCGCAGTGGTGAGTAACCATGCATCATCAGGAGTACGGA
TAAAATGCTTGATGGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGGGCTTCCCATACAA
TCGATAGATTGTCGCACCTGATTGCCCGACATTATCGCGAGCCCATTTATACCCATATAAATCAGCAT
CCATGTTGGAATTTAATCGCGGCCTCGAGCAAGACGTTTCCCGTTGAATATGGCTCATAACACCCCTT
GTATTACTGTTTATGTAAGCAGACAGTTTTATTGTTCATGATGATATATTTTTATCTTGTGCAATGTA
ACATCAGAGATTTTGAGACACAACGTGGCTTTCCCCCCCCCCCCATTATTGAAGCATTTATCAGGGTT
ATTGTCTCATGAGCGGATACATATTTGAATGTATTTAGAAAAATAAACAAATAGGGGTTCCGCGCACA
TTTCCCCGAAAAGTGCCACCTGACGTCTAAGAAACCATTATTATCATGACATTAACCTATAAAAATAG
GCGTATCACGAGGCCCTTTCGTC
```

Example 15

Partial Sequence of hTPA and its Leader Sequence (Underlined) Included in Construct (Restriction Sites PstI, KpnI, and BamHI (Bold))

```
                                                    (SEQ ID NO: 42)
CTGCAGTCACCGTCGTCGACAGAGCTGAGATCCTACAGGAGTCCAGGGCTGGAGAGAAA

ACCTCTGCGAGGAAAAGGAAGGAGCAAGCCGTGAATTTAAGGGACGCTGTGAAGCAATCATGGA

TGCAATGAAGAGAGGGCTCTGCTGTGTGCTGCTGCTGTGTGGAGCAGTCTTCGTTTCGCCCAGC

GGTACCGGATCC

Translated protein of hPTA:
                                                    (SEQ ID NO: 43)
MDAMKRGLCCVLLLCGAVFVSPS
```

Example 16

Human MIP-3alpha DNA

```
                                                    (SEQ ID NO: 44)
GCAGCAAGCAACTTTGACTGCTGTCTTGGATACACAGACCGTATTCTTCATCCTA

AATTTATTGTGGGCTTCACACGGCAGCTGGCCAATGAAGGCTGTGACATCAATGCTATCA

TCTTTCACACAAAGAAAAAGTTGTCTGTGTGCGCAAATCCAAAACAGACTTGGGTGAAAT

ATATTGTGCGTCTCCTCAGTAAAAAAGTCAAGAACATG

Translated protein of MIP-3 alpha:
                                                    (SEQ ID NO: 45)
AASNFDCCLGYTDRILHPKFIVGFTRQLANEGCDINAIIFHTKKKLSVCANPKQTWVKYI

VRLLSKKVKNM
```

Example 17

Spacer Between hMIP-3a and pfCSP with BamHI Restriction site (Underlined)

```
                                                    (SEQ ID NO: 46)
GAATTCAACGACGCTCAGGCGCCGAAGAGTGGATCC
```

Translated protein of spacer:
(SEQ ID NO: 1)
EFNDAQAPKSGS

Example 18

Codon Optimized PfCSP (33 aa (22 NANP repeats (SEQ ID NO: 47)))

```
                                                    (SEQ ID NO: 48)
ATGATGCGCAAGCTGGCCATCCTGTCCGTGTCCTCCTTCCTGTTCGTGGAGGCCCT

GTTCCAGGAGTACCAGTGCTACGGCTCCTCCTCCAACACCCGCGTGCTGAACGAGCTGA

ACTACGACAACGCCGGCACCAACCTGTACAACGAGCTGGAGATGAACTACTACGGCAAG

CAGGAGAACTGGTACTCCCTGAAGAAGAACTCCCGCTCCCTGGGCGAGAACGACGACGG

CAACAACGAGGACAACGAGAAGCTGCGCAAGCCCAAGCACAAGAAGCTGAAGCAGCCC

GCCGACGGCAACCCCGACCCCAACGCCAACCCCAACGTGGACCCCAACGCCAACCCCAA

CGTGGACCCCAACGCCAACCCCAACGTGGACCCCAACGCCAACCCCAACGCCAACCCCA

ACGCCAACCCCAACGCCAACCCCAACGCCAACCCCAACGCCAACCCCAACGCCAACCCC

AACGCCAACCCCAACGCCAACCCCAACGCCAACCCCAACGCCAACCCCAACGCCAACCC

CAACGCCAACCCCAACGCCAACCCCAACGCCAACCCCAACGCCAACCCCAACGCCAACC

CCAACGTGGACCCCAACGCCAACCCCAACGCCAACCCCAACAAGAACAACCAGGGCAA

CGGCCAGGGCCACAACATGCCCAACGACCCCAACCGCAACGTGGACGAGAACGCCAAC
```

```
                              -continued
GCCAACTCCGCCGTGAAGAACAACAACAACGAGGAGCCCTCCGACAAGCACATCAAGG

AGTACCTGAACAAGATCCAGAACTCCCTGTCCACCGAGTGGTCCCCCTGCTCCGTGACCT

GCGGCAACGGCATCCAGGTGCGCATCAAGCCCGGCTCCGCCAACAAGCCCAAGGACGA

GCTGGACTACGCCAACGACATCGAGAAGAAAATCTGCAAGATGGAGAAGTGCTCCTCCG

TGTTCAACGTGGTGAACTCCTCCATCGGCCTGATCATGGTGCTGTCCTTCCTGTTCCTGAAC

Translated protein of codon-optimized PfCSP
                                                     (SEQ ID NO: 49)
    MMRKLAILSVSSFLFVEALFQEYQCYGSSSNTRVLNELNYDNAGTNLYNELEMNYY

GKQENWYSLKKNSRSLGENDDGNNEDNEKLRKPKHKKLKQPADGNPDPNANPNVDPNANP

NVDPNANPNVDPNANPNANPNANPNANPNANPNANPNANPNANPNANPNANPNANPNANP

NANPNANPNANPNANPNANPNVDPNANPNANPNKNNQGNGQGHNMPNDPNRNVDENAN

ANSAVKNNNNEEPSDKHIKEYLNKIQNSLSTEWSPCSVTCGNGIQVRIKPGSANKPKDEL

DYANDIEKKICKMEKCSSVFNVVNSSIGLIMVLSFLFLN
```

Example 19 c-Myc Tag with Spacer (in Single Underline), Stop Codon (in Box), and Restriction Enzyme Sites XbaI BgIII (Double Underline)

```
                                                     (SEQ ID NO: 50)
AGATCCGCAGAAGAACAGAAACTGATCTCAGAAGAGGATCTGTGATCTAG

AAGATCT

Translated protein of c-myc tag:
                                                     (SEQ ID NO: 51)
RSAEEQKLISEEDL
```

Example 20

FIG. 20 illustrates a sequence of a synthesized *Plasmodium falciparum* vaccine construct. FIG. 21 illustrates hTPA-hMIP3a-pfCSP-myc DNA sequence.

Example 21

A human subject will be administered a pharmaceutical composition comprising a plasmid comprising a nucleic acid sequence from FIG. 21 (hTPA-hMIP3a-pfCSP-myc). The pharmaceutical composition will also comprise a liposome that comprises a commixture of (±)-N-(3-aminopropyl)-N,N-dimethyl-2,3-bis(cis-9-tetradecenyloxy)-1-propanaminium bromide (GAP-DMORIE) and 1,2-diphytanoyl-sn-glycero-3-phosphoethanolamine (DPyPE). The human subject will be administered the pharmaceutical composition by intraperitoneal injection, subcutaneous injection, or intramuscular injection two times over a 6 month period. The human subject will develop an immune response to the circumsporozoite protein that will help protect the subject from developing malaria.

Example 22

An human subject will be administered a pharmaceutical composition comprising a plasmid comprising nucleic acid sequence that encodes a breast cancer antigen fused to MIP-3α, and an adjuvant that comprises a commixture of (±)-N-(3-aminopropyl)-N,N-dimethyl-2,3-bis(cis-9-tetradecenyloxy)-1-propanaminium bromide (GAP-DMORIE) and 1,2-diphytanoyl-sn-glycero-3-phosphoethanolamine (DPyPE). The human subject will be administered the pharmaceutical composition by intraperitoneal injection, subcutaneous injection, or intramuscular injection two times over a 6 month period. The subject will develop an immune response to the breast cancer antigen that will help protect the subject from developing breast cancer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 56

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 1

Glu Phe Asn Asp Ala Gln Ala Pro Lys Ser Gly Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Ser Gly Gly Gly Ser Gly Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser Gly Gly Gly Ser Gly Gly Gly Ser Gly Ser
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Ser Gly Gly Gly Ser Gly Gly Gly Ser Gly Gly Gly Ser
1               5                   10                  15

Gly Ser

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Ser Gly Gly Gly Ser Gly Gly Gly Ser Gly Gly Gly Ser
1               5                   10                  15

Gly Gly Gly Ser Gly Ser
            20

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Ser Gly Gly Gly Ser Gly Gly Gly Ser Gly Gly Gly Ser
1               5                   10                  15

-continued

```
Gly Gly Gly Ser Gly Gly Gly Ser Gly Ser
            20              25
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Pro Gly Pro Gly
1               5
```

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

```
His His His His His His
1               5
```

<210> SEQ ID NO 9
<211> LENGTH: 336
<212> TYPE: DNA
<213> ORGANISM: Homo sapiens

<400> SEQUENCE: 9

```
agactcagct cctggtgaag ctcccagcca tcagccatga gggtcttgta tctcctcttc    60
tcgttcctct tcatattcct gatgcctctt ccaggtgttt ttggtggtat aggcgatcct   120
gttacctgcc ttaagagtgg agccatatgt catccagtct tttgccctag aaggtataaa   180
caaattggca cctgtggtct ccctggaaca aaatgctgca aaaagccatg aggaggccaa   240
gaagctgctg tggctgatgc ggattcagaa agggctccct catcagagac gtgcgacatg   300
taaaccaaat taaactatgg tgtccaaaga tacgca                             336
```

<210> SEQ ID NO 10
<211> LENGTH: 64
<212> TYPE: PRT
<213> ORGANISM: Homo sapiens

<400> SEQUENCE: 10

```
Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 11
<211> LENGTH: 437
<212> TYPE: DNA
<213> ORGANISM: Homo sapiens

<400> SEQUENCE: 11

```
caaatccata gggagctctg ccttaccatt gggttcctaa ttaactgagt gagtgggtgt      60
gttctgcatg gtgagaggca ttggaatgat gcatcagaaa acatgtcata atgtcatcac    120
tgtaatatga caagaattgc agctgtggct ggaacctttta taaagtgacc aagcacacct   180
tttcatccag tctcagcgtg gggtgaagcc tagcagctat gaggatccat tatcttctgt   240
ttgctttgct cttcctgttt ttggtgcctg ttccaggtca tggaggaatc ataaacacat   300
tacagaaata ttattgcaga gtcagaggcg gccggtgtgc tgtgctcagc tgccttccaa   360
aggaggaaca gatcggcaag tgctcgacgc gtggccgaaa atgctgccga agaaagaaat   420
aaaaaccctg aaacatg                                                  437

<210> SEQ ID NO 12
<211> LENGTH: 67
<212> TYPE: PRT
<213> ORGANISM: Homo sapiens

<400> SEQUENCE: 12

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 13
<211> LENGTH: 851
<212> TYPE: DNA
<213> ORGANISM: Homo sapiens

<400> SEQUENCE: 13
agaatataac agcactccca aagaactggg tactcaacac tgagcagatc tgttctttga    60
gctaaaaacc atgtgctgta ccaagagttt gctcctggct gctttgatgt cagtgctgct   120
actccacctc tgcggcgaat cagaagcagc aagcaacttt gactgctgtc ttggatacac   180
agaccgtatt cttcatccta aatttattgt gggcttcaca cggcagctgg ccaatgaagg   240
ctgtgacatc aatgctatca tctttcacac aaagaaaaag ttgtctgtgt gcgcaaatcc   300
aaaacagact tgggtgaaat atattgtgcg tctcctcagt aaaaaagtca agaacatgta   360
aaaactgtgg ctttttctgga atggaattgg acatagccca agaacagaaa gaaccttgct   420
ggggttggag gtttcacttg cacatcatgg agggtttagt gcttatctaa tttgtgcctc   480
actggacttg tccaattaat gaagttgatt catattgcat catagtttgc tttgtttaag   540
catcacatta aagttaaact gtattttatg ttatttatag ctgtaggttt tctgtgttta   600
gctatttaat actaattttc cataagctat tttggtttag tgcaaagtat aaaattatat   660 ttgggggga ataagattat atggactttc ttgcaagcaa caagctattt tttaaaaaaa   720
actatttaac attcttttgt ttatattgtt ttgtctccta aattgttgta attgcattat   780 aaataagaa aaatattaat aagacaaata ttgaaaataa agaaacaaaa agttcttctg   840
ttaaaaaaaa a                                                       851

<210> SEQ ID NO 14
<211> LENGTH: 96
```

<212> TYPE: PRT
<213> ORGANISM: Homo sapiens

<400> SEQUENCE: 14

Met Cys Cys Thr Lys Ser Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
        50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 15
<211> LENGTH: 848
<212> TYPE: DNA
<213> ORGANISM: Homo sapiens

<400> SEQUENCE: 15
agaatataac agcactccca aagaactggg tactcaacac tgagcagatc tgttctttga      60
gctaaaaacc atgtgctgta ccaagagttt gctcctggct gctttgatgt cagtgctgct    120
actccacctc tgcggcgaat cagaagcaag caactttgac tgctgtcttg gatacacaga    180
ccgtattctt catcctaaat ttattgtggg cttcacacgg cagctggcca atgaaggctg    240
tgacatcaat gctatcatct ttcacacaaa gaaaaagttg tctgtgtgcg caaatccaaa    300
acagacttgg gtgaaatata ttgtgcgtct cctcagtaaa aaagtcaaga acatgtaaaa    360
actgtggctt ttctggaatg gaattggaca tagcccaaga acagaaagaa ccttgctggg    420
gttggaggtt tcacttgcac atcatggagg gtttagtgct tatctaattt gtgcctcact    480
ggacttgtcc aattaatgaa gttgattcat attgcatcat agtttgcttt gtttaagcat    540
cacattaaag ttaaactgta ttttatgtta tttatagctg taggttttct gtgtttagct    600
atttaatact aattttccat aagctatttt ggtttagtgc aaagtataaa attatatttg    660
ggggggaata agattatatg gactttcttg caagcaacaa gctattttt aaaaaaaact    720
atttaacatt ctttttgttta tattgttttg tctcctaaat tgttgtaatt gcattataaa    780
ataagaaaaa tattaataag acaaatattg aaaataagaa aacaaaaagt tcttctgtta    840
aaaaaaaa                                                              848

<210> SEQ ID NO 16
<211> LENGTH: 852
<212> TYPE: DNA
<213> ORGANISM: Mus musculus

<400> SEQUENCE: 16
gagcactcgc agggcactgg gtacccagca ctgagtacat caactcctgg agctgagaat      60
ggcctgcggt ggcaagcgtc tgctcttcct tgctttggca tgggtactgc tggctcacct    120
ctgcagccag gcagaagcag caagcaacta cgactgttgc ctctcgtaca tacagacgcc    180
tcttccttcc agagctattg tgggtttcac aagacagatg gccgatgaag cttgtgacat    240
taatgctatc atctttcaca cgaagaaaag aaaatctgtg tgcgctgatc aaagcagaa    300
ctgggtgaaa agggctgtga acctcctcag cctaagagtc aagaagatgt aaaaaactga    360

```
tgctttttg ggatggaatt ggacacagcc caaggaggaa atgatcacag ctggggttga    420
aggcttcacc tgcacatcac tgcacagacc tgatttgtgt cccagtggac ttgtccaatg    480
gatgaagttg attcatattg catcatagtg tgtcatattt aagctcacat tagagttaag    540
ttgtatttta tgttatttat agatctgaat tttctatgtt tagctattta atgttaattt    600
cccacaatcc atggggcgc ttagtggaag gattaatatt atgtttaagg gaatagttta    660 tatggaccctt tttgtcaaca ataagctatt gtaaagatat ttaatgttct gtttatttaa    720
ttgcttctta aattgatatg attttcttat aaaacagaaa agaattataa gaatatattg    780
aaaataaaag aattgaaagg taaaaaaaaa aaaaaaaaaa aaaaaaaaaa aaaaaaaaaa    840
aaaaaaaaaa aa    852
```

<210> SEQ ID NO 17
<211> LENGTH: 849
<212> TYPE: DNA
<213> ORGANISM: Mus musculus

<400> SEQUENCE: 17

```
gagcactcgc agggcactgg gtacccagca ctgagtacat caactcctgg agctgagaat    60
ggcctgcggt ggcaagcgtc tgctcttcct tgctttggca tgggtactgc tggctcacct    120
ctgcagccag gcagaagcaa gcaactacga ctgttgcctc tcgtacatac agacgcctct    180
tccttccaga gctattgtgg gtttcacaag acagatggcc gatgaagctt gtgacattaa    240
tgctatcatc tttcacacga agaaaagaaa atctgtgtgc gctgatccaa agcagaactg    300
ggtgaaaagg gctgtgaacc tcctcagcct aagagtcaag aagatgtaaa aaactgatgc    360
ttttttggga tggaattgga cacagcccaa ggaggaaatg atcacagctg gggttgaagg    420
cttcacctgc acatcactgc acagacctga tttgtgtccc agtggacttg tccaatggat    480
gaagttgatt catattgcat catagtgtgt catatttaag ctcacattag agttaagttg    540
tattttatgt tatttataga tctgaatttt ctatgtttag ctatttaatg ttaatttccc    600
acaatccatg ggggcgctta gtggaaggat taatatttatg tttaagggaa tagtttatat    660
ggaccttttt gtcaacaata agctattgta aagatattta atgttctgtt tatttaattg    720
cttcttaaat tgatatgatt ttcttataaa acagaaaaga attataagaa tatattgaaa    780
ataaaagaat tgaaaggtaa aaaaaaaaaa aaaaaaaaaa aaaaaaaaaa aaaaaaaaaa    840
aaaaaaaaa    849
```

<210> SEQ ID NO 18
<211> LENGTH: 97
<212> TYPE: PRT
<213> ORGANISM: Mus musculus

<400> SEQUENCE: 18

```
Met Ala Cys Gly Gly Lys Arg Leu Leu Phe Leu Ala Leu Ala Trp Val
 1               5                  10                  15

Leu Leu Ala His Leu Cys Ser Gln Ala Glu Ala Ala Ser Asn Tyr Asp
            20                  25                  30

Cys Cys Leu Ser Tyr Ile Gln Thr Pro Leu Pro Ser Arg Ala Ile Val
        35                  40                  45

Gly Phe Thr Arg Gln Met Ala Asp Glu Ala Cys Asp Ile Asn Ala Ile
    50                  55                  60

Ile Phe His Thr Lys Lys Arg Lys Ser Val Cys Ala Asp Pro Lys Gln
65                  70                  75                  80
```

-continued

```
Asn Trp Val Lys Arg Ala Val Asn Leu Leu Ser Leu Arg Val Lys Lys
                85                  90                  95
Met
```

<210> SEQ ID NO 19
<211> LENGTH: 1237
<212> TYPE: DNA
<213> ORGANISM: Homo sapiens

<400> SEQUENCE: 19

```
gctgcagagg attcctgcag aggatcaaga cagcacgtgg acctcgcaca gcctctccca    60
caggtaccat gaaggtctcc gcggcagccc tcgctgtcat cctcattgct actgccctct   120
gcgctcctgc atctgcctcc ccatattcct cggacaccac accctgctgc tttgcctaca   180
ttgcccgccc actgccccgt gcccacatca aggagtattt ctacaccagt ggcaagtgct   240
ccaacccagc agtcgtcttt gtcacccgaa agaaccgcca agtgtgtgcc aacccagaga   300
agaaatgggt tcgggagtac atcaactctt tggagatgag ctaggatgga gagtccttga   360
acctgaactt acacaaattt gcctgtttct gcttgctctt gtcctagctt gggaggcttc   420
ccctcactat cctaccccac ccgctccttg aagggcccag attctaccac acagcagcag   480
ttacaaaaac cttccccagg ctggacgtgg tggctcacgc ctgtaatccc agcactttgg   540
gaggccaagg tgggtggatc acttgaggtc aggagttcga ccagcctg ccaacatga     600
tgaaacccca tctctactaa aaatacaaaa aattagccgg gcgtggtagc gggcgcctgt   660
agtcccagct actcgggagg ctgaggcagg agaatggcgt gaacccggga ggcggagctt   720
gcagtgagcc gagatcgcgc cactgcactc cagcctgggc gacagagcga gactccgtct   780
caaaaaaaaa aaaaaaaaaa aaaatacaaa aattagccgg gcgtggtggc ccacgcctgt   840
aatcccagct actcgggagg ctaaggcagg aaaattgttt gaacccagga ggtggaggct   900
gcagtgagct gagattgtgc cacttcactc cagcctgggt gacaaagtga gactccgtca   960
caacaacaac aacaaaaagc ttccccaact aaagcctaga agagcttctg aggcgctgct  1020
ttgtcaaaag gaagtctcta ggttctgagc tctggctttg ccttggcttt gccagggctc  1080
tgtgaccagg aaggaagtca gcatgcctct agaggcaagg aggggaggaa cactgcactc  1140
ttaagcttcc gccgtctcaa cccctcacag gagcttactg gcaaacatga aaatcggct   1200
taccattaaa gttctcaatg caaccataaa aaaaaaa                          1237
```

<210> SEQ ID NO 20
<211> LENGTH: 91
<212> TYPE: PRT
<213> ORGANISM: Homo sapiens

<400> SEQUENCE: 20

```
Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90
```

<210> SEQ ID NO 21
<211> LENGTH: 579
<212> TYPE: DNA
<213> ORGANISM: Mus musculus

<400> SEQUENCE: 21

```
cttgcagagg actctgagac agcacatgca tctcccacag cctctgccgc gggtaccatg    60
aagatctctg cagctgccct caccatcatc ctcactgcag ccgccctctg caccccgca   120
cctgcctcac catatggctc ggacaccact ccctgctgct ttgcctacct ctccctcgcg   180
ctgcctcgtg cccacgtcaa ggagtatttc tacaccagca gcaagtgctc caatcttgca   240
gtcgtgtttg tcactcgaag gaaccgccaa gtgtgtgcca acccagagaa gaagtgggtt   300
caagaataca tcaactattt ggagatgagc taggatagag ggtttcttga ttctgaccct   360
gtatagcttc cctgtcattg cttgctctag tcctagccag cttggggatg ccactcagta   420
atcccctact cccactcggt cctgggaaaa tgggcatctc agctgctccg aggctctgca   480
cagcaaaccc aagaaatcag catttcatta aatttcaga tgcaaggaca aaaaaaaaa    540
aaaaaaaaaa aaaaaaaaaa aaaaaaaaaa aaaaaaaa                          579
```

<210> SEQ ID NO 22
<211> LENGTH: 91
<212> TYPE: PRT
<213> ORGANISM: Mus musculus

<400> SEQUENCE: 22

```
Met Lys Ile Ser Ala Ala Ala Leu Thr Ile Ile Leu Thr Ala Ala Ala
1               5                   10                  15

Leu Cys Thr Pro Ala Pro Ala Ser Pro Tyr Gly Ser Asp Thr Thr Pro
            20                  25                  30

Cys Cys Phe Ala Tyr Leu Ser Leu Ala Leu Pro Arg Ala His Val Lys
        35                  40                  45

Glu Tyr Phe Tyr Thr Ser Ser Lys Cys Ser Asn Leu Ala Val Val Phe
    50                  55                  60

Val Thr Arg Arg Asn Arg Gln Val Cys Ala Asn Pro Glu Lys Lys Trp
65                  70                  75                  80

Val Gln Glu Tyr Ile Asn Tyr Leu Glu Met Ser
                85                  90
```

<210> SEQ ID NO 23
<211> LENGTH: 813
<212> TYPE: DNA
<213> ORGANISM: Homo sapiens

<400> SEQUENCE: 23

```
agctggtttc agacttcaga aggacacggg cagcagacag tggtcagtcc tttcttggct    60
ctgctgacac tcgagcccac attccgtcac ctgctcagaa tcatgcaggt ctccactgct   120
gcccttgctg tcctcctctg caccatggct ctctgcaacc agttctctgc atcacttgct   180
gctgacacgc cgaccgcctg ctgcttcagc tacacctccc ggcagattcc acagaatttc   240
atagctgact actttgagac gagcagccag tgctccaagc ccggtgtcat cttcctaacc   300
aagcgaagcc ggcaggtctg tgctgacccc agtgaggagt gggtccagaa atatgtcagc   360
gacctggagc tgagtgcctg aggggtccag aagcttcgag cccagcgac ctcggtgggc    420
ccagtgggga ggagcaggag cctgagcctt gggaacatgc gtgtgacctc acagctacc    480
tcttctatgg actggttgtt gccaaacagc cacactgtgg gactcttctt aacttaaatt   540
```

```
ttaatttatt tatactattt agttttgta atttattttc gatttcacag tgtgtttgtg    600
attgtttgct ctgagagttc ccctgtcccc tccccttcc ctcacaccgc gtctggtgac    660
aaccgagtgg ctgtcatcag cctgtgtagg cagtcatggc accaaagcca ccagactgac    720
aaatgtgtat cggatgcttt tgttcagggc tgtgatcggc ctggggaaat aataaagatg    780
ctcttttaaa aggtaaaaaa aaaaaaaaaa aaa                                 813
```

<210> SEQ ID NO 24
<211> LENGTH: 92
<212> TYPE: PRT
<213> ORGANISM: Homo sapiens

<400> SEQUENCE: 24

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 25
<211> LENGTH: 804
<212> TYPE: DNA
<213> ORGANISM: Mus musculus

<400> SEQUENCE: 25

```
gggcatatgg cttcagacac cagaaggata caagcagcag cgagtaccag tccctttct    60 gttctgctga caagctcacc ctctgtcacc tgctcaacat catgaaggtc tccaccactg   120
cccttgctgt tcttctctgt accatgacac tctgcaacca agtcttctca gcgccatatg   180
gagctgacac cccgactgcc tgctgcttct cctacagccg gaagattcca cgccaattca   240
tcgttgacta ttttgaaacc agcagccttt gctcccagcc aggtgtcatt ttcctgacta   300
agagaaaccg gcagatctgc gctgactcca aagagacctg gtccaagaa tacatcactg    360 acctggaact gaatgcctga gagtcttgga ggcagcgagg aaccccccaa acctccatgg   420
gtcccgtgta gagcagggc ttgagccccg gaacattcct gccacctgca tagctccatc    480
tcctataagc tgtttgctgc caagtagcca atcgaggga ctcttcactt gaaatttat    540 ttaatttaat cctattggtt taatactatt taattttgta attttattta ttgtcatact   600
tgtatttgtg actatttatt ctgaaagact tcaggacacg ttcctcaacc ccatctccc    660 tcccagttgg tcacactgtt tggtgacagc tattctaggt agacatgatg acaaagtcat   720
gaactgacaa atgtacaata gatgcttgt ttataccaga gaagtaataa atatgccctt    780
taacaagtga aaaaaaaaaa aaaa                                          804
```

<210> SEQ ID NO 26
<211> LENGTH: 92
<212> TYPE: PRT
<213> ORGANISM: Mus musculus

<400> SEQUENCE: 26

```
Met Lys Val Ser Thr Ala Leu Ala Val Leu Leu Cys Thr Met Thr
1               5                   10                  15

Leu Cys Asn Gln Val Phe Ser Ala Pro Tyr Gly Ala Asp Thr Pro Thr
            20                  25                  30

Ala Cys Cys Phe Ser Tyr Ser Arg Lys Ile Pro Arg Gln Phe Ile Val
        35                  40                  45

Asp Tyr Phe Glu Thr Ser Ser Leu Cys Ser Gln Pro Gly Val Ile Phe
50                  55                  60

Leu Thr Lys Arg Asn Arg Gln Ile Cys Ala Asp Ser Lys Glu Thr Trp
65              70                  75                  80

Val Gln Glu Tyr Ile Thr Asp Leu Glu Leu Asn Ala
                85                  90
```

```
<210> SEQ ID NO 27
<211> LENGTH: 305
<212> TYPE: DNA
<213> ORGANISM: Mus musculus

<400> SEQUENCE: 27
ctctctggag tctgagtgcc ctttctacca gccatgagga ctctctgctc tctgctgctg      60
atatgctgcc tccttttctc atataccact ccagctgttg gaagtttaaa agtattgga     120 tacgaagcag aacttgacca ctgccacacc aatggagggt actgtgtcag agccatttgt     180
cctccttctg ccaggcgtcc tgggagctgt tcccagaga agaacccctg ttgcaagtac     240
atgaaatgat tagaaggaag cacatggaag tcaagtgaca gatgtgtaat tgatgtttca     300
ataaa                                                                 305
```

```
<210> SEQ ID NO 28
<211> LENGTH: 71
<212> TYPE: PRT
<213> ORGANISM: Mus musculus

<400> SEQUENCE: 28

Met Arg Thr Leu Cys Ser Leu Leu Leu Ile Cys Cys Leu Leu Phe Ser
1               5                   10                  15

Tyr Thr Thr Pro Ala Val Gly Ser Leu Lys Ser Ile Gly Tyr Glu Ala
            20                  25                  30

Glu Leu Asp His Cys His Thr Asn Gly Gly Tyr Cys Val Arg Ala Ile
        35                  40                  45

Cys Pro Pro Ser Ala Arg Arg Pro Gly Ser Cys Phe Pro Glu Lys Asn
50                  55                  60

Pro Cys Cys Lys Tyr Met Lys
65                  70
```

```
<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggggattggt tttgacgttt ttgcg                                            25
```

```
<210> SEQ ID NO 30
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 30
aagcattaaa taaagcgaat acatccttat                                          30

<210> SEQ ID NO 31
<211> LENGTH: 1504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(25)
<220> FEATURE:
<221> NAME/KEY: CDS
<222> LOCATION: (29)..(1489)
<220> FEATURE:
<221> NAME/KEY: CDS
<222> LOCATION: (1493)..(1504)

<400> SEQUENCE: 31
```

| | | | | | | | | | | | | | | | | |
|---|---|---|---|---|---|---|---|---|---|---|---|---|---|---|---|---|
|c tgc agt cac cgt cgt cga cag agc tga gat cct aca gga gtc cag ggc | | | | | | | | | | | | | | | | 49|
|  Cys Ser His Arg Arg Arg Gln Ser     Asp Pro Thr Gly Val Gln Gly| | | | | | | | | | | | | | | | |
|  1               5                  10                 15| | | | | | | | | | | | | | | | |

```
tgg aga gaa aac ctc tgc gag gaa aag gaa gga gca agc cgt gaa ttt        97
Trp Arg Glu Asn Leu Cys Glu Glu Lys Glu Gly Ala Ser Arg Glu Phe
             20                  25                  30 aag gga cgc tgt gaa gca atc atg gat gca atg aag aga ggg ctc tgc       145
Lys Gly Arg Cys Glu Ala Ile Met Asp Ala Met Lys Arg Gly Leu Cys
                 35                  40                  45 tgt gtg ctg ctg ctg tgt gga gca gtc ttc gtt tcg ccc agc ggt acc       193
Cys Val Leu Leu Leu Cys Gly Ala Val Phe Val Ser Pro Ser Gly Thr
         50                  55                  60 gga tcc gca gca agc aac ttt gac tgc tgt ctt gga tac aca gac cgt       241
Gly Ser Ala Ala Ser Asn Phe Asp Cys Cys Leu Gly Tyr Thr Asp Arg
 65                  70                  75 att ctt cat cct aaa ttt att gtg ggc ttc aca cgg cag ctg gcc aat       289
Ile Leu His Pro Lys Phe Ile Val Gly Phe Thr Arg Gln Leu Ala Asn
 80                  85                  90                  95 gaa ggc tgt gac atc aat gct atc atc ttt cac aca aag aaa aag ttg       337
Glu Gly Cys Asp Ile Asn Ala Ile Ile Phe His Thr Lys Lys Lys Leu
                100                 105                 110 tct gtg tgc gca aat cca aaa cag act tgg gtg aaa tat att gtg cgt       385
Ser Val Cys Ala Asn Pro Lys Gln Thr Trp Val Lys Tyr Ile Val Arg
            115                 120                 125 ctc ctc agt aaa aaa gtc aag aac atg gaa ttc aac gac gct cag gcg       433
Leu Leu Ser Lys Lys Val Lys Asn Met Glu Phe Asn Asp Ala Gln Ala
        130                 135                 140 ccg aag agt gga tcc atg atg cgc aag ctg gcc atc ctg tcc gtg tcc       481
Pro Lys Ser Gly Ser Met Met Arg Lys Leu Ala Ile Leu Ser Val Ser
    145                 150                 155 tcc ttc ctg ttc gtg gag gcc ctg ttc cag gag tac cag tgc tac ggc       529
Ser Phe Leu Phe Val Glu Ala Leu Phe Gln Glu Tyr Gln Cys Tyr Gly
160                 165                 170                 175 tcc tcc tcc aac acc cgc gtg ctg aac gag ctg aac tac gac aac gcc       577
Ser Ser Ser Asn Thr Arg Val Leu Asn Glu Leu Asn Tyr Asp Asn Ala
                180                 185                 190 ggc acc aac ctg tac aac gag ctg gag atg aac tac tac ggc aag cag       625
Gly Thr Asn Leu Tyr Asn Glu Leu Glu Met Asn Tyr Tyr Gly Lys Gln
            195                 200                 205
```

```
gag aac tgg tac tcc ctg aag aag aac tcc cgc tcc ctg ggc gag aac    673
Glu Asn Trp Tyr Ser Leu Lys Lys Asn Ser Arg Ser Leu Gly Glu Asn
        210                 215                 220 gac gac ggc aac aac gag gac aac gag aag ctg cgc aag ccc aag cac    721
Asp Asp Gly Asn Asn Glu Asp Asn Glu Lys Leu Arg Lys Pro Lys His
225                 230                 235 aag aag ctg aag cag ccc gcc gac ggc aac ccc gac ccc aac gcc aac    769
Lys Lys Leu Lys Gln Pro Ala Asp Gly Asn Pro Asp Pro Asn Ala Asn
240                 245                 250                 255 ccc aac gtg gac ccc aac gcc aac ccc aac gtg gac ccc aac gcc aac    817
Pro Asn Val Asp Pro Asn Ala Asn Pro Asn Val Asp Pro Asn Ala Asn
            260                 265                 270 ccc aac gtg gac ccc aac gcc aac ccc aac gcc aac ccc aac gcc aac    865
Pro Asn Val Asp Pro Asn Ala Asn Pro Asn Ala Asn Pro Asn Ala Asn
        275                 280                 285 ccc aac gcc aac ccc aac gcc aac ccc aac gcc aac ccc aac gcc aac    913
Pro Asn Ala Asn Pro Asn Ala Asn Pro Asn Ala Asn Pro Asn Ala Asn
    290                 295                 300 ccc aac gcc aac ccc aac gcc aac ccc aac gcc aac ccc aac gcc aac    961
Pro Asn Ala Asn Pro Asn Ala Asn Pro Asn Ala Asn Pro Asn Ala Asn
305                 310                 315 ccc aac gcc aac ccc aac gcc aac ccc aac gcc aac ccc aac gcc aac    1009
Pro Asn Ala Asn Pro Asn Ala Asn Pro Asn Ala Asn Pro Asn Ala Asn
320                 325                 330                 335 ccc aac gcc aac ccc aac gcc aac ccc aac gtg gac ccc aac gcc aac    1057
Pro Asn Ala Asn Pro Asn Ala Asn Pro Asn Val Asp Pro Asn Ala Asn
            340                 345                 350 ccc aac gcc aac ccc aac aag aac aac cag ggc aac ggc cag ggc cac    1105
Pro Asn Ala Asn Pro Asn Lys Asn Asn Gln Gly Asn Gly Gln Gly His
        355                 360                 365 aac atg ccc aac gac ccc aac cgc aac gtg gac gag aac gcc aac gcc    1153
Asn Met Pro Asn Asp Pro Asn Arg Asn Val Asp Glu Asn Ala Asn Ala
    370                 375                 380 aac tcc gcc gtg aag aac aac aac gag gag ccc tcc gac aag cac        1201
Asn Ser Ala Val Lys Asn Asn Asn Glu Glu Pro Ser Asp Lys His
385                 390                 395 atc aag gag tac ctg aac aag atc cag aac tcc ctg tcc acc gag tgg    1249
Ile Lys Glu Tyr Leu Asn Lys Ile Gln Asn Ser Leu Ser Thr Glu Trp
400                 405                 410                 415 tcc ccc tgc tcc gtg acc tgc ggc aac ggc atc cag gtg cgc atc aag    1297
Ser Pro Cys Ser Val Thr Cys Gly Asn Gly Ile Gln Val Arg Ile Lys
            420                 425                 430 ccc ggc tcc gcc aac aag ccc aag gac gag ctg gac tac gcc aac gac    1345
Pro Gly Ser Ala Asn Lys Pro Lys Asp Glu Leu Asp Tyr Ala Asn Asp
        435                 440                 445 atc gag aag aaa atc tgc aag atg gag aag tgc tcc tcc gtg ttc aac    1393
Ile Glu Lys Lys Ile Cys Lys Met Glu Lys Cys Ser Ser Val Phe Asn
    450                 455                 460 gtg gtg aac tcc tcc atc ggc ctg atc atg gtg ctg tcc ttc ctg ttc    1441
Val Val Asn Ser Ser Ile Gly Leu Ile Met Val Leu Ser Phe Leu Phe
465                 470                 475 ctg aac aga tcc gca gaa gaa cag aaa ctg atc tca gaa gag gat ctg    1489
Leu Asn Arg Ser Ala Glu Glu Gln Lys Leu Ile Ser Glu Glu Asp Leu
480                 485                 490                 495 tga tct aga aga tct                                                1504
Ser Arg Arg Ser <210> SEQ ID NO 32
<211> LENGTH: 457
<212> TYPE: PRT
<213> ORGANISM: Artificial Sequence
```

-continued

<220> FEATURE:
<223> OTHER INFORMATION: Description of Artificial Sequence: Synthetic
      polypeptide

<400> SEQUENCE: 32

Met Asp Ala Met Lys Arg Gly Leu Cys Cys Val Leu Leu Leu Cys Gly
1               5                   10                  15

Ala Val Phe Val Ser Pro Ser Gly Thr Gly Ser Ala Ala Ser Asn Phe
            20                  25                  30

Asp Cys Cys Leu Gly Tyr Thr Asp Arg Ile Leu His Pro Lys Phe Ile
        35                  40                  45

Val Gly Phe Thr Arg Gln Leu Ala Asn Glu Gly Cys Asp Ile Asn Ala
    50                  55                  60

Ile Ile Phe His Thr Lys Lys Lys Leu Ser Val Cys Ala Asn Pro Lys
65                  70                  75                  80

Gln Thr Trp Val Lys Tyr Ile Val Arg Leu Leu Ser Lys Lys Val Lys
                85                  90                  95

Asn Met Glu Phe Asn Asp Ala Gln Ala Pro Lys Ser Gly Ser Met Met
            100                 105                 110

Arg Lys Leu Ala Ile Leu Ser Val Ser Ser Phe Leu Phe Val Glu Ala
        115                 120                 125

Leu Phe Gln Glu Tyr Gln Cys Tyr Gly Ser Ser Ser Asn Thr Arg Val
    130                 135                 140

Leu Asn Glu Leu Asn Tyr Asp Asn Ala Gly Thr Asn Leu Tyr Asn Glu
145                 150                 155                 160

Leu Glu Met Asn Tyr Tyr Gly Lys Gln Glu Asn Trp Tyr Ser Leu Lys
                165                 170                 175

Lys Asn Ser Arg Ser Leu Gly Glu Asn Asp Asp Gly Asn Asn Glu Asp
            180                 185                 190

Asn Glu Lys Leu Arg Lys Pro Lys His Lys Lys Leu Lys Gln Pro Ala
        195                 200                 205

Asp Gly Asn Pro Asp Pro Asn Ala Asn Pro Asn Val Asp Pro Asn Ala
    210                 215                 220

Asn Pro Asn Val Asp Pro Asn Ala Asn Pro Asn Val Asp Pro Asn Ala
225                 230                 235                 240

Asn Pro Asn Ala Asn Pro Asn Ala Asn Pro Asn Ala Asn Pro Asn Ala
            245                 250                 255

Asn Pro Asn Ala Asn Pro Asn Ala Asn Pro Asn Ala Asn Pro Asn Ala
        260                 265                 270

Asn Pro Asn Ala Asn Pro Asn Ala Asn Pro Asn Ala Asn Pro Asn Ala
    275                 280                 285

Asn Pro Asn Ala Asn Pro Asn Ala Asn Pro Asn Ala Asn Pro Asn Ala
290                 295                 300

Asn Pro Asn Val Asp Pro Asn Ala Asn Pro Asn Ala Asn Pro Asn Lys
            305                 310                 315                 320

Asn Asn Gln Gly Asn Gly Gln Gly His Asn Met Pro Asn Asp Pro Asn
        325                 330                 335

Arg Asn Val Asp Glu Asn Ala Asn Ala Asn Ser Ala Val Lys Asn Asn
    340                 345                 350

Asn Asn Glu Glu Pro Ser Asp Lys His Ile Lys Glu Tyr Leu Asn Lys
355                 360                 365

Ile Gln Asn Ser Leu Ser Thr Glu Trp Ser Pro Cys Ser Val Thr Cys
            370                 375                 380

Gly Asn Gly Ile Gln Val Arg Ile Lys Pro Gly Ser Ala Asn Lys Pro
385                 390                 395                 400

Lys Asp Glu Leu Asp Tyr Ala Asn Asp Ile Glu Lys Lys Ile Cys Lys
                405                 410                 415

Met Glu Lys Cys Ser Ser Val Phe Asn Val Val Asn Ser Ser Ile Gly
            420                 425                 430

Leu Ile Met Val Leu Ser Phe Leu Phe Leu Asn Arg Ser Ala Glu Glu
        435                 440                 445

Gln Lys Leu Ile Ser Glu Glu Asp Leu
    450                 455

<210> SEQ ID NO 33
<211> LENGTH: 1435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ctgcagtcac cgtcgtcgac agagctgaga tcctacagga gtccagggct ggagagaaaa      60
cctctgcgag gaaaaggaag gagcaagccg tgaatttaag ggacgctgtg aagcaatcat     120
ggatgcaatg aagagagggc tctgctgtgt gctgctgctg tgtggagcag tcttcgtttc     180
gcccagcggt accggatccg cagcaagcaa ctttgactgc gtcttggat acacagaccg      240 tattcttcat cctaaattta ttgtgggctt cacacggcag ctggccaatg aaggctgtga     300
catcaatgct atcatctttc acacaaagaa aaagttgtct gtgtgcgcaa atccaaaaca     360
gacttgggtg aaatatattg tgcgtctcct cagtaaaaaa gtcaagaaca tggaattcaa     420
cgacgctcag gcgccgaaga gtggatccat gatgcgcaag ctggccatcc tgtccgtgtc     480
ctccttcctg ttcgtggagg ccctgttcca ggagtaccag tgctacggct cctcctccaa     540
cacccgcgtg ctgaacgagc tgaactacga caacgccggc accaacctgt acaacgagct     600
ggagatgaac tactacggca agcaggagaa ctggtactcc ctgaagaaga actcccgctc     660
cctgggcgag aacgacgacg gcaacaacga ggacaacgag aagctgcgca agcccaagca     720
caagaagctg aagcagcccg ccgacggcaa ccccgacccc aacgccaacc ccaacgtgga     780
ccccaacgcc aaccccaacg tggaccccaa cgccaacccc aacgtggacc ccaacgccaa     840
ccccaacgcc aaccccaacg ccaaccccaa cgccaacccc aacgccaacc ccaacgccaa     900
ccccaacgcc aaccccaacg ccaaccccaa cgccaacccc aacgccaacc ccaacgccaa     960
ccccaacgcc aaccccaacg ccaaccccaa cgccaacccc aacgccaacc ccaacgccaa    1020
ccccaacgcc aaccccaacg tggaccccaa cgccaacccc aacgccaacc ccaacaagaa    1080
caaccagggc aacggccagg ccacaacat gccaacgac cccaaccgca acgtggacga     1140
gaacgccaac gccaactccg ccgtgaagaa caacaacaac gaggagccct ccgacaagca    1200
catcaaggag tacctgaaca agatccagaa ctccctgtcc accgagtggt cccccctgctc    1260 cgtgacctgc ggcaacggca tccaggtgcg catcaagccc ggctccgcca acaagcccaa    1320
ggacgagctg gactacgcca acgacatcga gaagaaaatc tgcaagatgg agaagtgcag    1380
atccgcagaa gaacagaaac tgatctcaga agaggatctg tgatctagaa gatct        1435

<210> SEQ ID NO 34
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Met Asp Ala Met Lys Arg Gly Leu Cys Cys Val Leu Leu Leu Cys Gly
1               5                   10                  15
Ala Val Phe Val Ser Pro Ser Gly Thr Gly Ser Ala Ala Ser Asn Phe
            20                  25                  30
Asp Cys Cys Leu Gly Tyr Thr Asp Arg Ile Leu His Pro Lys Phe Ile
        35                  40                  45
Val Gly Phe Thr Arg Gln Leu Ala Asn Glu Gly Cys Asp Ile Asn Ala
50                  55                  60
Ile Ile Phe His Thr Lys Lys Leu Ser Val Cys Ala Asn Pro Lys
65                  70                  75                  80
Gln Thr Trp Val Lys Tyr Ile Val Arg Leu Leu Ser Lys Val Lys
                85                  90                  95
Asn Met Glu Phe Asn Asp Ala Gln Ala Pro Lys Ser Gly Ser Met Met
            100                 105                 110
Arg Lys Leu Ala Ile Leu Ser Val Ser Ser Phe Leu Phe Val Glu Ala
        115                 120                 125
Leu Phe Gln Glu Tyr Gln Cys Tyr Gly Ser Ser Ser Asn Thr Arg Val
130                 135                 140
Leu Asn Glu Leu Asn Tyr Asp Asn Ala Gly Thr Asn Leu Tyr Asn Glu
145                 150                 155                 160
Leu Glu Met Asn Tyr Tyr Gly Lys Gln Glu Asn Trp Tyr Ser Leu Lys
                165                 170                 175
Lys Asn Ser Arg Ser Leu Gly Glu Asn Asp Gly Asn Asn Glu Asp
            180                 185                 190
Asn Glu Lys Leu Arg Lys Pro Lys His Lys Lys Leu Lys Gln Pro Ala
        195                 200                 205
Asp Gly Asn Pro Asp Pro Asn Ala Asn Pro Asn Val Asp Pro Asn Ala
        210                 215                 220
Asn Pro Asn Val Asp Pro Asn Ala Asn Pro Asn Val Asp Pro Asn Ala
225                 230                 235                 240
Asn Pro Asn Ala Asn Pro Asn Ala Asn Pro Asn Ala Asn Pro Asn Ala
                245                 250                 255
Asn Pro Asn Ala Asn Pro Asn Ala Asn Pro Asn Ala Asn Pro Asn Ala
            260                 265                 270
Asn Pro Asn Ala Asn Pro Asn Ala Asn Pro Asn Ala Asn Pro Asn Ala
        275                 280                 285
Asn Pro Asn Ala Asn Pro Asn Ala Asn Pro Asn Ala Asn Pro Asn Ala
        290                 295                 300
Asn Pro Asn Val Asp Pro Asn Ala Asn Pro Asn Ala Asn Pro Asn Lys
305                 310                 315                 320
Asn Asn Gln Gly Asn Gly Gln Gly His Asn Met Pro Asn Asp Pro Asn
                325                 330                 335
Arg Asn Val Asp Glu Asn Ala Asn Ala Asn Ser Ala Val Lys Asn Asn
            340                 345                 350
Asn Asn Glu Glu Pro Ser Asp Lys His Ile Lys Glu Tyr Leu Asn Lys
        355                 360                 365
Ile Gln Asn Ser Leu Ser Thr Glu Trp Ser Pro Cys Ser Val Thr Cys
370                 375                 380
Gly Asn Gly Ile Gln Val Arg Ile Lys Pro Gly Ser Ala Asn Lys Pro
385                 390                 395                 400
Lys Asp Glu Leu Asp Tyr Ala Asn Asp Ile Glu Lys Lys Ile Cys Lys
                405                 410                 415
```

Met Glu Lys Cys Arg Ser Ala Glu Glu Gln Lys Leu Ile Ser Glu Glu
              420                 425                 430

Asp Leu

<210> SEQ ID NO 35
<211> LENGTH: 1375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
ctgcagtcac cgtcgtcgac agagctgaga tcctacagga gtccagggct ggagagaaaa    60
cctctgcgag gaaaaggaag gagcaagccg tgaatttaag ggacgctgtg aagcaatcat   120
ggatgcaatg aagagagggc tctgctgtgt gctgctgctg tgtggagcag tcttcgtttc   180
gcccagcggt accggatccg cagcaagcaa ctttgactgc tgtcttggat acacagaccg   240
tattcttcat cctaaattta ttgtgggctt cacacggcag ctggccaatg aaggctgtga   300
catcaatgct atcatctttc acacaaagaa aaagttgtct gtgtgcgcaa atccaaaaca   360
gacttgggtg aaatatattg tgcgtctcct cagtaaaaaa gtcaagaaca tggaattcaa   420
cgacgctcag gcgccgaaga gtggatccat ggagtaccag tgctacggct cctcctccaa   480
cacccgcgtg ctgaacgagc tgaactacga caacgccggc accaacctgt acaacgagct   540
ggagatgaac tactacggca agcaggagaa ctggtactcc ctgaagaaga actcccgctc   600
cctgggcgag aacgacgacg gcaacaacga ggacaacgag aagctgcgca gcccaagca    660
caagaagctg aagcagcccg ccgacggcaa ccccgacccc aacgccaacc ccaacgtgga   720
ccccaacgcc aaccccaacg tggaccccaa cgccaacccc aacgtggacc ccaacgccaa   780
ccccaacgcc aaccccaacg ccaaccccaa cgccaacccc aacgccaacc ccaacgccaa   840
ccccaacgcc aaccccaacg ccaaccccaa cgccaacccc aacgccaacc ccaacgccaa   900
ccccaacgcc aaccccaacg ccaaccccaa cgccaacccc aacgccaacc ccaacgccaa   960
ccccaacgcc aaccccaacg tggaccccaa cgccaacccc aacgccaacc ccaacaagaa  1020
caaccagggc aacggccagg ccacaacat gcccaacgac cccaaccgca acgtggacga  1080
gaacgccaac gccaactccg ccgtgaagaa caacaacaac gaggagccct ccgacaagca  1140
catcaaggag tacctgaaca agatccagaa ctccctgtcc accgagtggt cccctgctc   1200
cgtgacctgc ggcaacggca tccaggtgcg catcaagccc ggctccgcca acaagccaa   1260
ggacgagctg gactacgcca acgacatcga agaaaaatc tgcaagatgg agaagtgcag  1320
atccgcagaa gaacagaaac tgatctcaga agaggatctg tgatctagaa gatct       1375
```

<210> SEQ ID NO 36
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Ala Met Lys Arg Gly Leu Cys Cys Val Leu Leu Leu Cys Gly
1               5                  10                  15

Ala Val Phe Val Ser Pro Ser Gly Thr Gly Ser Ala Ala Ser Asn Phe
            20                  25                  30

```
Asp Cys Cys Leu Gly Tyr Thr Asp Arg Ile Leu His Pro Lys Phe Ile
         35                  40                  45

Val Gly Phe Thr Arg Gln Leu Ala Asn Glu Gly Cys Asp Ile Asn Ala
 50                  55                  60

Ile Ile Phe His Thr Lys Lys Leu Ser Val Cys Ala Asn Pro Lys
 65                  70                  75                  80

Gln Thr Trp Val Lys Tyr Ile Val Arg Leu Leu Ser Lys Lys Val Lys
                 85                  90                  95

Asn Met Glu Phe Asn Asp Ala Gln Ala Pro Lys Ser Gly Ser Met Glu
                100                 105                 110

Tyr Gln Cys Tyr Gly Ser Ser Ser Asn Thr Arg Val Leu Asn Glu Leu
            115                 120                 125

Asn Tyr Asp Asn Ala Gly Thr Asn Leu Tyr Asn Glu Leu Glu Met Asn
130                 135                 140

Tyr Tyr Gly Lys Gln Glu Asn Trp Tyr Ser Leu Lys Lys Asn Ser Arg
145                 150                 155                 160

Ser Leu Gly Glu Asn Asp Gly Asn Asn Glu Asp Asn Glu Lys Leu
                165                 170                 175

Arg Lys Pro Lys His Lys Lys Leu Lys Gln Pro Ala Asp Gly Asn Pro
            180                 185                 190

Asp Pro Asn Ala Asn Pro Asn Val Asp Pro Asn Ala Asn Pro Asn Val
            195                 200                 205

Asp Pro Asn Ala Asn Pro Asn Val Asp Pro Asn Ala Asn Pro Asn Ala
210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
            245                 250                 255

Asn Pro Asn Ala Asn Pro Asn Ala Asn Pro Asn Ala Asn Pro Asn Ala
            260                 265                 270

Asn Pro Asn Ala Asn Pro Asn Ala Asn Pro Asn Ala Asn Pro Asn Val
            275                 280                 285

Asp Pro Asn Ala Asn Pro Asn Ala Asn Pro Asn Lys Asn Asn Gln Gly
            290                 295                 300

Asn Gly Gln Gly His Asn Met Pro Asn Asp Pro Asn Arg Asn Val Asp
305                 310                 315                 320

Glu Asn Ala Asn Ala Asn Ser Ala Val Lys Asn Asn Asn Glu Glu
                325                 330                 335

Pro Ser Asp Lys His Ile Lys Glu Tyr Leu Asn Lys Ile Gln Asn Ser
            340                 345                 350

Leu Ser Thr Glu Trp Ser Pro Cys Ser Val Thr Cys Gly Asn Gly Ile
            355                 360                 365

Gln Val Arg Ile Lys Pro Gly Ser Ala Asn Lys Pro Lys Asp Glu Leu
            370                 375                 380

Asp Tyr Ala Asn Asp Ile Glu Lys Lys Ile Cys Lys Met Glu Lys Cys
385                 390                 395                 400

Arg Ser Ala Glu Glu Gln Lys Leu Ile Ser Glu Glu Asp Leu
                405                 410

<210> SEQ ID NO 37
<211> LENGTH: 9
<212> TYPE: PRT
<213> ORGANISM: Plasmodium yoelii

<400> SEQUENCE: 37
```

Ser Tyr Val Pro Ser Glu Gln Ile
1               5

<210> SEQ ID NO 38
<211> LENGTH: 24
<212> TYPE: PRT
<213> ORGANISM: Plasmodium yoelii

<400> SEQUENCE: 38

Gln Gly Pro Gly Ala Pro Gln Gly Pro Gly Ala Pro Gln Gly Pro Gly
1               5                   10                  15

Ala Pro Gln Gly Pro Gly Ala Pro
            20

<210> SEQ ID NO 39
<211> LENGTH: 21
<212> TYPE: PRT
<213> ORGANISM: Plasmodium yoelii

<400> SEQUENCE: 39

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Phe Asn Asp Ala Gln Ala Pro Lys Ser
1               5                   10

<210> SEQ ID NO 41
<211> LENGTH: 4913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagcga ctttccattg acgtcaatgg gtggagtatt tacggtaaac     540
tgcccacttg gcagtacatc aagtgtatca tatgccaagt acgccccctta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg aacgcggat    1020
tccccgtgcc aagagtgacg taagtaccgc ctatagactc tataggcaca cccctttggc   1080
tcttatgcat gctatactgt ttttggcttg gggcctatac accccgctt ccttatgcta    1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggcgcct   1920
ggatccagat ctgctgtgcc ttctagttgc cagccatctg ttgtttgccc ctcccccgtg   1980
ccttccttga ccctggaagg tgccactccc actgtccttt cctaataaaa tgaggaaatt   2040
gcatcgcatt gtctgagtag gtgtcattct attctggggg gtggggtggg caggacagc    2100
aaggggagg attgggaaga caatagcagg catgctgggg atgcggtggg ctctatgggt    2160
acccaggtgc tgaagaattg acccggttcc tcctgggcca gaaagaagca ggcacatccc   2220
cttctctgtg acacaccctg tccacgcccc tggttcttag ttccagcccc actcatagga   2280
cactcatagc tcaggagggc tccgccttca atcccacccg ctaaagtact ggagcggtc    2340
tctccctccc tcatcagccc accaaaccaa acctagcctc caagagtggg aagaaattaa   2400
agcaagatag gctattaagt gcagagggag agaaaatgcc tccaacatgt gaggaagtaa   2460
tgagagaaat catagaattt cttccgcttc ctcgctcact gactcgctgc gctcggtcgt   2520
tcggctgcgg cgagcggtat cagctcactc aaaggcggta atacggttat ccacagaatc   2580
aggggataac gcaggaaaga acatgtgagc aaaaggccag caaaaggcca ggaaccgtaa    2640
aaaggccgcg ttgctggcgt ttttccatag gctccgcccc cctgacgagc atcacaaaaa   2700
tcgacgctca agtcagaggt ggcgaaaccc gacaggacta taaagatacc aggcgtttcc   2760
ccctggaagc tccctcgtgc gctctcctgt tccgaccctg ccgcttaccg gatacctgtc   2820
cgcctttctc ccttcgggaa gcgtggcgct ttctcatagc tcacgctgta ggtatctcag   2880
ttcggtgtag tcgttcgct ccaagctggg ctgtgtgcac gaaccccccg ttcagcccga    2940
ccgctgcgcc ttatccggta actatcgtct tgagtccaac ccggtaagac acgacttatc   3000
gccactggca gcagccactg gtaacaggat tagcagagcg aggtatgtag gcggtgctac   3060
agagttcttg aagtggtggc ctaactacgg ctacactaga agaacagtat ttggtatctg   3120
```

```
cgctctgctg aagccagtta ccttcggaaa aagagttggt agctcttgat ccggcaaaca   3180
aaccaccgct ggtagcggtg gttttttttgt ttgcaagcag cagattacgc gcagaaaaaa   3240
aggatctcaa gaagatcctt tgatcttttc tacggggtct gacgctcagt ggaacgaaaa   3300
ctcacgttaa gggattttgg tcatgagatt atcaaaaagg atcttcacct agatcctttt   3360
aaattaaaaa tgaagtttta aatcaatcta agtatatat gagtaaactt ggtctgacag   3420
ttaccaatgc ttaatcagtg aggcacctat ctcagcgatc tgtctatttc gttcatccat   3480
agttgcctga ctccgggggg gggggcgct gaggtctgcc tcgtgaagaa ggtgttgctg   3540
actcatacca ggcctgaatc gccccatcat ccagccagaa agtgagggag ccacggttga   3600
tgagagcttt gttgtaggtg gaccagttgg tgattttgaa cttttgcttt gccacggaac   3660
ggtctgcgtt gtcgggaaga tgcgtgatct gatccttcaa ctcagcaaaa gttcgattta   3720
ttcaacaaag ccgccgtccc gtcaagtcag cgtaatgctc tgccagtgtt acaaccaatt   3780
aaccaattct gattagaaaa actcatcgag catcaaatga actgcaatt tattcatatc   3840 aggattatca ataccatatt tttgaaaaag ccgtttctgt aatgaaggag aaaactcacc   3900
gaggcagttc cataggatgg caagatcctg gtatcggtct gcgattccga ctcgtccaac   3960
atcaatacaa cctattaatt tcccctcgtc aaaaataagg ttatcaagtg agaaatcacc   4020
atgagtgacg actgaatccg gtgagaatgg caaaagctta tgcatttctt tccagacttg   4080
ttcaacaggc cagccattac gctcgtcatc aaaatcactc gcatcaacca aaccgttatt   4140
cattcgtgat tgcgcctgag cgagacgaaa tacgcgatcg ctgttaaaag gacaattaca   4200
aacaggaatc gaatgcaacc ggcgcaggaa cactgccagc gcatcaacaa tattttcacc   4260
tgaatcagga tattcttcta atacctggaa tgctgttttc ccggggatcg cagtggtgag   4320
taaccatgca tcatcaggag tacggataaa atgcttgatg gtcggaagag gcataaattc   4380
cgtcagccag tttagtctga ccatctcatc tgtaacatca ttggcaacgc tacctttgcc   4440
atgtttcaga aacaactctg gcgcatcggg cttcccatac aatcgataga ttgtcgcacc   4500
tgattgcccg acattatcgc gagcccattt atacccatat aaatcagcat ccatgttgga   4560
atttaatcgc ggcctcgagc aagacgtttc ccgttgaata tggctcataa cacccccttgt   4620 attactgttt atgtaagcag acagttttat tgttcatgat gatatatttt tatcttgtgc   4680
aatgtaacat cagagatttt gagacacaac gtggctttcc cccccccccc attattgaag   4740
catttatcag ggttattgtc tcatgagcgg atacatattt gaatgtattt agaaaaataa   4800
acaaataggg gttccgcgca catttccccg aaaagtgcca cctgacgtct aagaaaccat   4860
tattatcatg acattaacct ataaaaatag gcgtatcacg aggccctttc gtc           4913
```

<210> SEQ ID NO 42
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
ctgcagtcac cgtcgtcgac agagctgaga tcctacagga gtccagggct ggagagaaaa    60
cctctgcgag gaaaaggaag gagcaagccg tgaatttaag ggacgctgtg aagcaatcat   120
ggatgcaatg aagagagggc tctgctgtgt gctgctgctg tgtggagcag tcttcgtttc   180
gcccagcggt accggatcc                                                199
```

```
<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 44
<211> LENGTH: 213
<212> TYPE: DNA
<213> ORGANISM: Homo sapiens

<400> SEQUENCE: 44
gcagcaagca actttgactg ctgtcttgga tacacagacc gtattcttca tcctaaattt     60
attgtgggct tcacacggca gctggccaat gaaggctgtg acatcaatgc tatcatcttt   120
cacacaaaga aaaagttgtc tgtgtgcgca aatccaaaac agacttgggt gaaatatatt   180
gtgcgtctcc tcagtaaaaa agtcaagaac atg                                213

<210> SEQ ID NO 45
<211> LENGTH: 71
<212> TYPE: PRT
<213> ORGANISM: Homo sapiens

<400> SEQUENCE: 45

Ala Ala Ser Asn Phe Asp Cys Cys Leu Gly Tyr Thr Asp Arg Ile Leu
1               5                   10                  15

His Pro Lys Phe Ile Val Gly Phe Thr Arg Gln Leu Ala Asn Glu Gly
            20                  25                  30

Cys Asp Ile Asn Ala Ile Ile Phe His Thr Lys Lys Lys Leu Ser Val
        35                  40                  45

Cys Ala Asn Pro Lys Gln Thr Trp Val Lys Tyr Ile Val Arg Leu Leu
    50                  55                  60

Ser Lys Lys Val Lys Asn Met
65                  70

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gaattcaacg acgctcaggc gccgaagagt ggatcc                               36

<210> SEQ ID NO 47
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asn Ala Asn Pro Asn Ala Asn Pro Asn Ala Asn Pro Asn Ala Asn Pro
```

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   | 10 |   |   |   |   | 15 |   |

Asn Ala Asn Pro Asn Ala Asn Pro Asn Ala Asn Pro Asn Ala Asn Pro
            20                  25                  30

Asn Ala Asn Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60

Asn Ala Asn Pro Asn Ala Asn Pro Asn Ala Asn Pro Asn Ala Asn Pro
65                  70                  75                  80

Asn Ala Asn Pro Asn Ala Asn Pro
            85

<210> SEQ ID NO 48
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

| atgatgcgca agctggccat cctgtccgtg tcctccttcc tgttcgtgga ggccctgttc | 60 |
| caggagtacc agtgctacgg ctcctcctcc aacacccgcg tgctgaacga gctgaactac | 120 |
| gacaacgccg gcaccaacct gtacaacgag ctggagatga actactacgg caagcaggag | 180 |
| aactggtact ccctgaagaa gaactcccgc tccctgggcg agaacgacga cggcaacaac | 240 |
| gaggacaacg agaagctgcg caagcccaag cacaagaagc tgaagcagcc cgccgacggc | 300 |
| aaccccgacc ccaacgccaa ccccaacgtg gaccccaacg ccaaccccaa cgtggacccc | 360 |
| aacgccaacc ccaacgtgga ccccaacgcc aaccccaacg ccaaccccaa cgccaacccc | 420 |
| aacgccaacc ccaacgccaa ccccaacgcc aaccccaacg ccaaccccaa cgccaacccc | 480 |
| aacgccaacc ccaacgccaa ccccaacgcc aaccccaacg ccaaccccaa cgccaacccc | 540 |
| aacgccaacc ccaacgccaa ccccaacgcc aaccccaacg ccaaccccaa cgccaacccc | 600 |
| aacgccaacc ccaacgccaa ccccaacaag aacaaccagg gcaacggcca gggccacaac | 660 |
| atgcccaacg accccaaccg caacgtggac gagaacgcca acgccaactc cgccgtgaag | 720 |
| aacaacaaca cgaggagcc ctccgacaag cacatcaagg agtacctgaa caagatccag | 780 |
| aactccctgt ccaccgagtg gtccccctgc tccgtgacct gcggcaacgg catccaggtg | 840 |
| cgcatcaagc ccggctccgc caacaagccc aaggacgagc tggactacgc caacgacatc | 900 |
| gagaagaaaa tctgcaagat ggagaagtgc tcctccgtgt caacgtggt gaactcctcc | 960 |
| atcggcctga tcatggtgct gtccttcctg ttcctgaac | 999 |

<210> SEQ ID NO 49
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr

```
                35                  40                  45
Asn Glu Leu Glu Met Asn Tyr Tyr Gly Lys Gln Glu Asn Trp Tyr Ser
 50                  55                  60

Leu Lys Lys Asn Ser Arg Ser Leu Gly Glu Asn Asp Asp Gly Asn Asn
 65                  70                  75                  80

Glu Asp Asn Glu Lys Leu Arg Lys Pro Lys His Lys Lys Leu Lys Gln
                 85                  90                  95

Pro Ala Asp Gly Asn Pro Asp Pro Asn Ala Asn Pro Asn Val Asp Pro
                100                 105                 110

Asn Ala Asn Pro Asn Val Asp Pro Asn Ala Asn Pro Asn Val Asp Pro
                115                 120                 125

Asn Ala Asn Pro Asn Ala Asn Pro Asn Ala Asn Pro Asn Ala Asn Pro
                130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
                180                 185                 190

Asn Ala Asn Pro Asn Val Asp Pro Asn Ala Asn Pro Asn Ala Asn Pro
                195                 200                 205

Asn Lys Asn Asn Gln Gly Asn Gly Gln Gly His Asn Met Pro Asn Asp
                210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255

Asn Lys Ile Gln Asn Ser Leu Ser Thr Glu Trp Ser Pro Cys Ser Val
                260                 265                 270

Thr Cys Gly Asn Gly Ile Gln Val Arg Ile Lys Pro Gly Ser Ala Asn
                275                 280                 285

Lys Pro Lys Asp Glu Leu Asp Tyr Ala Asn Asp Ile Glu Lys Lys Ile
                290                 295                 300

Cys Lys Met Glu Lys Cys Ser Ser Val Phe Asn Val Val Asn Ser Ser
305                 310                 315                 320

Ile Gly Leu Ile Met Val Leu Ser Phe Leu Phe Leu Asn
                325                 330

<210> SEQ ID NO 50
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agatccgcag aagaacagaa actgatctca gaagaggatc tgtgatctag aagatct        57

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

```
Arg Ser Ala Glu Glu Gln Lys Leu Ile Ser Glu Glu Asp Leu
1               5                   10

<210> SEQ ID NO 52
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Lys Lys Cys Thr Ile Leu Val Val Ala Ser Leu Leu Leu Val Asp
1               5                   10                  15

Ser Leu Leu Pro Gly Tyr Gly Gln Gln Lys Ser Val Gln Ala Gln Arg
                20                  25                  30

Asn Leu Asn Glu Leu Cys Tyr Asn Glu Glu Asn Asp Asn Lys Leu Tyr
            35                  40                  45

His Val Leu Asn Ser Lys Asn Gly Lys Ile Tyr Asn Arg Asn Ile Val
        50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Gln Gln Pro Pro Gln Gln Pro Pro Pro
225                 230                 235                 240

Gln Gln Pro Pro Gln Gln Pro Gln Gln Pro Pro Gln Gln Gln Pro Pro
                245                 250                 255

Gln Gln Pro Arg Pro Gln Pro Asp Gly Asn Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350
```

```
Asn Ser Leu Gly Phe Val Ile Leu Leu Val Leu Val Phe Phe Asn
        355                 360                 365
```

<210> SEQ ID NO 53
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Lys Asn Asn Gln Gly Asn Gly Gln Gly His Asn Met Pro Asn Asp
    210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255

Asn Lys Ile Gln Asn Ser Leu Ser Thr Glu Trp Ser Pro Cys Ser Val
            260                 265                 270

Thr Cys Gly Asn Gly Ile Gln Val Arg Ile Lys Pro Gly Ser Ala Asn
        275                 280                 285

Lys Pro Lys Asp Glu Leu Asp Tyr Ala Asn Asp Ile Glu Lys Lys Ile
    290                 295                 300

Cys Lys Met Glu Lys Cys Ser Ser Val Phe Asn Val Val Asn Ser Ser
305                 310                 315                 320

Ile Gly Leu Ile Met Val Leu Ser Phe Leu Phe Leu Asn Arg Ser Ala
                325                 330                 335

Glu Glu Gln Lys Leu Ile Ser Glu Glu Asp Leu
            340                 345
```

```
<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Ser His Arg Arg Arg Gln Ser
1               5

<210> SEQ ID NO 55
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Pro Thr Gly Val Gln Gly Trp Arg Glu Asn Leu Cys Glu Glu Lys
1               5                   10                  15

Glu Gly Ala Ser Arg Glu Phe Lys Gly Arg Cys Glu Ala Ile Met Asp
            20                  25                  30

Ala Met Lys Arg Gly Leu Cys Cys Val Leu Leu Cys Gly Ala Val
        35                  40                  45

Phe Val Ser Pro Ser Gly Thr Gly Ser Ala Ala Ser Asn Phe Asp Cys
    50                  55                  60

Cys Leu Gly Tyr Thr Asp Arg Ile Leu His Pro Lys Phe Ile Val Gly
65                  70                  75                  80

Phe Thr Arg Gln Leu Ala Asn Glu Gly Cys Asp Ile Asn Ala Ile Ile
                85                  90                  95

Phe His Thr Lys Lys Lys Leu Ser Val Cys Ala Asn Pro Lys Gln Thr
            100                 105                 110

Trp Val Lys Tyr Ile Val Arg Leu Leu Ser Lys Val Lys Asn Met
        115                 120                 125

Glu Phe Asn Asp Ala Gln Ala Pro Lys Ser Gly Ser Met Met Arg Lys
    130                 135                 140

Leu Ala Ile Leu Ser Val Ser Ser Phe Leu Phe Val Glu Ala Leu Phe
145                 150                 155                 160

Gln Glu Tyr Gln Cys Tyr Gly Ser Ser Ser Asn Thr Arg Val Leu Asn
                165                 170                 175

Glu Leu Asn Tyr Asp Asn Ala Gly Thr Asn Leu Tyr Asn Glu Leu Glu
            180                 185                 190

Met Asn Tyr Tyr Gly Lys Gln Glu Asn Trp Tyr Ser Leu Lys Lys Asn
        195                 200                 205

Ser Arg Ser Leu Gly Glu Asn Asp Asp Gly Asn Asn Glu Asp Asn Glu
    210                 215                 220

Lys Leu Arg Lys Pro Lys His Lys Lys Leu Lys Gln Pro Ala Asp Gly
225                 230                 235                 240

Asn Pro Asp Pro Asn Ala Asn Pro Asn Val Asp Pro Asn Ala Asn Pro
                245                 250                 255

Asn Val Asp Pro Asn Ala Asn Pro Asn Val Asp Pro Asn Ala Asn Pro
            260                 265                 270

Asn Ala Asn Pro Asn Ala Asn Pro Asn Ala Asn Pro Asn Ala Asn Pro
        275                 280                 285

Asn Ala Asn Pro Asn Ala Asn Pro Asn Ala Asn Pro Asn Ala Asn Pro
```

```
                        290                 295                 300
Asn Ala Asn Pro Asn Ala Asn Pro Asn Ala Asn Pro Asn Ala Asn Pro
305                 310                 315                 320

Asn Ala Asn Pro Asn Ala Asn Pro Asn Ala Asn Pro Asn Ala Asn Pro
                325                 330                 335

Asn Val Asp Pro Asn Ala Asn Pro Asn Ala Asn Pro Asn Lys Asn Asn
                340                 345                 350

Gln Gly Asn Gly Gln Gly His Asn Met Pro Asn Asp Pro Asn Arg Asn
            355                 360                 365

Val Asp Glu Asn Ala Asn Ala Asn Ser Ala Val Lys Asn Asn Asn Asn
            370                 375                 380

Glu Glu Pro Ser Asp Lys His Ile Lys Glu Tyr Leu Asn Lys Ile Gln
385                 390                 395                 400

Asn Ser Leu Ser Thr Glu Trp Ser Pro Cys Ser Val Thr Cys Gly Asn
                405                 410                 415

Gly Ile Gln Val Arg Ile Lys Pro Gly Ser Ala Asn Lys Pro Lys Asp
                420                 425                 430

Glu Leu Asp Tyr Ala Asn Asp Ile Glu Lys Lys Ile Cys Lys Met Glu
            435                 440                 445

Lys Cys Ser Ser Val Phe Asn Val Val Asn Ser Ser Ile Gly Leu Ile
        450                 455                 460

Met Val Leu Ser Phe Leu Phe Leu Asn Arg Ser Ala Glu Glu Gln Lys
465                 470                 475                 480

Leu Ile Ser Glu Glu Asp Leu
                485

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Arg Arg Ser
1
```

What is claimed is:

1. A pharmaceutical composition comprising: (a.) a plasmid comprising a nucleic acid sequence consisting of the nucleotide sequence as set forth in SEQ ID NO:31; and (b.) a liposome adjuvant comprising a commixture of (±)-N-(3-aminopropyl)-N,N-dimethyl-2,3-bis(cis-9-tetradecenyloxy)-1-propanaminium bromide (GAP-DMORIE) and 1,2-diphytanoyl-sn-glycero-3-phosphoethanolamine (DPyPE).

2. A method for eliciting an immune response in a subject comprising administering to the subject a pharmaceutical composition comprising a nucleic acid sequence encoding a parasite antigen or fragment thereof fused to an immune cell product.

* * * * *